US006759525B2

(12) United States Patent
Stratakis et al.

(10) Patent No.: US 6,759,525 B2
(45) Date of Patent: Jul. 6, 2004

(54) PROTEIN KINASE A AND CARNEY COMPLEX

(75) Inventors: Constantine Stratakis, Rockville, MD (US); Lawrence Kirschner, North Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/935,916

(22) Filed: Aug. 23, 2001

(65) Prior Publication Data

US 2003/0022180 A1 Jan. 30, 2003

Related U.S. Application Data

(60) Provisional application No. 60/228,211, filed on Aug. 25, 2000.

(51) Int. Cl.[7] .................. C07H 21/02; C07H 21/04; C12Q 1/68
(52) U.S. Cl. .............. 536/23.1; 536/22.1; 536/24.3; 536/24.31; 536/24.33; 435/6; 435/91.2
(58) Field of Search ................... 536/23.1, 24.3, 536/24.31, 24.32, 24.33

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,873,191 A | 10/1989 | Wagner et al. |
| 4,965,188 A | 10/1990 | Mullis et al. |
| 5,322,770 A | 6/1994 | Gelfand |
| 5,652,096 A | 7/1997 | Cimino |

FOREIGN PATENT DOCUMENTS

WO     WO90/08832     8/1990

OTHER PUBLICATIONS

Kirschner et al (Human Mol. Genetics (2000) 9(20):3037–3046).*
Casey et al (J. Clin. Invest. (Aug. 5, 2000) 106:R31–38).*
Carney and Young (1992) "Primary Pigmented Nodular Adrenocortical Disease and its Associated Conditions," Endocrinologist 2:6–21.
Carney (1995) "Carney Complex: The Complex of Myxomas, Spotty Pigmentation, Endocrine Overactivity, and Schwannomas," Semin. Dermatol. 14:90–98.
Stratakis et al. (1998) "Carney Complex: Diagnosis and Management of the Complex of Spotty Skin Pigmentation, Myxomas, Endocrine Overactivity, and Schwannomas," Am. J. Med. Genet., 80:183–185 (1998).
Carney et al. (1985) "Dominant Inheritance of the Complex of Myxomas, Spotty Pigmentation, and Endocrine Overactivity," Mayo Clin. Proc., 61:165–172.

Stratakis (2000) "Genetics of Carney Complex and Related Familial Lentiginoses, and Other Multiple Tumor Syndromes," Frontiers in Biosci. 5:D353–366.
Atherton et al. (1980) "A syndrome of various cutaneous pigmented lesions, myxoid neurofibromata and atrial myxoma: the NAME syndrome," Brit. J. Dermatol. 103:421–429.
Rhodes et al. (1984) "Mucocutaneous lenligines, cardiomucocutaneous myxomas, and multiple blue nevi: The 'LAMB' syndrome," J. Am. Acad. Dermatol. 10:72–82.
Stratakis (2000) "Genetics of Carney Complex and Related Familial Lentiginoses, and Other Multiple Tumor Syndromes," Pediatr. Pathol. Mol. Med. 19:41–68.
Young et al. (1989) "Familial Cushing's Syndrome Due to Primary Pigmented Nodular Adrenocortical Disease," N. Eng. J. Med. 321:1659–1664.
Berkhout et al. (1989) "Familial Cushing's Dyndrome Due to Nodular Adrenocortical Dysplasia is an Inheribted Disease of Immunological Origin," Clin. Endocrinol. 31:185–191 (1989).
Stratakis et al. (1996) "Carney Complex, a Familial Multiple Neoplasia and Lentiginosis Syndrome," J. Clin. Invest. 97:699–705.
Casey et al. (1998) "Identification of a Novel Genetic Locus for Familial Cardiac Myxomas and Carney Complex," Circul. 98:2560–2566.
Stratakis et al. (1999) "Paradoxical Response to Dexamethasone in the Diagnosis of Primary Pigmented Nodular Adrenocortical Disease," Ann. Intern. Med. 131:585–591.
Weinstein et al. (1991) "Activating Mutations of the Stimulatory G Protein in the McCune–Albright Syndrome," N. Eng. J. Med. 325:1688–1695.
Scott (1991) "Cyclic Nucleotide–Dependent Protein Kinases," Pharmac. Ther. 50:123–145.
Basson et al. (1997) "Genetic Heterogeneity of Familial Atrial Myxoma Syndromes (Carney Complex)," Am. J. Cardiol. 79:994–995.

(List continued on next page.)

Primary Examiner—Jeffrey Fredman
(74) Attorney, Agent, or Firm—Leydig, Voit & Mayer, Ltd.

(57) ABSTRACT

The present invention provides compositions and methods useful in the diagnosis and prognosis of Carney complex (CNC), as well as methods and compositions for the identification of compounds useful in the treatment and/or prevention of CNC. In addition, the present invention provides compositions and methods useful in the diagnosis and treatment of conditions associated with skin pigmentation defects, including but not limited to freckling, as well as endocrine tumors including, but not limited to adrenal and pituitary tumors. In addition, the present invention provides methods and compositions for the diagnosis and treatment of various types of cancers associated with abnormal activity of protein kinase A. In particular, the present invention provides genetic and other sequence information, as well as assay systems that will find use in these and related areas.

1 Claim, 9 Drawing Sheets

OTHER PUBLICATIONS

Taymans et al. (1997) "A refined genetic, radiation hybrid and physical map of the Carney complex (CNC) locus on chromosome 2p16; evidence for genetic heterogeneity in the syndrome," Am. J. Hum. Genet. 61:A84 (Suppl).

Liebler et al. (1976) "Familial myxomas in four siblings," J. Thorac. Cardiovasc. Surg. 71:605–608.

Tautz (1989) "Hypervariability of simple sequences as a general source for polymorphic DNA markers," Nucl. Acids Res. 17:6463–6471.

Sun et al. (1998) "A mutated human homologue to yeast Upfl protein has a dominant–negative effect on the decay of nonsensecontaining mRNAs in mammalian cells," Proc. Natl. Acad. Sci. USA 95:10009–10014.

Culbertson (1999) "RNA surveillance, unforeseen consequences for gene expression, inherited genetic disorders and cancer," Trends Genet., 15:74–80.

Maquat (1995) "When cells stop making sense: Effects of nonsense codons on RNA metabolism in vertebrate cells," RNA 1:453–465.

Schwarze et al. (2000) "Null Alleles of the COL5A1 Gene of Type V Collagen Are a Cause of the Classical Forms of Ehlers–Danlos Syndrome (Types I and II)," Am. J. Hum. Genet. 66:1757–1765.

Freddi et al. (2000) "Molecular Diagnosis of Stickler Syndrome: A COL2A1 Stop Codon Mutation Screening Strategy That Is Not Compromised by Mutant mRNA Instability," Am. J. Med. Genet. 90:398–406.

Kozak (1991) "Structural Features in Eurkaryotic mRNAs That Modulate the Initiation of Translation," J. Biol. Chem. 266:19867–19870.

DeMarco et al. (1996) "Sporadic cardiac myxomas and tumors from patients with Carney complex are not associated with activating mutations of the Gsα Gene," Hum. Genet. 98:185–188.

Cummings et al. (1996) "Genetically lean mice result from targeted disruption of the RIIβ subunit of protein kinase A," Nature 382:622–626.

Amieux et al. (1997) "Compensatory Regulation of RIα Protein Levels in Protein Kinase A Mutant Mice," J. Biol. Chem. 272:3993–3998.

Cho et al. (2000) "Extracellular protein kinase A as a cancer biomarker: Its expression by tumor cells and reversal by a myristate–lacking Cα and RIIβ subunit overexpression," Proc. Natl. Acad. Sci. USA 97:837–840.

Beebe et al. (1984) "Two Classes of cAMP Analogs Which Are Selective for the Two Different cAMP–binding Sites of Type II Protein Kinase Demonstrate Synergism When Added Together to Intact Adipocytes," J. Biol. Chem. 259:3539–3547.

Gossen and Bujard (1992) "Tight control of gene expression in mammalian cells by tetracycline–responsive promoters," Proc. Natl. Acad. Sci. USA 89:5547–5551.

Kistner et al. (1996) "Doxycycline–mediated quantitative and tissue–specific control of gene expression in transgenic mice," Proc. Natl. Acad. Sci. USA 93:10933–10938.

Tarutani et al. (1997) "Tissue–specific knockout of the mouse Pigα gene reveals important roles for GPI–anchored proteins in skin development," Proc. Natl. Acad. Sci. USA 94:7400–7405.

Mazzaferri (1993) "Management of a Solitary Thyroid Nodule," N. Eng. J. Med. 328:553–559.

Sarlis (2000) "Expression Patterns of Cellular Growth–Controlling Genes in Non–Medullary Thyroid Cancer: Basic Aspects," Rev. Endocrinol. Metab. Dis. 1:183–196.

Eng (2000) "Editorial: Familial Papillary Thyroid Cancer— Many Syndromes, Too Many Genes," J. Clin. Endocrinol. Metab. 85:1755–1757.

Farid et al. (2000) "Genetics of Follicular Thyroid Cancer," Endocrinol. Metab. Clin. N. Amer. 24:865–883.

Fagin (1997) "Editorial: Familial Nonmedullary Thryoid Carcinoma—the Case for Genetic Susceptibility," J. Clin. Endocrinol. Metab. 82:342–344.

Stratakis et al. (1997) "Thyroid Gland Abnormalities in Patients with the Syndrome of Spotty–Skin Pigmentation, Myxomas, Endocrine Overactivity, and Schwannomas (Carney Complex)," J. Clin. Endocrinol. Metab. 82:2037–2043.

Ain (1995) "Papillary Thyroid Carcinoma," Endocrinol. Metab. Clin. N. Amer. 24:711–760.

Bier et al. (1989) "Multiple Cutaneous Myxomas Coinciding with Repeated Cardiac Myxomas. A syndrome," Thorac. Cardiovasc. Surg. 37:317–319.

Radin and Kempf (1995) "Carney Complex: Report of Three Cases," Radiol. 196:383–386.

Kinzler and Vogelstein (1996) "Lessons from Hereditary Colorectal Cancer," Cell 87:159–170.

Bosman (1999) "The Hamartoma–Adenoma–Carcinoma Sequence," J. Pathol. 188:1–2.

Parma et al.(1993) "Somatic mutations in the thyrotropin receptor gene cause hyperfunctioning thyroid adenomas," Nature 365:649–651.

Fuhrer et al. (1997) "Somatic Mutations in the Thyrotropin Receptor Gene and Not in the $G_2$ α Protein Gene in 31 Toxic Thyroid Nodules," J. Clin. Endocrinol. Metab. 82:3885–3891.

Esapa et al. (1997) "G Protein and Thyrotropin Receptor Mutations in Thyroid Neoplasia," J. Clin. Endocrinol. Metab. 82:493–496.

Russo et al. (1995) "Activating mutations of the TSH receptor in differentiated thyroid carcinomas," Oncogene 11:1907–1911.

Pack et al. (2000) "Genetic and Histologic tudies of Somatomammotropic Pituitary Tumors in Patients with the 'Complex of Spotty Skin Pigmentation, Myxomas, Endocrine Overactivity and Schwannomas,' (Carney Complex),"J. Clin. Endocrinol. Metab. 85:3860–3865.

Bonat et al. (2000) "Papillary Thyroid Carcinoma (PTC) in a Child with Mccune–Albright Syndrome (MAS): More than a Random Association," Proc. 82nd Ann. Meet. Endocrine Soc., Toronto, Canada, Abstract #P2–2099.

Fournes et al. (1998) "Oncogenic potential of a mutant human thyrotropin receptor expressed in FRTL–5 cells," Oncogene 16:985–990.

Du Villard et al. (2000) "Role of the cAMP and MAPK pathways in the transformation of mouse 3T3 fibroblasts by a TSHR gene constitutively activated by point mutation," Oncogene 19:4896–4905.

Michiels et al. (1994) "Oncogenic potential of guanine nucleotide stimulatory factor α subunit in thyroid glands of transgenic mice," Proc. Natl. Acad. Sci. USA 91:10488–10492.

Coppee et al. (1996) "Early occurrence of metastatic differentiated thyroid carcinomas in transgenic mice expressing the A2a adenosine receptor gene and the human papillomavirus type 16 E7 oncogene," Oncogene 13:1471–1482.

Ledent et al. (1997) "Costimulation of Adenylyl Cyclase and Phospholipase C by a Mutant $\alpha_{1B}$–Adrenergic Receptor Transgene Promotes Malignant Transformation of Thyroid Follicular Cells," Endocrinol. 138:369–378.

Elisei et al. (1998) "Genetic and Epigenetic Alterations of the Cyclin–Dependent Kinase Inhibitors $p15^{INK4b}$ and $p16^{INK4a}$ in Human Thyroid Carcinoma Cell Lines and Primary Thyroid Carcinomas," Cancer 83:2185–2193.

Grieco et al. (1990) "PTC is a Novel Rearranged Form of the ret Proto–Oncogene and is Frequently Detected In Vivo in Human Thyroid Papillary Carcinomas," Cell 60:557–563.

Sozzi et al. (1994) "A t(10;17) Translocation Creates the REP/PTC2 Chimeric Transforming Sequence in Papillary Thyroid Carcinoma," Genes, Chromosomes & Canc. 9:244–250.

Lanzi et al. (1992) "Identification of the product of two oncogenic rearranged forms of the RET proto–oncogene in papillary thyroid carcinomas," Oncogene 7:2189–2194.

Bongarzone et al. (1993) "Molecular Characterization of a Thyroid Tumor–Specific Transforming Sequence by the Fusion of ret Tyrosine Kinase and the Regulatory Subunit: RI$\alpha$ of Cyclic AMP–Dependent Protein Kinase A," Mol. Cell Biol. 13:358–366.

Kroll et al. (2000) "PAX8–PPAR$\gamma$1 Fusion in Oncogene Human Thyroid Carcinoma," Science 289:1357–1360.

Ward et al. (1998) "Studies of Allelic Loss in Thyroid Tumors Reveal Major Differences in Chromosomal Instability between Papillary and Follicular Carcinomas," J. Clin. Endocrinol. Metab. 83:525–530.

Kitamura et al. (2000) "Allelotyping of Anaplastic Thyroid Carcinoma: Frequent Allelic Losses on 1q, 9p, 11, 17, 19p, and 22q," Genes, Chromosomes & Canc. 27:244–251.

Gimm et al. (2001) "Somatic Mutation and Germline Variants of MINPP1, a Phosphatase Gene Located in Proximity to PTEN on 10q23.3, in Follicular Thyroid Carcinomas," J. Clin. Endocrinol. Metab. 86:1801–1805.

Zedenius et al. (1996) "Deletions of the long arm of chromosome 10 in progression of follicular thyroid tumors," Hum. Genet. 97:299–303.

Halachmi et al. (1998) "Somatic Mutations of the PTEN Tumor Supressor Gene in Sporadic Follicular Thyroid Tumors," Genes, Chromosomes & Canc. 23:239–243.

Zhou et al. (2000) "Epigenetic PTEN Silencing in Malignant Melanomas without PTEN Mutation," Am. J. Pathol. 157:1123–1128.

Deloukas et al. (1998) "A Physical Map of 30,000 Human Genes," Science 282:744–746.

Yen (2000) "Thyrotropin Receptor Mutations in Thyroid Diseases," Rev. Endocrinol. Metab. Dis. 1:123–129.

Van der Laan et al. (1995) "Expression of Growth Factors and Growth Factor Receptors in Normal and Tumorous Human Thyroid Tissues," Thyroid 5:67–73.

Celta et al. (2000) "Germline Mutations of the APC Gene in Patients with Familial Adenomatous Polyposis–Associated Thyroid Carcinoma: Results from a European Cooperative Study," J. Clin. Endocrinol. Metab. 85:286–292.

Ho et al. (1996) "p53 gene mutation in thyroid carcinoma," Canc. Lett. 103:57–63.

Belfiore et al. (1999) "Insulin/IGF–I hybrid receptors play a major role in IGF–1 signaling in thyroid cancer," Biochimie 81:403–407.

Kimura et al. (1999) "Expression of Transforming Growth Factor $\beta_1$, $\beta_2$, and $\beta_3$ in Multinodular Goiters and Differentiated Thyroid Carcinomas: A Comparative Study," Thyroid 9:119–125.

Delgado and Ganea (2001) "Vasoactive Intestinal peptide and Pituitary Adenylate Cyclase–Activating Polypeptide Inhibit Expression of Fas Ligand in Activated T Lymphocytes by Regulating c–Myc, Nf–$\kappa$B, NF–AT, and Early Growth Factors 2/3,"J. Immunol. 166:1028–1040.

Ramstad et al. (2000) "cAMP–dependent protein kinase (PKA) inhibits T cell activation by phosphorylating Ser–43 of Raf–1 in the MAPK/ERK pathway," Cell Signal. 12:557–563.

Villone et al. (2000) "Association between the expression of E1A oncogene and increased sensitivity to growth inhibition induced by sustained levels of cAMP in rat thyroid cells," Eur. J. Endocrinol. 142:286–293.

Richards (2001) "New Signaling Pathways for Hormones and Cyclic Adenosine 3',5'–Monophosphate Action in Endocrine Cells," Mol. Endocrinol. 15:209–218.

Knudson (2000) "Chasing the Cancer Demon," Ann. Rev. Genet. 34:1–19.

Maniatis et al. (1987) "Regulation of Inducible and Tissue–Specific Gene Expression," Science 236:1237.

Voss et al. (1986) "The Role of Enhancers in the Regulation of Cell–Type Specific Transcriptional Control," Trends Biochem. Sci. 11:287.

Dijkema et al. (1985) "Cloning and Expression of the Chromosomal Immune Interferon Gene of the Rat," EMBO J. 4:761.

Uetsuki et al. (1989) "Isolation and Characterization of the Human Chromosomal Gene for Polypeptide Chain Elongation Factor–I$\alpha$ ," J. Biol. Chem. 264:5791.

Kim et al. (1990) "Use of the human elongation factor I$\alpha$ promoter as a versatile and efficient expression system," Gene 91:217.

Mizushima and Nagata (1990) "pEF–BOS, a powerful mammalian expression vector," Nuc. Acids. Res. 15:5322.

Gorman et al. (1982) "The Rous sarcoma virus long terminal repeat is a strong promoter when introduced into a variety of eukaryotic cells by DNA–mediated transfection," Proc. Natl. Acad. Sci. USA 79:6777.

Boshart et al. (1985) "A Very Strong Enhancer is Located Upstream of an Immediate Early Gene of Human Cytomegalovirus," Cell 41:521.

Sambrook et al., *Molecular Cloning: A Laboratory Manual*, 2nd ed., Cold Spring Harbor Laboratory Press, New York (1989), pp. 16.7–16.8.

Smith and Waterman (1981) "Comparison of Biosequences," Adv. Appl. Math. 2:482.

Needleman amd Wunsch (1970) "A General Method Applicable to the Search for Similarities in the Amino Acid Sequnce of Two Proteins," J. Mol. Biol. 48:443.

Pearson and Lipman (1988) "Improved tools for biological sequence comparison," Proc. Natl. Acad. Sci. USA 85:2444.

Anderson and Young, Quantitative Filter Hybridization, in *Nucleic Acid Hybridization* (1985).

Kacian et al. (1972) "A Replicating RNA Molecule Suitable for a Detailed Analysis of Extracellular Evolution and Replication," Proc. Natl. Acad. Sci. USA 69:3038.

Chamberlin et al. (1970) "New RNA Polymerase from *Escherichia coli* infected with Bacteriophage T7," Nature 228:227.

Wu and Wallace (1989) "The Ligation Amplification Reaction (LAR)—Amplfication of Specific DNA Sequences Using Sequential Rounds of Template–Dependent Ligation," Genomics 4:560.

Erlich (ed.), PCR Technology, Stockton Press (1989).

Sambrook et al., Molecular Cloning: A Laboratory Manual, Cold Spring Harbor Press, NY, pp 9.31–9.58 (1989).

Sambrook, J. et al., Molecular Cloning: A Laboratory Manual, Cold Spring Harbor Press, NY, pp 7.39–7.52 (1989).

Brinster et al. (1985) "Factors affecting the efficiency of introducing foreign DNA into mice by microinjecting eggs," Proc. Natl. Acad. Sci. USA 82:4438–4442.

Hogan et al., in Manipulating the Mouse Embryo, Cold Spring Harbor Laboratory Press, Cold Spring Harbor, N.Y. (1986).

Jahner et al. (1985) "Insertion of the bacterial gpt gene into the germ line of mice by retroviral infection," Proc. Natl. Acad Sci. USA 82:6927–693.

Stewart et al. (1987) "Expression of retroviral vectors in transgenic mice obtained by embryo infection," EMBO J. 6:383–388.

Jahner et al. (1982) "De novo methylation and expression of retroviral genomes during mouse embryogenesis," Nature 298:623–628.

Haskell and Bowen (1995) "Efficient Production of Transgenic Cattle by Retroviral Infection of Early Embryos," Mol. Reprod. Dev. 40:386.

Evans et al. (1981) "Establishment in culture of pluripotential cells from mouse embryos," Nature 292:154–156.

Bradley et al. (1984) "Formation of germ–line chimaeras from embryo–derived teratocarcinoma cells lines," Nature 309:255–258.

Gossler et al. (1986) "Transgenesis by means of blastocyst–derived embryonic stem cell lines," Proc. Acad. Sci. USA 83:9065–9069.

Robertson et al. (1986) "Germ–line transmission of genes introduced into cultured pluripotential cells by retroviral vector," Nature 322:445–448.

Jaenisch (1988) "Transgenic Animals," Science 240:1468–1474.

Graham and van der Eb (1973) "A New Technique for the Assay of Infectivity of Human Adenovirus 5 DNA," Virol. 52:456.

Sambrook, J. et al., Molecular Cloning: A Laboratory Manual, 2nd ed., Cold Spring Harbor Laboratory Press, New York (1989) pp. 16.9–16.15.

Danoff et al. (1987) "Adenocortical Micronodular Dysplasia, Cardiac Myxomas, Lentgines, and Spindle Cell Tumors," Arch. Intern. Med. 147:443–448.

Stratakis et al. (1999) "Genetic Heterogeneity in Carney Complex (OMIM 160980): Contributions of loci at chromosomes 2 and 17 in its genetics," Am. J. Hum. Genet. 65:A447.

Stratakis et al. (1996) "Cytogenetic and Microsatellite Alterations in Tumors from Patients with the Syndrome of Myxomas, Spotty Skin Pigmentation, and Endocrine Overactivity (Carney Complex)," J. Clin. Endocrinol. Metab. 81:3607–3614.

Stratakis et al. (1998) "Carney Complex, Peutz–Jeghers Syndrome, Cowden Disease, and Bannayan–Zonana Syndrome Share Cutaneous and Endocrine Manifestations, But Not Genetic Loci," J. Clin. Endocrinol. Metab., 83:2972–2976.

Solberg et al. (1997) "The Human Gene for the Regulatory Subunit RIα of Cyclic Adenosine 3',5'–Monophosphate–Dependent Protein Kinase: Two Distinct Promoters Provide Differential Regulation of Alternately Spliced Messenger Ribonucleic Acids," Endocrinol. 138: 169–181.

Taymans et al. (1999) "Radiation Hybrid Mapping of Chromosomal Region 2p15–p16: Integration of Expressed and Polymorphic Sequence Maps at the Carney Complex (CNC) and Doyne Honeycomb Retinal Dystrophy (DHRD) Loci," Genomics 56; 344–349.

Gyapay et al. (1996) "A radiation hybrid map of the human genome," Hum. Mol. Genet. 5:339–346.

Lathrop et al. (1984) "Strategies for multilocus linkage analysis in humans," Proc. Natl. Acad. Sci. USA 81:3443–3446.

Sandberg et al. (1987) "Molecular Cloning, cDNA Structure and Deduced Amino Acid Sequence for a Type I Regulatory Subunit of cAMP–Dependent Protein Kinase from Human Testis," Biochem. Biophys. Res. Commun. 149:939–945.

Breathnach and Chambon (1981) "Organization and Expression of Eucaryotic Split Genes Coding for Proteins,"Ann. Rev. Biochem. 50:349–383.

Kirschner et al. (1999) "Genomic Mapping of chromosomal Region 2p15–p21 (D2S378–D2S391): Integration of Genemap'98 within a Framework of Yeast and Bacterial Artificial Chromosomes," Genomics 62:21–33.

O'Donovan et al. (1998) "Blind Analysis of Denaturing High–Performance Liquid Chromatography as a Tool for Mutation Detection," Genomics 52:44–49.

Jones et al. (1999) "Optimal Temperature Selection for Mutation Detection by Denaturing HPLC and Comparison to Single–Stranded Conformation Polymorphism and Heteroduplex Analysis," Clin. Chem., 45:1133–1140.

Kuo et al. (1970) "Cyclic Nucleotide–Dependent Protein Kinases," Biochem. Biophys. Acta 212:79–91.

Kirschner et al. (2000) "Genetic heterogeneity and spectrum of mutations of the PRKARIA gene in patients with the Carney complex," Hum. Mol. Genetics 9:3037–3046.

Kirschner et al. (2000) "Mutations of the gene encoding the protein kinase A type 1–α regulatory subunit in patients with the Carney complex," Nat. Genet. 26:89–92.

Tarutani et al. (1997) "to Tissue–specific knockout of the mouse Pig–a gene revelas important roles for GPI–anchored proteins in skin development," Natl. Acad. Sci. USA 94:7400–7405.

Cho–Chung et al. (1999) "Antisense DNA–Targeting Protein Kinase A–RIA Subunit: A Novel Approach to Cancer Treatment," Frontiers in Biosci. 4:d898–907.

* cited by examiner

A

B

SEQUENCE LISTING

<160> NUMBER OF SEQ ID NOS: 66

<210> SEQ ID NO 1
<211> LENGTH: 20
<212> TYPE: DNA
<213> ORGANISM: Artificial Sequence
<220> FEATURE:

```
<223> OTHER INFORMATION: Synthetic

<400> SEQUENCE: 1
cccccactgt actgaacacc                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
catggccaca cagctaacat                                                   20

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
agtcgcccac ctgtcatct                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cacttctcct ttccgcagtc                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cattgacgtc agtagccgaa                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
atcttggatc ggtccagctc                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cctagtcccc acttccctgt                                                   20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atcacctcat catctcccca                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
catgccgaag gatctcattt                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
atggatgaag ttccaccctg                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
caggttgcaa acgtgaaatg                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ctgcgataaa ggagaccgaa                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
agccaaagcc attgaaaaga                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic

```
<400> SEQUENCE: 14
gcctcctctc ccgtaacaat                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ttgcttgatt ttctttcccc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
attcttattg ctcggaagcg                                              20

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
tcatttaact cgtcagaaat cacc                                         24

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
ttctaaatca cactctcaaa cacca                                        25

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ggcataatat tggcggaaaa                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
aaggcttttc ccaagtccat                                              20

<210> SEQ ID NO 21
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 21
agaatgttga atgggcatgg                                                    20

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ttagcccact ctttccctct t                                                  21

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
caccctgggt ttgagagtgt                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
ttccctctca gagccaaaaa                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cccatctttg ctttctccag                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
aacagacagg aagctgcgat                                                    20

<210> SEQ ID NO 27
<211> LENGTH: 189
<212> TYPE: DNA
<213> ORGANISM: Artificial Sequence
<220> FEATURE:
<223> OTHER INFORMATION: Synthetic

<400> SEQUENCE: 27
```

```
cagagaacca tggagtctgg cagtaccgcc gccagtgagg aggcacgcag ccttcgaaga      60
tgtgagctct acgtccagaa gcataacatt caagcgctgc tcaaagattc tattgtgcag     120
ttgtgcactg ctcgacctga gagacccatg cattcctca gggaatactt tgagaggttg      180
gagaaggta                                                              189
```

```
<210> SEQ ID NO 28
<211> LENGTH: 59
<212> TYPE: PRT
<213> ORGANISM: Artificial Sequence
<220> FEATURE:
<223> OTHER INFORMATION: Synthetic

<400> SEQUENCE: 28

Met Glu Ser Gly Ser Thr Ala Ala Ser Glu Glu Arg Ser Leu Arg
1               5                  10                  15

Glu Cys Glu Leu Tyr Val Gln Lys His Asn Ile Gln Ala Leu Leu Lys
            20                  25                  30

Asp Ser Ile Val Gln Leu Cys Thr Ala Arg Pro Glu Arg Pro Met Ala
        35                  40                  45

Phe Leu Arg Glu Tyr Phe Glu Arg Leu Glu Lys
    50                  55
```

```
<210> SEQ ID NO 29
<211> LENGTH: 189
<212> TYPE: DNA
<213> ORGANISM: Artificial Sequence
<220> FEATURE:
<223> OTHER INFORMATION: Synthetic

<400> SEQUENCE: 29
cggagaacca tggagtctgg cagtaccgcc gccagtgagg aggcacgcag ccttcgaaga      60
tgtgagctct acgtccagaa gcataacatt caagcgctgc tcaaagattc tattgtgcag    120
ttgtgcactg ctcgacctga gagacccatg cattcctca gggaatactt tgagaggttg     180
gagaaggta                                                              189
```

```
<210> SEQ ID NO 30
<211> LENGTH: 189
<212> TYPE: DNA
<213> ORGANISM: Artificial Sequence
<220> FEATURE:
<223> OTHER INFORMATION: Synthetic

<400> SEQUENCE: 30
cagagaaccg tggagtctgg cagtaccgcc gccagtgagg aggcacgcag ccttcgaaga      60
tgtgagctct acgtccagaa gcataacatt caagcgctgc tcaaagattc tattgtgcag    120
ttgtgcactg ctcgacctga gagacccatg cattcctca gggaatactt tgagaggttg     180
gagaaggta                                                              189
```

```
<210> SEQ ID NO 31
<211> LENGTH: 189
<212> TYPE: DNA
<213> ORGANISM: Artificial Sequence
<220> FEATURE:
<223> OTHER INFORMATION: Synthetic

<400> SEQUENCE: 31
cagagaacca tggagtctgg cagtaccgcc gccagtgagg aggcacgcag ccttcgaaga      60
tgtgagctct acgtccagaa gcataacatt taagcgctgc tcaaagattc tattgtgcag    120
ttgtgcactg ctcgacctga gagacccatg cattcctca gggaatactt tgagaggttg     180
```

```
gagaaggta                                                                  189

<210> SEQ ID NO 32
<211> LENGTH: 184
<212> TYPE: DNA
<213> ORGANISM: Artificial Sequence
<220> FEATURE:
<223> OTHER INFORMATION: Synthetic

<400> SEQUENCE: 32
cagagaacca tggagtctgg cagtaccgcc gccagtgagg aggcacgcag ccttcgaaga    60
tgtgagctct acgtccagaa gcataacatt caagcgctgc tcaaagattg tgcagttgtg   120
cactgctcga cctgagagac ccatggcatt cctcagggaa tactttgaga ggttggagaa   180
ggta                                                                 184

<210> SEQ ID NO 33
<211> LENGTH: 189
<212> TYPE: DNA
<213> ORGANISM: Artificial Sequence
<220> FEATURE:
<223> OTHER INFORMATION: Synthetic

<400> SEQUENCE: 33
cagagaacca tggagtctgg cagtaccgcc gccagtgagg aggcacgcag ccttcgaaga    60
tgtgagctct acgtccagaa gcataacatt caagcgctgc tcaaagattc tattgtgcag   120
ttgtgcactg cttgacctga gacccatg gcattcctca gggaatactt tgagaggttg    180
gagaaggta                                                            189

<210> SEQ ID NO 34
<211> LENGTH: 180
<212> TYPE: DNA
<213> ORGANISM: Artificial Sequence
<220> FEATURE:
<223> OTHER INFORMATION: Synthetic

<400> SEQUENCE: 34
caggaggagg caaaacagat tcagaatctg cagaaagcag gcactcgtac agactcaagg    60
gaggatgaga tttctcctcc tccacccaac ccagtggtta aggtaggag gcgacgaggt   120 gctatcagcg ctgaggtcta cacggaggaa gatgcggcat cctatgttag aaaggtagtt   180

<210> SEQ ID NO 35
<211> LENGTH: 57
<212> TYPE: PRT
<213> ORGANISM: Artificial Sequence
<220> FEATURE:
<223> OTHER INFORMATION: Synthetic

<400> SEQUENCE: 35

Glu Glu Ala Lys Gln Ile Gln Asn Leu Gln Lys Ala Gly Thr Arg Thr
1               5                   10                  15

Asp Ser Arg Glu Asp Glu Ile Ser Pro Pro Pro Asn Pro Val Val
            20                  25                  30

Lys Gly Arg Arg Arg Arg Gly Ala Ile Ser Ala Glu Val Tyr Thr Glu
        35                  40                  45

Glu Asp Ala Ala Ser Tyr Val Arg Lys
    50                  55

<210> SEQ ID NO 36
<211> LENGTH: 180
```

<212> TYPE: DNA
<213> ORGANISM: Artificial Sequence
<220> FEATURE:
<223> OTHER INFORMATION: Synthetic

<400> SEQUENCE: 36

```
caggaggagg caaaacagat tcagaatctg cagaaagcag gcactcgtac agactcaagg      60
gaggatgaga tttctcctcc tccacccaac ccagtggtta aggtaggag gcgacgaggt      120 gctatcagcg ctgaggtcta cacggaggaa gatgcggcat cctatgttag aaagctagtt    180
```

<210> SEQ ID NO 37
<211> LENGTH: 100
<212> TYPE: DNA
<213> ORGANISM: Artificial Sequence
<220> FEATURE:
<223> OTHER INFORMATION: Synthetic

<400> SEQUENCE: 37

```
aggttatacc aaaagattac aagacaatgg ccgctttagc caaagccatt gaaaagaatg     60
tgctgttttc acatcttgat gataatgaga gaggtagga                           100
```

<210> SEQ ID NO 38
<211> LENGTH: 31
<212> TYPE: PRT
<213> ORGANISM: Artificial Sequence
<220> FEATURE:
<223> OTHER INFORMATION: Synthetic

<400> SEQUENCE: 38

```
Val Ile Pro Lys Asp Tyr Lys Thr Met Ala Ala Leu Ala Lys Ala Ile
1               5                   10                  15

Glu Lys Asn Val Leu Phe Ser His Leu Asp Asp Asn Glu Arg Ser
            20                  25                  30
```

<210> SEQ ID NO 39
<211> LENGTH: 70
<212> TYPE: DNA
<213> ORGANISM: Artificial Sequence
<220> FEATURE:
<223> OTHER INFORMATION: Synthetic

<400> SEQUENCE: 39

```
cagtgatatt tttgatgcca tgttttcggt ctcctttatc gcaggagaga ctgtgattca      60
gcaaggtaag                                                            70
```

<210> SEQ ID NO 40
<211> LENGTH: 21
<212> TYPE: PRT
<213> ORGANISM: Artificial Sequence
<220> FEATURE:
<223> OTHER INFORMATION: Synthetic

<400> SEQUENCE: 40

```
Asp Ile Phe Asp Ala Met Phe Ser Val Ser Phe Ile Ala Gly Glu Thr
1               5                   10                  15

Val Ile Gln Gln Gly
            20
```

<210> SEQ ID NO 41
<211> LENGTH: 68
<212> TYPE: DNA
<213> ORGANISM: Artificial Sequence
<220> FEATURE:

<210> SEQ ID NO 41
<211> LENGTH: (not shown)
<212> TYPE: DNA
<213> ORGANISM: Artificial Sequence
<220> FEATURE:
<223> OTHER INFORMATION: Synthetic

<400> SEQUENCE: 41

```
cagtgatatt tttgatgcca tgttttcggt ctcctttatc gcaggagaga ctgattcagc    60
aaggtaag                                                              68
```

<210> SEQ ID NO 42
<211> LENGTH: 60
<212> TYPE: DNA
<213> ORGANISM: Artificial Sequence
<220> FEATURE:
<223> OTHER INFORMATION: Synthetic

<400> SEQUENCE: 42

```
ctcttttagg tgatgaaggg gataacttct atgtgattga tcaaggagag acggatgtaa    60
```

<210> SEQ ID NO 43
<211> LENGTH: 15
<212> TYPE: PRT
<213> ORGANISM: Artificial Sequence
<220> FEATURE:
<223> OTHER INFORMATION: Synthetic

<400> SEQUENCE: 43

Asp Glu Gly Asp Asn Phe Tyr Val Ile Asp Gln Gly Glu Thr Asp
1               5                   10                  15

<210> SEQ ID NO 44
<211> LENGTH: 56
<212> TYPE: DNA
<213> ORGANISM: Artificial Sequence
<220> FEATURE:
<223> OTHER INFORMATION: Synthetic

<400> SEQUENCE: 44

```
ctcttttagg tgatgaaggg gataacttct atgtgatcaa ggagagacgg atgtaa        56
```

<210> SEQ ID NO 45
<211> LENGTH: 183
<212> TYPE: DNA
<213> ORGANISM: Artificial Sequence
<220> FEATURE:
<223> OTHER INFORMATION: Synthetic

<400> SEQUENCE: 45

```
ttgatgtcac ttgcacttta ggtctatgtt aacaatgaat gggcaaccag tgttggggaa    60
ggagggagct ttggagaact tgctttgatt tatggaacac cgagagcagc cactgtcaaa   120
gcaaagacaa atgtgaaatt gtggggcatc gaccgagaca gctatagaag aatcctcatg   180
gta                                                                 183
```

<210> SEQ ID NO 46
<211> LENGTH: 53
<212> TYPE: PRT
<213> ORGANISM: Artificial Sequence
<220> FEATURE:
<223> OTHER INFORMATION: Synthetic

<400> SEQUENCE: 46

Val Tyr Val Asn Asn Glu Trp Ala Thr Ser Val Gly Glu Gly Gly Ser
1               5                   10                  15

Phe Gly Glu Leu Ala Leu Ile Tyr Gly Thr Pro Arg Ala Ala Thr Val
            20                  25                  30

```
Lys Ala Lys Thr Asn Val Lys Leu Trp Gly Ile Asp Arg Asp Ser Tyr
        35                  40                  45
Arg Arg Ile Leu Met
    50

<210> SEQ ID NO 47
<211> LENGTH: 175
<212> TYPE: DNA
<213> ORGANISM: Artificial Sequence
<220> FEATURE:
<223> OTHER INFORMATION: Synthetic

<400> SEQUENCE: 47
ttgatgtcac ttggtctatg ttaacaatga atgggcaacc agtgttgggg aaggagggag      60
ctttggagaa cttgctttga tttatggaac accgagagca gccactgtca aagcaaagac     120
aaatgtgaaa ttgtggggca tcgaccgaga cagctataga agaatcctca tggta          175

<210> SEQ ID NO 48
<211> LENGTH: 184
<212> TYPE: DNA
<213> ORGANISM: Artificial Sequence
<220> FEATURE:
<223> OTHER INFORMATION: Synthetic

<400> SEQUENCE: 48
ttgatgtcac ttgcacttta ggtctatgtt aaccactgaa tgggcaacca gtgttgggga      60
aggagggagc tttggagaac ttgctttgat ttatggaaca ccgagagcag ccactgtcaa     120
agcaaagaca aatgtgaaat gtggggcat cgaccgagac agctatagaa gaatcctcat     180
ggta                                                                  184

<210> SEQ ID NO 49
<211> LENGTH: 183
<212> TYPE: DNA
<213> ORGANISM: Artificial Sequence
<220> FEATURE:
<223> OTHER INFORMATION: Synthetic

<400> SEQUENCE: 49
ttgatgtcac ttgcacttta ggtctatgtt aacaatgaat gggcaaccag tgttggggaa      60
ggagggagct ttggagaact tgctttgatt tatggaacac cgagagcagc cactgtcaaa     120
gcaaagacaa atgtgaaatt gtgggcatc gactgagaca gctatagaag aatcctcatg     180
gta                                                                   183

<210> SEQ ID NO 50
<211> LENGTH: 184
<212> TYPE: DNA
<213> ORGANISM: Artificial Sequence
<220> FEATURE:
<223> OTHER INFORMATION: Synthetic

<400> SEQUENCE: 50
ttgatgtcac ttgcacttta ggtctatgtt aacaatgaat gggcaaccag tgttggggaa      60
ggagggagct ttggagaact tgctttgatt tatggaacac cgagagcagc cactgtcaaa     120
gcaaagacaa atgtgaaatt gtgggcatc gaccgagaca gctattagaa gaatcctcat     180
ggta                                                                  184

<210> SEQ ID NO 51
<211> LENGTH: 80
```

<212> TYPE: DNA
<213> ORGANISM: Artificial Sequence
<220> FEATURE:
<223> OTHER INFORMATION: Synthetic

<400> SEQUENCE: 51 tattttagg gaagcacact gagaaagcgg aagatgtatg aggaattcct tagtaaagtc    60
tctattttag gtgagttgta                                              80

<210> SEQ ID NO 52
<211> LENGTH: 21
<212> TYPE: PRT
<213> ORGANISM: Artificial Sequence
<220> FEATURE:
<223> OTHER INFORMATION: Synthetic

<400> SEQUENCE: 52

Gly Ser Thr Leu Arg Lys Arg Lys Met Tyr Glu Glu Phe Leu Ser Lys
1               5                   10                  15

Val Ser Ile Leu Glu
            20

<210> SEQ ID NO 53
<211> LENGTH: 82
<212> TYPE: DNA
<213> ORGANISM: Artificial Sequence
<220> FEATURE:
<223> OTHER INFORMATION: Synthetic

<400> SEQUENCE: 53 tattttagg gaaaagcaca ctgagaaagc ggaagatgta tgaggaattc cttagtaaag    60
tctctatttt aggtgagttg ta                                           82

<210> SEQ ID NO 54
<211> LENGTH: 140
<212> TYPE: DNA
<213> ORGANISM: Artificial Sequence
<220> FEATURE:
<223> OTHER INFORMATION: Synthetic

<400> SEQUENCE: 54
gtctttcaga gtctctggac aagtgggaac gtcttacggt agctgatgca ttggaaccag    60
tgcagtttga agatgggcag aagattgtgg tgcagggaga accaggggat gagttcttca   120
ttattttaga ggtaaagaac                                              140

<210> SEQ ID NO 55
<211> LENGTH: 40
<212> TYPE: PRT
<213> ORGANISM: Artificial Sequence
<220> FEATURE:
<223> OTHER INFORMATION: Synthetic

<400> SEQUENCE: 55

Ser Leu Asp Lys Trp Glu Arg Leu Thr Val Ala Asp Ala Leu Glu Pro
1               5                   10                  15

Val Gln Phe Glu Asp Gly Gln Lys Ile Val Val Gln Gly Glu Pro Gly
            20                  25                  30

Asp Glu Phe Phe Ile Ile Leu Glu
            35                  40

<210> SEQ ID NO 56
<211> LENGTH: 140

<212> TYPE: DNA
<213> ORGANISM: Artificial Sequence
<220> FEATURE:
<223> OTHER INFORMATION: Synthetic

<400> SEQUENCE: 56
gtctttcaga gtctctggac aagtgctaac gtcttacggt agctgatgca ttggaaccag     60
tgcagtttga agatgggcag aagattgtgg tgcaggagag accaggggat gagttcttca    120
ttattttaga ggtgaagaac                                                140

<210> SEQ ID NO 57
<211> LENGTH: 140
<212> TYPE: DNA
<213> ORGANISM: Artificial Sequence
<220> FEATURE:
<223> OTHER INFORMATION: Synthetic

<400> SEQUENCE: 57
gtctttcaga gtctctggac aagtgggaac gtcttacggt agctgatgca ttggaaccag     60
tgcagtttga agatgggcag aagattgtgg tgcaggagag accaggggat gagttcttca    120
ttattttaga ggtaaagaac                                                140

<210> SEQ ID NO 58
<211> LENGTH: 100
<212> TYPE: DNA
<213> ORGANISM: Artificial Sequence
<220> FEATURE:
<223> OTHER INFORMATION: Synthetic

<400> SEQUENCE: 58
ttattatagg ggtcagctgc tgtgctacaa cgtcggtcag aaaatgaaga gtttgttgaa     60
gtgggaagat tggggccttc tgattatttt ggtatgtatg                          100

<210> SEQ ID NO 59
<211> LENGTH: 27
<212> TYPE: PRT
<213> ORGANISM: Artificial Sequence
<220> FEATURE:
<223> OTHER INFORMATION: Synthetic

<400> SEQUENCE: 59

Gly Ser Ala Ala Val Leu Gln Arg Arg Ser Glu Asn Glu Glu Phe Val
1               5                   10                  15

Glu Val Gly Arg Leu Gly Pro Ser Asp Tyr Phe
            20                  25

<210> SEQ ID NO 60
<211> LENGTH: 100
<212> TYPE: DNA
<213> ORGANISM: Artificial Sequence
<220> FEATURE:
<223> OTHER INFORMATION: Synthetic

<400> SEQUENCE: 60
ttattatagg ggtcagctgc tgtgctacaa cgtcggtgag aaaatgaaga gtttgttgaa     60
gtgggaagat tggggccttc tgattatttt ggtatgtatg                          100

<210> SEQ ID NO 61
<211> LENGTH: 377
<212> TYPE: DNA
<213> ORGANISM: Artificial Sequence
<220> FEATURE:

<223> OTHER INFORMATION: Synthetic

<400> SEQUENCE: 61

| | |
|---|---|
| ctccaggtga aattgcacta ctgatgaatc gtcctcgtgc tgccacagtt gttgctcgtg | 60 |
| gccccttgaa gtgcgttaag ctggaccgac ctagatttga acgtgttctt ggcccatgct | 120 |
| cagacatcct caaacgaaac atccagcagt acaacagttt tgtgtcactg tctgtctgaa | 180 |
| atctgcctcc tgtgcctccc ttttctcctc tccccaatcc atgcttcact catgcaaact | 240 |
| gctttatttt ccctacttgc agcgccaagt ggccactggc atcgcagctt cctgtctgtt | 300 |
| tatatattga agttgctttt tattgcacca ttttcaattt ggagcattaa ctaaatgctc | 360 |
| atacacagtt aaataaa | 377 |

<210> SEQ ID NO 62
<211> LENGTH: 57
<212> TYPE: PRT
<213> ORGANISM: Artificial Sequence
<220> FEATURE:
<223> OTHER INFORMATION: Synthetic

<400> SEQUENCE: 62

Gly Glu Ile Ala Leu Leu Met Asn Arg Pro Arg Ala Ala Thr Val Val
1               5                   10                  15

Ala Arg Gly Pro Leu Lys Cys Val Lys Leu Asp Arg Pro Arg Phe Glu
            20                  25                  30

Arg Val Leu Gly Pro Cys Ser Asp Ile Leu Lys Arg Asn Ile Gln Gln
        35                  40                  45

Tyr Asn Ser Phe Val Ser Leu Ser Val
    50                  55

<210> SEQ ID NO 63
<211> LENGTH: 49
<212> TYPE: DNA
<213> ORGANISM: Artificial Sequence
<220> FEATURE:
<223> OTHER INFORMATION: Synthetic

<400> SEQUENCE: 63

| | |
|---|---|
| ggggacaagt ttgtacaaaa aagcaggctg tccccagaga accatggag | 49 |

<210> SEQ ID NO 64
<211> LENGTH: 49
<212> TYPE: DNA
<213> ORGANISM: Artificial Sequence
<220> FEATURE:
<223> OTHER INFORMATION: Synthetic

<400> SEQUENCE: 64

| | |
|---|---|
| ggggaccact ttgtacaaga aagctgggtc agtctctcct gcgataaag | 49 |

<210> SEQ ID NO 65
<211> LENGTH: 49
<212> TYPE: DNA
<213> ORGANISM: Artificial Sequence
<220> FEATURE:
<223> OTHER INFORMATION: Synthetic

<400> SEQUENCE: 65

| | |
|---|---|
| ggggaccact ttgtacaaga aagctgggta cttgtccaga gactctaaa | 49 |

<210> SEQ ID NO 66
<211> LENGTH: 49

-continued

```
<212> TYPE: DNA
<213> ORGANISM: Artificial Sequence
<220> FEATURE:
<223> OTHER INFORMATION: Synthetic

<400> SEQUENCE: 66
ggggaccact ttgtacaaga aagctgggtc agacagtgac acaaaactg            49
```

PROTEIN KINASE A AND CARNEY COMPLEX

The present application claims priority to U.S. Provisional Patent Application Serial No. 60/228,211, filed on Aug. 25, 2000.

This invention was made with government support to the intramural research project Z01-HD-00642-1 DEB of the National Institute of Child Health & Human Development (NICHD), of the National Institutes of Health. The United States Government has certain rights in the invention.

FIELD OF THE INVENTION

The present invention provides compositions and methods useful in the diagnosis and prognosis of Carney complex (CNC), as well as methods and compositions for the identification of compounds useful in the treatment and/or prevention of CNC. In addition, the present invention provides compositions and methods useful in the diagnosis and treatment of conditions associated with skin pigmentation defects, including but not limited to freckling, as well as endocrine tumors including, but not limited to adrenal and pituitary tumors. In addition, the present invention provides methods and compositions for the diagnosis and treatment of various types of cancers associated with abnormal activity of protein kinase A. In particular, the present invention provides genetic and other sequence information, as well as assay systems that will find use in these and related areas.

BACKGROUND OF THE INVENTION

Carney complex (CNC) is a multiple endocrine neoplasia (MEN) syndrome that affects the adrenal cortex, pituitary gland, thyroid gland, and the gonads. It is also associated with skin and mucosa pigmentation abnormalities, as well as myxoid and other neoplasms of mesenchymal and neural crest origin. The syndrome is characterized by spotty skin pigmentation, cardiac and other myxomas, endocrine tumors, and psammomatous melanotic schwannomas (Carney and Young, Endocrinologist 2:6–21 [1992]; Carney, Semin. Dermatol., 14:90–98 [1995]; Stratakis et al., Am. J. Med. Genet., 80:183–185 [1998]; Carney et al., Mayo Clin. Proc., 61:165–172 [1985]; and Stratakis, Front. Biosci., 5:D353–366 [2000]). The syndrome also belongs to another group of genetic disorders, referred to as the "lentiginoses" (lentigenoses), which also includes Peutz-Jeghers, LEOPARD, arterial dissections and lentiginosis, Laugier-Hunziker syndrome, Cowden disease, and Ruvalcaba-Myhre-Smith (Bannayan-Zonana) syndrome, and the centrofacial, benign patterned and segmental lentiginoses, all of which have been associated with a variety of developmental defects. The components of the complex have previously been described by the acronyms NAME (nevi, atrial myxomas and ephelides) or LAMB (lentigines, atrial myxomas, and blue nevi) (See e.g., Atherton et al., Br. J. Dermatol., 103:421–429 [1980]; and Rhodes et al., J. Am. Acad. Dermatol., 10,72–82 [1984]). However, it is presently accepted that most, if not all, of these patients had Carney complex (Stratakis, Pediatr. Pathol. Mol. Med., 19:41–68 [2000]).

Although it is relatively rare, the impact of the syndrome on affected patients is significant. As with other multiple neoplasias and lentigenosis syndromes, Carney complex affects many organs and systems. Typically, patients simultaneously have at least two endocrine tumors (e.g., primary pigmented nodular adrenocortical disease [PPNAD], growth hormone and/or prolactin-producing pituitary adenomas, thyroid nodules or carcinomas, testicular neoplasms [primarily large cell calcifying Sertoli cell tumor (LCCSCT)], and ovarian cysts), as well as psammomatous melanotic schwannoma (PMS), epithelioid blue nevus, breast ductal adenoma, and osteochondromyxoma (i.e., a rare bone tumor). The lesions are multicentric, often bilateral in paired organs, and originate in cells of mesenchymal (myxomas) or neural crest origin (spotty skin pigmentation and endocrine tumors). Thus, it is contemplated that the genetic defects associated with Carney complex are involved in the early development, growth, and proliferation of affected cells.

Early reports suggested that Carney complex was an inherited disease of immunological origin (Young et al., N. Eng. J. Med., 321:1659–1664 [1989]; and Berkhout et al., Clin. Endocrinol., 31:185–191 [1989]). Later reports indicated no association with autoimmune disease or immune dysfunction in affected patients (See e.g., Stratakis et al., J. Clin. Invest. 97:699–705). More recently, CNC has been reported to be inherited as an autosomal dominant trait and the responsible genes have been mapped to 2p16 and 17q22–24 (Stratakis et al., J. Clin. Invest., 97:699–705 [1996]; and Casey et al., Circul., 98:2560–2566 [1998]). Nonetheless, the genetic defects responsible for the complex remained unknown, making diagnosis and treatment of Carney complex problematic.

Currently, to make a diagnosis of Carney complex, a patient must either exhibit two of the manifestations listed in Table 1 below, or exhibit one of these manifestations and meet one of the supplemental criteria (i.e., an affected first-degree relative or an inactivating mutation of the PRKAR1A gene).

TABLE 1

Manifestations of Carney Complex Used in Diagnosis

Spotty skin pigmentation with a typical distribution (lips, conjunctiva, and inner or outer canthi, vaginal and penile mucosa)
Myxoma (cutaneous and mucosal), (with histologic confirmation)
Cardia myxoma
Breast myxomatosis or fat-suppressed magnetic resonance imaging findings suggestive of this diagnosis (with histologic confirmation)
PPNAD (with histologic confirmation) or paradoxical positive response of urinary glucocorticosteroids to dexamethasone administration during Liddle's test
Acromegaly due to growth hormone-producing adenoma
LCCSCT (with histologic confirmation) or characteristic calcification on testicular ultrasonography
Thyroid carcinoma (with histologic confirmation) or multiple, hypoechoic nodules on thyroid ultrasonography
Psammomatous melanotic schwannoma (with histologic confirmation)
Blue nevus, epithelioid blue nevus (multiple) (with histologic confirmation)
Breast ductal adenoma (multiple)
Osteochondromyxoma (with histologic confirmation)

Additional findings that are suggestive or possibly associated with Carney complex, but are not diagnostic for the disease include: (1) intense freckling (without darkly pigmented spots or typical distribution); (2) blue nevus, usual type (if multiple); (3) café-au-lait spots or other "birthmarks"; (4) elevated IGF-1 levels, abnormal oGTT, or paradoxical growth hormone responses to TRH testing, in the absence of clinical acromegaly; (5) cardiomyopathy; (6) pilonidal sinus; (7) history of Cushing syndrome, acromegaly, or sudden death in extended family; (8) multiple skin tags and other skin lesions; lipomas; (9) colonic polyps (usually in association with acromegaly); (10) hyperprolactinemia (usually mild and almost always in association with clinical or subclinical acromegaly); (11) single, benign thyroid nodule in a young patient or multiple thyroid nodules in an older patient (detected by ultrasonography); and (12) family history of carcinoma, in particular of the thyroid, colon, pancreas, and the ovary, or other multiple benign or malignant tumors.

Once the above diagnostic criteria have been applied, and a diagnosis has been confirmed, for post-pubertal pediatric and adult patients, the recommended clinical surveillance of patients with Carney complex involves: echocardiograms (annually or biannually for adolescent patients with a history of excised myxoma), testicular ultrasound (annually), thyroid ultrasound (baseline examination; it may be repeated, as needed), transabdominal ultrasound of the ovaries (baseline examination; it may be repeated, as needed); urinary free cortisol levels (annually); and serum IGF-1 levels (annually). For pre-pubertal pediatric Carney complex patients, the recommended clinical surveillance typically involves echocardiograms (annually; biannually for patients with a history of excised myxoma), testicular ultrasound for boys, and close monitoring of growth rate and pubertal staging (annually). In addition to monitoring of urinary free cortisol levels, further evaluation of patients with primary pigmented nodular adrenocortical disease (all age groups) includes monitoring of diurnal cortisol levels (11:30 PM, 12:00 MN, 7:30 AM, and 8:00 AM sampling), dexamethasone-stimulation test (modified Liddle's test; See, Stratakis et al., Ann. Intern. Med., 131:585–591 [1999]), and adrenal computed tomography. In addition to monitoring of serum IGF-1 levels, further evaluation of Carney complex patients with gigantism/acromegaly (all age groups) includes pituitary magnetic resonance imaging, 3 hour glucose tolerance test (oGTT), and 90 minute TRH testing. For Carney complex patients of all ages with psammomatous melanotic schwannoma, further evaluation includes magnetic resonance imaging (brain, spine, chest, abdomen, retroperitoneum, pelvis).

In view of the vagaries associated with the currently used methods of diagnosis and prognosis of Carney complex, there remains a need in the art for methods and compositions for the diagnosis, prognosis, and treatment of Carney complex, as well as for methods and compositions useful in the identification of compounds suitable for the treatment of Carney complex and the symptoms associated with the disease.

SUMMARY OF THE INVENTION

The present invention provides compositions and methods useful in the diagnosis and prognosis of Carney complex (CNC), as well as methods and compositions for the identification of compounds useful in the treatment and/or prevention of CNC. In addition, the present invention provides compositions and methods useful in the diagnosis and treatment of conditions associated with skin pigmentation defects, including but not limited to freckling, as well as endocrine tumors including, but not limited to adrenal and pituitary tumors. In addition, the present invention provides methods and compositions for the diagnosis and treatment of various types of cancers associated with abnormal activity of protein kinase A. In particular, the present invention provides genetic and other sequence information, as well as assay systems that will find use in these and related areas.

The present invention provides compositions comprising various mutations in the PRKAR1A gene. In particular, the present invention provides the sequence of wild-type exon 2 (SEQ ID NO:27), as well as the amino acid sequence of wild-type exon 2 (SEQ ID NO:28). The present invention also provides exon 2 mutants with the sequence of SEQ ID NO:29, as well as mutants with the sequences of SEQ ID NO:30, SEQ ID NO:31, SEQ ID NO:32, and SEQ ID NO:33.

The present invention further provides the sequence of exon 3 (SEQ ID NO:34), as well as the amino acid sequence of wild-type exon 3 (SEQ ID NO:35). The present invention also provides an exon 3 mutant with the sequence of SEQ ID NO:36.

The present invention further provides the sequence of exon 4A (SEQ ID NO:37), as well as the amino acid sequence of wild-type exon 4A (SEQ ID NO:38). The present invention further provides the sequence of exon 4B (SEQ ID NO:39), as well as the amino acid sequence of wild-type exon 4B (SEQ ID NO:40), and an exon 4B mutant (SEQ ID NO:41).

The present invention further provides the sequence of exon 5 (SEQ ID NO:42), as well as the amino acid sequence of wild-type exon 5 (SEQ ID NO:43), and an exon 5 mutant (SEQ ID NO:44).

The present invention also provides the sequence of exon 6 (SEQ ID NO:45), as well as the amino acid sequence of wild-type exon 6 (SEQ ID NO:46). The present invention further provides exon 6 mutants, with the sequences SEQ ID NO:47, SEQ ID NO:48, SEQ ID NO:49, and SEQ ID NO:50.

The present invention further provides the sequence of exon 7 (SEQ ID NO:51), as well as the amino acid sequence of exon 7 (SEQ ID NO:52), and an exon 7 mutant (SEQ ID NO:53).

The present invention also provides the sequence of wild-type exon 8 (SEQ ID NO:54), as well as the amino acid sequence of wild-type exon 8 (SEQ ID NO:55). The present invention also provides exon 8 mutants with the sequences of SEQ ID NO:56, and SEQ ID NO:57.

The present invention further provides the sequence of wild-type exon 9 (SEQ ID NO:58), as well as the amino acid sequence of exon 9 (SEQ ID NO:59), and an exon 9 mutant (SEQ ID NO:60).

The present invention also provides the sequence of wild-type exon 10 (SEQ ID NO:61), as well as the amino acid sequence of wild-type exon 10 (SEQ ID NO:62).

In some embodiments, the present invention provides an isolated nucleotide sequence of the wild-type protein kinase regulatory subunit 1A gene, wherein the sequence is selected from the group consisting of SEQ ID NO:27, SEQ ID NO:34, SEQ ID NO:38, SEQ ID NO:40, SEQ ID NO:42, SEQ ID NO:45, SEQ ID NO:51, SEQ ID NO:54, SEQ ID NO:58, and SEQ ID NO:61.

In other embodiments, the present invention provides an isolated amino acid sequence of the wild-type protein kinase regulatory subunit 1A, wherein the sequence is selected from the group consisting of SEQ ID NO:28, SEQ ID NO:35, SEQ ID NO:38, SEQ ID NO:40, SEQ ID NO:43, SEQ ID NO:46, SEQ ID NO:52, SEQ ID NO:55, SEQ ID NO:59, and SEQ ID NO:62.

In further embodiments, the present invention provides a nucleotide sequence of mutant protein kinase regulatory subunit 1A gene, wherein the mutation is selected from the group consisting of SEQ ID NO:29, SEQ ID NO:30, SEQ ID NO:31, SEQ ID NO:32, SEQ ID NO:33, SEQ ID NO:36, SEQ ID NO:41, SEQ ID NO:44, SEQ ID NO:47, SEQ ID NO:48, SEQ ID NO:49, SEQ ID NO:50, SEQ ID NO:53, SEQ ID NO:56, SEQ ID NO:57, and SEQ ID NO:60.

In addition, the present invention provides screening methods for detection of mutations in PKA. In some preferred embodiments, the screening methods include, but are not limited to D-HPLC, sequencing, and cDNA PCR amplification. It is contemplated that these methods will find use either alone or in combination, as well as in combination with other diagnostic and prognostic methods. In particularly preferred embodiments, mutations in the genes encoding R1A are detected using the methods of the present invention. However, it is contemplated that the methods of the present invention will find use in the detection and screening of mutations in the other subunits of PKA.

In alternative embodiments, the present invention provides methods and compositions for the detection and screening of subjects suffering from or suspected of suffering from Carney complex and/or skin pigmentation defects, including but not limited to freckling, as well as endocrine tumors including, but not limited to adrenal and pituitary tumors. In particularly preferred embodiments, these methods include, but are not limited to D-HPLC, sequencing, and cDNA PCR amplification. It is contemplated that these methods will find use either alone or in combination, as well as in combination with other diagnostic and prognostic methods. In particularly preferred embodiments, mutations in the genes encoding R1A are detected using the methods of the present invention. However, it is contemplated that the methods of the present invention will find use in the detection and screening of mutations in the other subunits of PKA.

In other embodiments, present invention provides methods for the detection of mutations in PKA (e.g., for screening and diagnosis) involving restriction digestion of genomic DNA or cDNA obtained from a subject and detection of alterations in the restriction patterns. These alterations in restriction patterns are then correlated with changes in the sequence of the PKA genes. In further embodiments, the samples used in these methods are obtained from subjects who are suffering from or are suspected of suffering from skin pigmentation defects, including but not limited to freckling, as well as endocrine tumors including, but not limited to adrenal and pituitary tumors. It is contemplated that these methods will find use either alone or in combination, as well as in combination with other diagnostic and prognostic methods. In particularly preferred embodiments, mutations in the genes encoding R1A are detected using the methods of the present invention. However, it is contemplated that the methods of the present invention will find use in the detection and screening of mutations in the other subunits of PKA.

In still further embodiments, the present invention provides methods involving cold or hot SSCP. In preferred embodiments, these methods utilize the primers described herein (e.g., SEQ ID NOS:1–26, and 63–66). In further embodiments, samples used in these methods involve samples obtained from subjects that are suffering from or are suspected of suffering from skin pigmentation defects, including but not limited to freckling, as well as endocrine tumors including, but not limited to adrenal and pituitary tumors. It is contemplated that these methods will find use either alone or in combination, as well as in combination with other diagnostic and prognostic methods. In particularly preferred embodiments, mutations in the genes encoding R1A are detected using the methods of the present invention. However, it is contemplated that the methods of the present invention will find use in the detection and screening of mutations in the other subunits of PKA.

The present invention also provides methods and compositions for PCR, in particular quantitative PCR (e.g., Taqman) for determination of the relative expression of PRKAR1A mRNA in tumors and/or cell lines. In further embodiments, the mutant tumors and/or cell lines are obtained from subjects who are suffering from or are suspected of suffering from skin pigmentation defects, including but not limited to freckling, as well as endocrine tumors including, but not limited to adrenal and pituitary tumors. It is contemplated that these methods will find use either alone or in combination, as well as in combination with other diagnostic and prognostic methods. In particularly preferred embodiments, mutations in the genes encoding R1A are detected and analyzed using the methods of the present invention. However, it is contemplated that the methods of the present invention will find use in the detection and screening of mutations in the other subunits of PKA.

In yet other embodiments, the present invention provides protein truncation detection methods which are utilized following expression (e.g., in vitro expression) of cloned mutant PKA DNA. Such protein detection methods are known to those in the art and are suitable for use to detect the truncation mutants of the present invention. In further embodiments, the mutant PKA DNA is obtained from subjects who are suffering from or are suspected of suffering from skin pigmentation defects, including but not limited to freckling, as well as endocrine tumors including, but not limited to adrenal and pituitary tumors. It is contemplated that these methods will find use either alone or in combination, as well as in combination with other diagnostic and prognostic methods. In particularly preferred embodiments, mutations in the genes encoding R1A are detected using the methods of the present invention. However, it is contemplated that the methods of the present invention will find use in the detection and screening of mutations in the other subunits of PKA.

The present invention also provides methods for detecting a nucleic acid encoding a mutant protein kinase regulatory subunit 1A gene, comprising providing a biological sample from a patient suspected of containing a nucleic acid sequence encoding mutant protein kinase regulatory subunit 1A gene, and a polynucleotide sequence comprising at least ten nucleotides capable of hybridizing to the nucleic acid sequence; hybridizing the polynucleotide sequence to the nucleic acid sequence encoding a mutant protein kinase regulatory subunit 1A gene to produce a hybridization complex; and detecting the hybridization complex. In other embodiments the polynucleotide sequence comprises fewer than ten nucleotides, with the number of nucleotides as desired by the user of the method and/or as appropriate for the particular embodiment of the method used.

In some embodiments of these methods, the mutant protein kinase regulatory subunit 1A gene comprises a mutant exon having a nucleotide sequence selected from the group consisting of SEQ ID NO:29, SEQ ID NO:30, SEQ ID NO:31, SEQ ID NO:32, SEQ ID NO:33, SEQ ID NO:36, SEQ ID NO:41, SEQ ID NO:44, SEQ ID NO:47, SEQ ID NO:48, SEQ ID NO:49, SEQ ID NO:50, SEQ ID NO:53, SEQ ID NO:56, SEQ ID NO:57, and SEQ ID NO:60.

In still further embodiments, the methods, further comprise the step of amplifying nucleic acid encoding a mutant protein kinase regulatory subunit 1A gene before the hybridizing step. In some embodiments, amplifying is accomplished using primers selected from the group consisting of SEQ ID NOS:1–26 and SEQ ID NOS:63–66. In additional embodiments, the detecting step comprises the step of detecting the presence of nucleic acid sequence encoding mutant protein kinase regulatory subunit 1A gene. In some embodiments, the detecting is by Northern blotting. In some preferred embodiments, the patient has Carney complex. In some particularly preferred embodiments, the patient is related to at least one individual having Carney complex. In some additional embodiments, the patient exhibits at least one skin pigmentation defect. In still further embodiments, the patient has a least one lesion selected from the group consisting of adrenal tumors, thyroid tumors, pituitary tumors, myxomas, psammomatous melanotic schwannomas and testicular tumors. In other embodiments, the mutant protein kinase regulatory subunit 1A gene is a truncation mutant. In some preferred embodiments, the method further comprises restriction digestion of nucleic acid in the biological sample. In alternative embodiments, the methods further comprise the step of assaying the biological sample from the patient for protein kinase A activity. In still other alternative embodiments, the methods further comprise the step of assaying the biological sample for PK1 inhibition of protein kinase A activity.

The present invention also provides methods for detecting a nucleic acid encoding a mutant protein kinase R1A, comprising the steps of providing: a biological sample from a cell line suspected of containing a nucleic acid sequence encoding mutant protein kinase regulatory subunit 1A gene, and a polynucleotide sequence comprising at least ten nucleotides capable of hybridizing to nucleic acid sequence; hybridizing the polynucleotide sequence to the nucleic acid sequence encoding a mutant protein kinase regulatory subunit 1A gene to produce a hybridization complex; and detecting the hybridization complex. In other embodiments the polynucleotide sequence comprises fewer than ten nucleotides, with the number of nucleotides as desired by the user of the method and/or as appropriate for the particular embodiment of the method used.

In some preferred embodiments, the mutant protein kinase regulatory subunit 1 A gene comprises a mutant exon having a nucleotide sequence selected from the group consisting of SEQ ID NO:29, SEQ ID NO:30, SEQ ID NO:31, SEQ ID NO:32, SEQ ID NO:33, SEQ ID NO:36, SEQ ID NO:41, SEQ ID NO:44, SEQ ID NO:47, SEQ ID NO:48, SEQ ID NO:49, SEQ ID NO:50, SEQ ID NO:53, SEQ ID NO:56, SEQ ID NO:57, and SEQ ID NO:60.

In still other embodiments, the methods further comprise the step of amplifying the nucleic acid encoding a mutant protein kinase regulatory subunit 1A gene before the hybridizing step. In some particularly preferred embodiments, amplifying is accomplished using primers selected from the group consisting of SEQ ID NOS:1–26 and SEQ ID NOS:63–66. In additional embodiments, the detecting step comprises the step of detecting the presence of the nucleic acid sequence encoding the mutant protein kinase regulatory subunit 1A gene. In some preferred embodiments, the detecting is by Northern blotting.

In some embodiments of the methods, the cell line is obtained from a patient with Carney complex. In still other embodiments, the cell line is obtained from a patient who is related to at least one individual having Carney complex. In additional embodiments, the cell line is from a patient who exhibits at least one skin pigmentation defect. In further embodiments, the cell line is from a patient with at least one lesion selected from the group consisting of adrenal tumors, thyroid tumors, pituitary tumors, myxomas, psammomatous melanotic schwannomas and testicular tumors. In some embodiments, the cell line is obtained from at least one or more lesion. In additional embodiments, the mutant protein kinase R1A is a truncation mutant. In still further embodiments, the methods further comprise restriction digestion of the nucleic acid in the biological sample. In some preferred embodiments, the methods further comprise the step of assaying the cell line for protein kinase A activity. In some alternative embodiments, the methods further comprise the step of assaying the cell line for PK1 inhibition of protein kinase A activity.

The present invention also provides antibodies directed against protein kinase regulatory subunit 1A protein. In some preferred embodiments, the antibody is directed against wild-type protein kinase regulatory subunit 1A protein, while in other preferred embodiments, the antibody is directed against mutant protein kinase R1A regulatory subunit 1A gene protein.

The present invention also provides immunohistochemistry methods. In some embodiments, these methods involve the use of antibodies directed against PRKAR1A antibody (e.g., the antibodies used in the Examples below), while other embodiments involve the use of indirect methods (e.g., sandwich type assays). It is contemplated that these methods will find use in the detection of samples in which decreased expression of PRKAR1A is suspected. In further embodiments, samples used in these immunohistochemistry methods are from subjects that are suffering from or are suspected of suffering from skin pigmentation defects, including but not limited to freckling, as well as endocrine tumors including, but not limited to adrenal and pituitary tumors. It is contemplated that these methods will find use either alone or in combination with other diagnostic and prognostic methods. In particularly preferred embodiments, mutant R1As are detected using the methods of the present invention. However, it is contemplated that the methods of the present invention will find use in the detection and screening of mutations in the other subunits of PKA.

The present invention further provides methods for detecting a protein kinase regulatory subunit 1A, comprising: providing a biological sample suspected of containing protein kinase regulatory subunit 1A, and an antibody directed against protein kinase regulatory subunit 1A; exposing the biological sample to the antibody to form a complex comprising protein kinase regulatory subunit 1A bound to the antibody; and detecting the complex.

In some embodiments, the biological sample is from a patient suspected of having Carney complex. In other embodiments, the biological sample is from a patient who is related to at least one individual who has Carney complex.

In some preferred embodiments, the protein kinase regulatory subunit 1A is a mutant protein kinase regulatory subunit 1A. In still further embodiments, the antibody is selected from the group consisting of antibodies directed against wild-type protein kinase regulatory subunit 1A and antibodies directed against mutant protein kinase regulatory subunit 1A. In some preferred embodiments, the method is selected from the group consisting of Western blotting, immunoassays, and immunohistochemistry.

In still further embodiments, the present invention provides screening methods for PKA activity in tumors or cell lines suspected of having at least one PRKAR1A mutation. In some embodiments, the methods comprise cAMP stimulation followed by PKA assay analysis, as well as PK1 inhibition assays of PKA activity. The present invention also provides methods involving the use of Northern blots for detection of mutant PRKAR1A mRNA. However, it is not intended that the present invention be limited to these particular assays, used alone or in combination. In further embodiments, the tumors or cell lines are obtained from subjects who are suffering from or are suspected of suffering from skin pigmentation defects, including but not limited to freckling, as well as endocrine tumors including, but not limited to adrenal and pituitary tumors. It is contemplated that these methods will find use either alone or in combination, as well as in combination with other diagnostic and prognostic methods. In particularly preferred embodiments, mutations in the genes encoding R1A are detected using the methods of the present invention. It is also contemplated that the methods of the present invention will find use in the detection and screening of mutations in the other subunits of PKA. In addition, it is contemplated that the methods of the present invention will find use in the identification and/or characterization of compounds that are effective in treating Carney complex, pigmentation defects, and/or tumors.

The present invention also provides methods and compositions for the identification and/or characterization of compounds useful for the treatment of Carney complex, pigmentation defects, and/or tumors.

DESCRIPTION OF THE INVENTION

Figure 1:
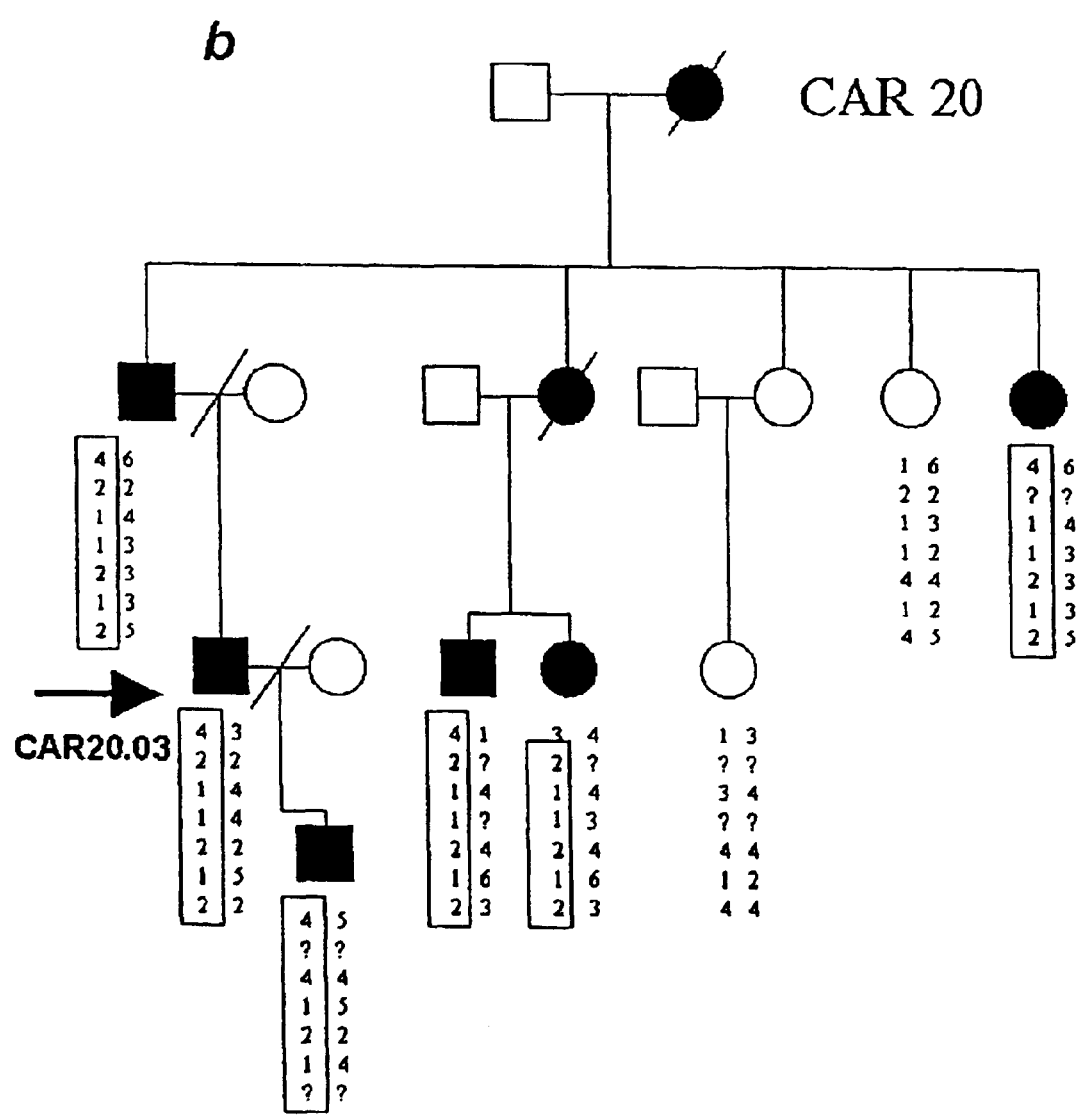
FIG. 1 provides the pedigree and chromosome 17 genotyping of family CAR20.

The present invention provides compositions and methods useful in the diagnosis and prognosis of Carney complex (CNC), as well as methods and compositions for the identification of compounds useful in the treatment and/or prevention of CNC. In addition, the present invention provides compositions and methods useful in the diagnosis and treatment of conditions associated with skin pigmentation defects, including but not limited to freckling, as well as endocrine tumors including, but not limited to adrenal and pituitary tumors. In addition, the present invention provides methods and compositions for the diagnosis and treatment of various types of cancers associated with abnormal activity of protein kinase A. In particular, the present invention provides genetic and other sequence information, as well as assay systems that will find use in these and related areas.

Because of its similarities to the McCune-Albright Syndrome (Stratakis, Front. Biosci., 5:D353–366 [2000]; and Weinstein et al., N. Eng. J. Med., 325:1688–1695 [1991]) and other features, such as paradoxical responses to endocrine signals (Stratakis et al, Ann. Intern. Med., 131:585–591 [1999]), genes implicated in cyclic nucleotide-dependent signalling have been considered as candidate causative agents of CNC. However, prior to the development of the present invention, this had not been shown with any certainty. During the development of the present invention, a previously unrecognized association between protein kinase A and CNC was identified and characterized.

Protein Kinase A

Protein kinase A (PKA) is a tetrameric holoezyme enzyme containing a regulatory subunit dimer and two catalytic subunits. Each of these subunits is encoded by a small family of genes and an array of PKA isozymes has been identified in many organisms. Each PKA subunit isoform is expressed in a particular group of tissues and some cell types express a complex mixture of multiple isozymes. Although the substrate specificity and kinetic rates of the catalytic subunit isoforms are the same, the regulatory subunits are functionally diverse (See e.g., Scott, Pharmac. Ther., 50:123–145 [1991]).

The mammalian catalytic subunit isoforms include Cα, Cβ, and Cγ. In addition, the catalytic subunit contains a core region of approximately 250 amino acids, referred to as the "catalytic core." This core is composed of several conserved sequence motifs which represent distinct domains involved in catalysis (e.g., ATP binding, substrate binding, and phosphoryltransfer). The phosphorylation of substrate proteins by the catalytic subunit of PKA triggers a wide variety of physiological responses that are controlled through the cAMP signalling pathway (See e.g., Scott, Pharmac. Ther., 50:123–134 [1991]).

There are two regulatory subunit classes, designated as "R1" and "R2." One function of these subunits is to inhibit the catalytic subunit. These subunits differ in molecular weight, protein sequence, phosphorylation state, tissue distribution, and subcellular localization. There are two isoforms of each subunit, designated as "R1A" (or "RIα"), "R2A" (or "RIIα"), "R1B" (or "RIβ"), and "R2B" (or "RIIβ"). The predominant isoforms are R1A and R2A; indeed, these isoforms are expressed in most tissues. Homologs of R1A (classified by their lack of an autophosphorylation site; a characteristic that differentiates R1 from R2) have been identified in various lower eukaryotes (e.g., Drosophila, *Dictyostelium discoideum*, and *Caenorhabiditis elegans*). In comparisons with their mammalian counterparts, these homologs have been shown to contain conserved structural features. The domain structure of the regulatory subunits indicates that these are highly asymmetrical proteins comprising a linear array of well-defined and functionally distinct sub-domains responsible for dimerization, subcellular localization, inhibition of the catalytic subunit, cAMP binding, etc.

As discussed in greater detail herein, during the development of the present invention, mutations were identified and characterized in one of the regulatory subunits, R1A. This is significant in that R1A is the most biologically important subunit, as it is expressed in almost every tissue. Furthermore, as discussed herein, during the development of the present invention, the tumor suppressor capability of R1A was identified and characterized. Mutations in this PKA subunit result in abnormal PKA function and the development of tumors due to uncontrolled cell growth.

Carney Complex and Loss of Heterozygosity on Chromosome 17

During the development of the present invention, in studies involving CNC families mapping to 17q, loss-of-heterozygosity (LOH) in the vicinity of the protein kinase A regulatory subunit 1A gene (PRKAR1A) was observed, including at a polymorphic site within its 5' region. Subsequently, three unrelated kindreds with an identical mutation in the coding region for PRKAR1A were identified. Analysis of these additional cases identified the same mutation in a sporadic CNC case, and different mutations in three other families, including one with isolated inherited cardiac myxomas. Analysis of protein kinase A (PKA) activity in CNC tumors demonstrated a decreased basal activity, but an increase in cAMP-stimulated activity compared to non-CNC tumors. Thus, it is contemplated that the germline mutations in PRKAR1A, an apparent tumor suppressor gene, as described herein, are responsible for the CNC phenotype in a subset of CNC patients.

Indeed, to evaluate the spectrum of PRKAR1A mutations involved in CNC, the entire National Institutes of Health and Mayo Clinic cohort of 53 CNC kindreds, comprised of 38 families and 15 patients with sporadic disease was investigated. As described in more detail herein, fourteen families were informative for linkage analysis. Four out of four families that mapped to 17q had PRKAR1A mutations, whereas no mutations were found in seven families exhibiting at least one recombination with 17q. In six of these families, CNC segregated with 2p16 markers (maximum cumulative two-point LOD score of 3.97 (θ=0) for the CA-2 locus). PRKAR1A mutations were also found in 12/24 non-informative families, and 7/17 sporadic cases. Overall, 15 distinct PRKAR1A mutations were identified in 22 of 53 kindreds (41.5%). In 14 mutations, the sequence change was predicted to lead to a premature stop codon, while one mutation altered the initiator ATG codon. Analysis of mRNA transcripts in patient lymphocytes treated with cycloheximide revealed that mutant mRNAs containing a premature stop codon were unstable, as a result of nonsense-mediated mRNA decay. Accordingly, the predicted mutant PRKAR1A protein products were absent in these cells. It is contemplated that genetic heterogeneity exists in CNC, and all of the CNC alleles on 17q are functionally null mutations of PRKAR1A. It is further contemplated that clinical heterogeneity in families mapping to 17q may be due to disease-modifier genes located elsewhere in the genome. Nonetheless, work conducted during the development of the present invention indicates that CNC is the first human disease caused by mutations of one of the subunits of the PKA holoenzyme, a critical component of numerous cellular signaling systems.

Identification of Genetic Changes on Chromosome 17

Linkage analysis of families with CNC initially demonstrated a genetic locus on 2p16 with an aggregate LOD score of 5.97 (θ=0.03), although no single family in that study had a LOD score greater than 1.8 for 2p16 (Stratakis et al., J. Clin. Invest., 97:699–705 [1996]). Additional genetic studies led to the description of families in whom CNC did not segregate with 2p16 markers (Basson et al., Am. J. Cardiol., 79: 994–995 [1997]; and Taymans et al., Am. J. Hum. Genet., 61, A84 [Suppl] [1997]). A genome-wide screen with these families demonstrated linkage to a second locus on 17q22–24 (Casey et al., Circul., 98:2560–2566 [1998]). During the development of the present invention, following loss-of heterozygosity (LOH) studies in CNC tumors and genetic linkage analysis in newly collected kindreds, mutations of the PRKAR1A gene, which encode the type 1A regulatory subunit of protein kinase A were identified in 17q22–24-mapping families and several sporadic cases.

The present invention provides the genomic structure of the PRKAR1A tumor suppressor gene, as well as methods and compositions to assess the genetic heterogeneity associated with CNC in patients. Furthermore, although it not intended that the present invention be so limited, it is contemplated that despite the large number of PRKAR1A mutations, only one molecular phenotype is associated with CNC in chromosome 17-mapping families with the disease. Thus, it is contemplated that the a reduction of about 50% (or more) of the type 1A regulatory subunit of PKA in affected CNC tissues is the causative factor in the disease. It is further contemplated that tumors of CNC patients have a complete absence of PKA type 1A. It is also not intended that the present invention be limited to any particular mechanism. Indeed, an understanding of the mechanism(s) is not necessary in order to use the present invention.

During the development of the present invention, identification of genetic changes at 17q22–24 in a pituitary tumor from a CNC patient belonging to a family that was mapped to that region (Casey et al., Circul., 98:2560–2566 [1998]), stimulated a search for additional families mapping to 17q22–24 and for genetic alterations present in their tumors. Polymorphic markers from the 17q22–24 area proximal to PRKAR1A showed complete segregation with the disease in the CAR01 family (referred to as "YC01," in Casey et al., Circul., 98:2560–2566 [1998]; this is a large pedigree with primary pigmented nodular adrenocortical disease [PPNAD] and other manifestations of CNC). The disease was also found to segregate with markers from 17q in CAR20, a family that was characterized during the development of the present invention. Table 2 lists the clinical manifestations observed in individuals within the CAR20 family.

TABLE 2

Clinical Manifestations of Individuals in Family CAR20

| Individual | Acromegaly | Cardiac Myxoma | Lentigenes | Other[a] |
|---|---|---|---|---|
| II.1 | + | − | + | LCCSCT |
| II.4 | | + | + | |
| II.6 | | | | |
| II.7 | − | − | − | |
| II.8 | + | + | + | |
| III.1[b] | + | + | + | PMS, LCCSCT |
| III.2 | + | + | + | |
| III.3 | + | + | + | |
| III.4 | − | − | − | |
| IV.1 | − | − | + | |

[a]LCCSCT = Large-cell calcifying Sertoli cell tumor
PMS = Psammamatous melanotic schwannoma A polymorphic sequence within the 5' region of PRKAR1A ([PRKAR1A(CA)n]), which segregated in both families was identified. LOH regions were then investigated in tumor specimens obtained from four members of the two families and the probands of other kindreds with CNC. All samples showed LOH of an 8 cM-long area of 17q22–24, around PRKAR1A (See, FIG. 2, Panel A), and the allele segregating with the disease was retained in all informative tumor samples (See, FIG. 2, Panel B).

Evaluation of PRKAR1A as a candidate for CNC was conducted using expressed sequence tags (ESTs) from the gene, to identify a bacterial artificial chromosome (BAC) that contained its genomic sequence ([BAC 62_F_10]). By comparing the cDNA and genomic sequences, it was possible to delineate the intron-exon boundaries of the gene. The results obtained indicated that what had previously been reported to be one exon (exon 4) was actually split into two exons. These two exons are referred to herein as "4A" and "4B." Primers for each exon were designed and used to screen the gene in denaturing high performance liquid chromatography (DHPLC). These results indicated the presence of heteroduplex formation in exon 4B in affected members of families CAR01 and CAR20. Sequence analysis showed a 2-base pair deletion at position 578 of PRKAR1A in affected patients from both families. The 578delTG mutation, which is located in exon 4B and corresponds to position 163 of the protein, leads to a frame-shift and premature termination after four missense residues (See, Table 3). In addition, the families did not share 17q22–24 haplotypes of the disease-bearing allele, making it unlikely that they carried the same chromosome 17.

To confirm the identity of PRKAR1A with the CNC-causing gene, mutations of the gene were sought in other families and sporadic cases. One additional family (CAR108) and a patient with sporadic disease (CAR23.03) also carried the 578delTG mutation (See, Table 3). The mutation appears to have occurred de novo in CAR23.03, because it was not present in the parent's peripheral blood DNA.

TABLE 3

Mutations in PRKAR1A in Families with CNC

| Kindred | Diagnosis | Mutation | Effect on RIα |
|---|---|---|---|
| CAR01 | CNC | 578delTG (exon 4B) | Frame-shift after codon 163; stop codon after 4 missense residues; truncation before cAMP binding regions |
| CAR20 | CNC | | |
| CAR108 | CNC | | |
| CAR23.03 (sporadic) | CNC | | |
| CAR13 | CNC | 889 GG > CT (exon 8) | Missense codon 262, followed by nonsense codon; truncation at N-terminus of the second cAMP binding domain |
| CAR25 | CNC | exon 8 IVS + 3 A > G | Mutation of 5' splice site of intron 8 |
| MYX01 | Inherited cardiac myxoma | 617delTTAT (exon 5) | Frame-shift after residue 204; stop codon after 26 missense residues; mutation would also abolish the second cAMP binding domain |

Screening of additional patients with CNC revealed other mutations in PRKAR1A. A GG-to-CT change at cDNA position 889 was identified in kindred CAR13, leading to premature termination after residue 262. A presumed splice junction mutation at exon 8 was also found in family CAR25 (See, Table 3). Screening of 4 other patients with CNC (from kindreds CAR19, CAR110, CAR06, and CAR09), whose tumors were examined for LOH (FIG. 2, Panel A), did not reveal mutations in the coding parts of the gene. Probands from other families mapping to chromosome 2p16 or elsewhere (Stratakis et al., J. Clin. Invest., 97:699–70 [1996]; and Stratakis et al., Am. J. Hum. Genet., 65:A44 [1999]) did not have detectable alterations in PRKAR1A. In addition, PRKAR1A mutations were searched for in patients with either isolated myxomas or PPNAD. One family that had cardiac myxomas and no other CNC manifestations (Liebler et al, J. Thorac. Cardiovasc. Surg., 71:605–608 [1976]) had a four base pair deletion in exon 5 of PRKAR1A, leading to frame-shift and premature termination after 26 missense residues (family MYX01; See, Table 3). None of the three patients with sporadic PPNAD were found to carry a mutation in the coding sequences of PRKAR1A.

Thus, during the development of the present invention, mutations in PRK4R1A in several families with CNC and patients with the sporadic form of the disease have been identified. Three unrelated families and one sporadic case shared the same two base pair deletion in exon 4B of PRKAR1A, indicating that this site is a hotspot for mutation. The mechanism responsible for mutagenesis at this site remains unclear. Indeed, an understanding of the mechanism is not necessary in order to use the present invention. Although other mechanisms cannot be excluded, it is possible that because of the TGTG pattern present at the deletion site, DNA-polymerase stuttering may play a role (Tautz, Nucl. Acids Res., 17:6463–6471 [1989]).

Western Blotting

Figure 4:
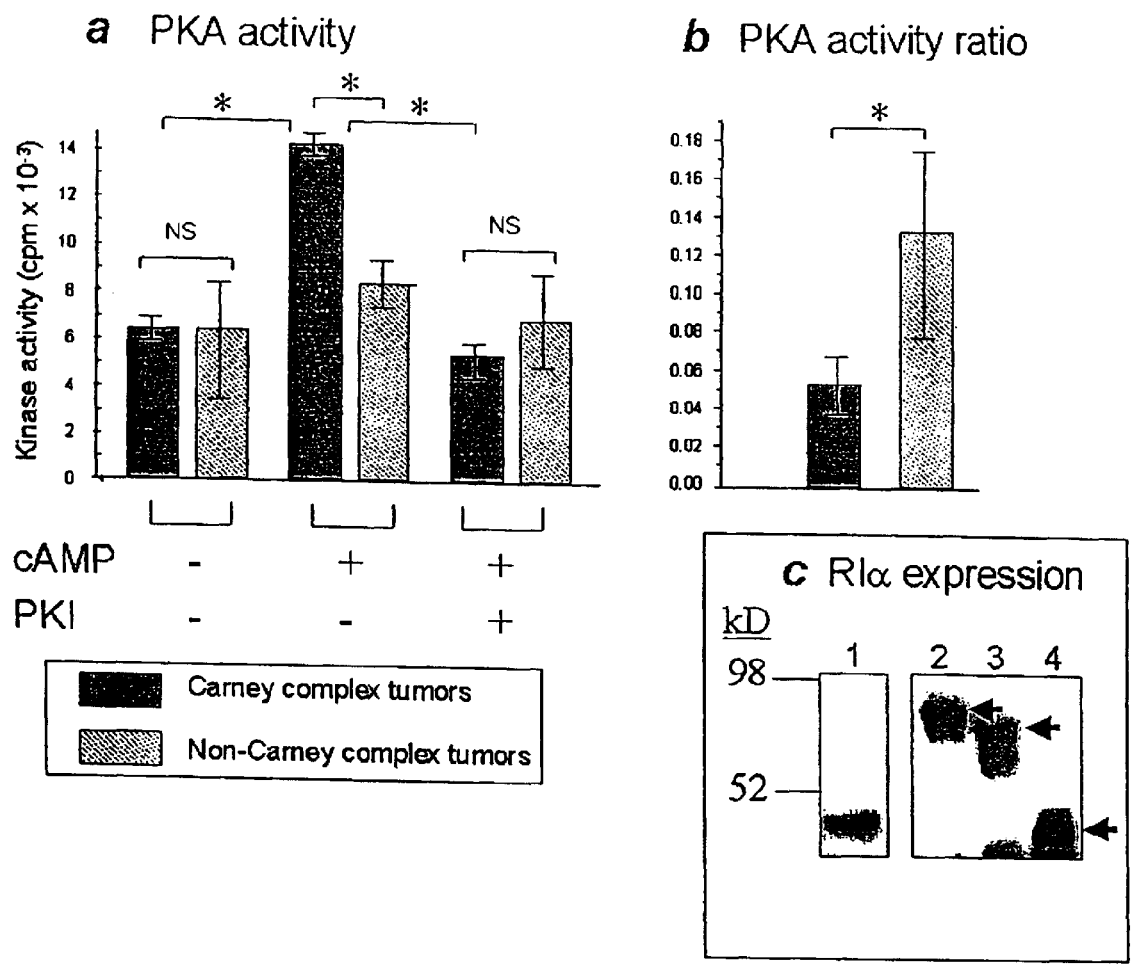
FIG. 4 provides results indicating the protein kinase (PKA) activity and expression of PRKAR1A in CNC tumors and cell lines. Panel A provides a comparison of total PKA activity between CNC steroid-producing tumors and control tumors at baseline. Panel B shows the PKA activity ratio. Panel C provides a Western blot containing protein lysates.

Western blotting of cellular proteins from a primary cell line from the CAR20.03 pituitary tumor and an PRKAR1A-specific antibody demonstrated the presence of full length PRKAR1A in the cells (FIG. 4, Panel C, lane 1). However, no truncated forms of the protein were observed. Control experiments with bacterially expressed GST-fusion proteins confirmed the ability of this antibody to detect the truncated protein (FIG. 4, Panel C, lanes 2–4). Lane 2 contained PRKAR1A nt 74–1228 (full length, expected size 72 kD), while lane 3 contained PRKAR1A nt74–871 (exon 8 truncation, expected size 59 kD), and lane 4 contained PRKAR1A nt 74–577 (exon 4B truncation, expected size 48 kD). In FIG. 4, size markers are indicated on the left; arrowheads denote the expected size of the fusion proteins. It is likely that the smaller sized bands represent degradation products.

mRNA Analyses

RT-PCR of the PRKAR1A message from the cell line established from the CAR20.03 pituitary tumor resulted in the detection of only the wild-type sequence, suggesting that the mutant mRNA may be unstable in the cells. Mutant mRNA was also not detected in another cell line that was established from a member of family CAR25 bearing a splice site mutation at the 5' splice site of intron 8. This observation is consistent with the cellular elimination of mutant mRNAs, as has been observed in other settings (Sun et al., Proc. Natl. Acad. Sci. USA 95:10009–10014 [1998]). However, it is not intended that the present invention be limited to any particular mechanism.

As Western blot experiments (See, Example 9) on samples from patients with known truncating mutations failed to detect the presence of foreshortened forms of the protein, mRNA in transformed lymphocytic and other tissue cell lines established from CNC patients were analyzed. Amplification of full-length or shorter forms of the PRKAR1A cDNA from kindreds with the 578delTG and exon 8 IVS+3G>A mutations and subsequent sequence analysis demonstrated only the presence of normal PRKAR1A mRNA. This suggested that the mutant mRNA was not widely present in the lymphocytes and other cells of these patients perhaps due to nonsense-mediated mRNA decay (NMD).

NMD is a mechanism by which cells can degrade mRNAs containing premature stop codons before they reach the translational machinery (Culbertson, Trends Genet., 15:74–80 [1999]; and Maquat, RNA 1:453–465 [1995]). Although an understanding of the mechanism is not necessary in order to use the present invention, this mechanism has been shown to prevent translation of mutant mRNAs containing premature stop codons in a variety of human diseases, including Ehlers-Danlos syndrome (Schwarze et al., Am. J. Hum. Genet., 66:1757–1765 [2000]) and Stickler syndrome (Freddi et al., Am. J. Med. Genet., 90:398–406 [2000]). Treatment of cells with translation inhibitors such as cycloheximide (CHX) or puromycin (PUR) can abrogate this phenomenon (Culbertson, Trends Genet., 15:74–80 [1999]; and Maquat, RNA 1:453–465 [1995]).

Indeed, treatment of transformed lymphocytes from the CAR01 family that carried the 578delTG mutation with CHX, followed by cloning of its cDNA and sequencing revealed that this treatment led to the production of mRNA containing the expected 2-bp deletion, as evidenced by the disruption of the sequence trace. Similarly, treatment of transformed lymphocytes and a tissue cell line from family CAR25 that carried the exon 8 IVS+3G>A mutation with CHX led to the induction of a readily visible splice variant cDNA, which was the result of a cryptic splice donor site produced by mutation of the cognate site. Subsequent sequence analysis also showed that this led to the presence of a premature stop codon in the mRNA.

In contrast, the A88G mutation, which abolishes the translational start codon (Table 13) but does not introduce a premature stop codon, would not be predicted to be subject to NMD. Analysis of mRNA from a patient carrying this mutation (family CAR19) demonstrated that the mRNA population was a 50:50 mixture of wild-type and mutant mRNA. In Western blotting studies from this patient, no shortened forms of PRKAR1A were detected. Analysis of the primary sequence of the mRNA revealed that after the cognate ATG, there are two out of frame ATG sequences, neither of which is part of a Kozak initiation consensus (Kozak, J. Biol. Chem., 266:19867–19870 [1991]). There was an in-frame ATG which is located within a reasonably good match sequence (at least equivalent to the cognate), which would be predicted to produce a protein lacking the 46 N-terminal amino acids of the protein. However, this protein was not detected in patients' cells.

Each of the PRKAR1A mutations reported to date is predicted to lead to the production of a truncated protein product. Thus, it was a possibility that the mutations could act by either haploinsufficiency (i.e., loss of function) or by a dominant negative effect (i.e., gain of function). However, because all of the CNC mutations were predicted to lead to premature peptide chain termination and NMD was shown to operate in these cells, it appears that all of the CNC mutations detected during the development of the present invention are functionally equivalent to null alleles. These results indicate that constitutional (germline) loss of one allele of PRKAR1A is the key factor in the pathogenesis of CNC. In CNC tumors, this loss of the PRKAR1A protein leads to enhanced intracellular signaling by PKA, as evidenced by an almost two-fold greater response to cAMP in CNC tumors when compared to non-CNC tumors.

Based on the above observations, it was predicted that any patient with a PRKAR1A mutation has the same defect at the molecular level. These analyses indicate that differences in patient presentations may be due to contributions from disease-modifying loci located outside of the PRKAR1A locus. There is perhaps no more convincing argument about this statement from the comparison of the two larger families (CAR01 and CAR25) that shared the 578delTG PRKAR1A mutation but had a dramatically different clinical phenotype. While family CAR01 had many individuals with PPNAD, this manifestation was completely absent from CAR20. In contrast, acromegaly and cardiac myxomas were strongly featured in CAR20, but were almost absent from CAR01. Many members of CAR20 (although not all) were highly pigmented, whereas this feature was much less prominent in CAR01. Thus, the protean manifestations of CNC appeared to be present or absent regardless of genotype, suggesting that a genotype-phenotype correlation does not exist. Similarly, there did not appear to be a difference between families that map to chromosome 17 and those that map elsewhere.

Indeed, because all of the chromosome 17 CNC alleles are functionally equivalent to null alleles, one would predict a lack of a genotype-phenotype correlation in patients with mutations of PRKAR1A. As indicated herein, this prediction was borne out by the studies described. Additionally, no significant differences have been identified between CNC patients that carry null mutations of PRKAR1A and those that do not. Thus, genetic, but not clinical, heterogeneity has been demonstrated.

The absence of expression of the abnormal PRKAR1A protein in CNC cells, along with the previously identified LOH of the normal PRKAR1A allele, indicates that, in tissues affected by CNC, tumorigenesis is caused by abolition of type I PKA activity. Thus, the methods and compositions of the present invention provide means for the diagnosis and screening of CNC, as well as methods and compositions for the identification of compounds suitable for the treatment of CNC and other diseases associated with abnormal pigmentation, as well as disorders associated with endocrine tumors and various cancers in which PRKAR1A plays a role as a tumor suppressor gene.

Protein Kinase A and cAMP Activity

A defective cyclic nucleotide-dependent pathway has long been considered a candidate mechanism for the various features of CNC (Stratakis, Front. Biosci., 5:D353–366 [2000]; Stratakis et al., J. Clin. Invest., 97:669–705 [1996]; and DeMarco et al., Hum. Genet., 98:185–188 [1996]) that include tumors similar to those of MAS (Stratakis, Front. Biosci., 5:D353–366 [2000]; and Stratakis et al., J. Clin. Invest., 97:669–705 [1996]) and paradoxical responses to hormonal stimuli (Stratakis et al., Ann. Intern. Med., 131:585–591 [1999]). One of the first candidate gene analyses for CNC was screening for GNAS1 (the gene responsible for MAS (Weinstein et al., N. Eng. J. Med., 325:1688–1695 [1991]) mutations; this study produced negative results (DeMarco et al, Hum. Genet., 98:185–188 [1996]). These results suggested that the defect in CNC was downstream from cAMP activation. The PKA holoenzyme, a critical component in cAMP-dependent signaling, was thus viewed as a likely candidate for the identification of mutations in patients with CNC. In addition to inactivating mutations of R1A, work conducted during the development of the present invention identified LOH for PRKAR1A in CNC tumors. PKA activity ratio was also decreased in CNC tumors. These data are consistent with the hypothesis that normal RIα functions as a tumor suppressor in tissues affected by CNC, perhaps by maintaining normal type-I PKA activity. In the absence of normal RIα, there appears to be an increased stimulation by cAMP, perhaps mediated by over-expression of the genes coding for the other regulatory subunits of the PKA complex. This type of compensatory response has been demonstrated in animal models lacking one of the subunits of the PKA holoenzyme (Cummings et al., Nature 382:622–626 [1996]; and Amieux et al., J. Biol. Chem., 272:3993–3998 [1997]).

Thus, as indicated above, to determine the functional consequences of these mutations, the cAMP responsiveness and PKA activity ratio in tumor cell extracts from families CAR01, CAR20 and CAR25, were measured and compared with tumor extracts from non-CNC patients (FIG. 4, Panels A and B). These data indicated that non-stimulated PKA activity was not significantly different in CNC tumors vs. non-CNC tumors at baseline (FIG. 4, Panel A, left). Addition of cAMP led to a stimulation in kinase activity in CNC tumors (kinase activity at baseline vs. following stimulation with cAMP, $p<0.001$) (FIG. 4, Panel A). This response was PKA-specific, as demonstrated by its inhibition by PKI, a specific PKA-inhibitor (Cho et al., Proc. Natl. Acad. Sci. USA 97:837–840 [2000]; kinase activity in response to cAMP vs cAMP and PKI, $p<0.001$), and it was not different between tumors with the 578delTG genotype (2 tumors from family CAR01 and 2 from family CAR20) and those with a different PRKAR1A mutation (2 tumors from CAR25). Both the stimulation of kinase activity with cAMP and the inhibition of that stimulation by PKI were greater in CNC tumors than those in the control samples ($p<0.05$). The peak kinase activity value in response to cAMP was higher in CNC tumors, as compared to the non-CNC tumors ($p<0.001$). The PKA activity ratio, a measure of how much PKA is in its active form (free/basal PKA), was decreased in CNC tumors vs the control samples ($p<0.001$), as expected from RIα-inactivating mutations (FIG. 4, Panel B). In FIG. 4, all error bars represent the standard error of the mean; "NS" indicates non-significant results; "*" indicates significant results at $p<0.05$; "+" and "−" indicate the presence and absence of cAMP or PKI, respectively.

Furthermore, the ratios of type-I PKA to type-II PKA can change dramatically during cell development, differentiation and transformation (Cho et al., Proc. Natl. Acad. Sci. USA 97:837–840 [2000]; and Scott, Pharmac. Ther., 50:123–145 [1991]), indicating that the PKA complex has substantial flexibility in its mediation of cAMP signaling. Other possible mechanisms for tumorigenesis in CNC, that would apply especially in the cases of point mutations of PRKAR1A, include an uninhibited catalytic subunit of the PKA complex, which by itself when mutated leads to unregulated PKA activity or a reduced turn-over of the cAMP molecule (Beebe et al., J. Biol. Chem., 259:3539–3547 [1984]).

Complementary Mouse Models of CNC

In order to more thoroughly assess the molecular effects of mutations in the genes involved in CNC, two complementary mouse models are provided. As discussed herein, molecular analysis of disease alleles in patients with CNC has indicated that it is caused by inactivating mutations of the PRKAR1A gene. Studies of PRKAR1A in sporadic tumors of the endocrine glands conducted during the development of the present invention have revealed loss-of-heterozygosity (LOH) at the PRKAR1A locus and immunoblotting studies have demonstrated loss of PRKAR1A protein in advanced tumors. Because the disease is inherited as an autosomal dominant trait, the loss of one allele (i.e., haploinsufficiency) is sufficient to initiate the tumorigenic phenotype.

One mouse model involves the use of antisense mRNA targeting to generate mice with reduced amounts of PRKAR1A to model the apparent haploinsufficiency observed in human disease are described. By placing the antisense transcript under the control of an artificial promoter containing tetracycline (Tet) regulatory elements (TREs) as known in the art (See e.g., Gossen and Bujard, Proc. Natl. Acad. Sci. USA 89:5547–5551 [1992]), tight control of the timing and amount of antisense mRNA produced by the animals is achieved by simply administering tetracycline in the animals' drinking water. However, in preferred embodiments, mice are treated with the tetracycline congener doxycycline (Doxy) because it has better stability and kinetics. The doses that are used for regulation of the artificial promoter are non-toxic to the mice and there is a good dose-response curve of the promoter to the dose of Doxy administered. This system allows control of the timing and amounts of reduction in the PRKAR1A protein.

In initial experiments, transgenic mice carrying a fragment of the prkarla cDNA cloned in the antisense orientation under the control of a TRE is crossed with mice carrying the Tet transactivator protein (tTA). This protein binds to and constitutively activates TRE-containing promoters, except in the presence of Doxy or Tet.

The offspring of this cross are genotyped and phenotyped to observe for the presence of embryonic effects of the antisense expression. In experiments where none are observed, mice are maintained in the absence of Doxy for approximately two (2) years, to watch for the development of tumors similar to those observed in CNC. In order to monitor this progress, mice are sacrificed at six (6) month intervals to observe for the presence of tumors.

In the case where double heterozygote mice are either not born or exhibit developmental malformations, two different approaches are used. First, female mice are treated with Doxy before mating and for specified periods of time during gestation. This facilitates the determination of in which gestation periods full prkarla expression is/are necessary for development. In the second line of investigation, mice are treated with Doxy throughout gestation and the antimicrobial removed after weaning. This allows the investigation of the tumorigenesis aspect of the phenotype rather than developmental aspect. Using the dose-response curve of the promoter for Doxy (See, Kistner et al, Proc. Natl. Acad. Sci. USA 93:10933–10938 [1996]), it is contemplated that the level of prkar1a needed to prevent tumor development will be determined and monitored over time.

In the second model, conditional knockout mice are constructed. In this model, a pair of loxP sites are introduced around the first and second exon of the prkar1a gene. Incubation of cells containing this construct with the cre recombinase leads to excision of the first and second exons of the gene and a null allele. Mice containing this floxed prkar1a allele are used to address various aspects of CNC disease and pathogenesis.

In one embodiment, a heterozygous null animal is provided as an "exact" genetic model for human CNC patients. These mice are normal at birth but develop tumors as they age. In some embodiments, heterozygous nulls are bred and sacrificed at bimonthly intervals up to two (2) years of age. As CNC patients tend to present with tumors in their second and third decades of life, this time frame provides a suitable window in which to observe the development of tumors.

In other embodiments, the same system is used to create homozygous null animals to examine the effects of the lack of PRKAR1 on development. Preliminary information has indicated that homozygous nulls are embryonic lethal, which is a strong reason for beginning experiments using a knockout approach. PRKAR1A is expressed ubiquitously in tissues, so it is not completely unexpected that the complete knockout has this phenotype. The endocrine organs of these animals are observed for malformations.

In still further embodiments, mice homozygous for the floxed prkar1a allele are mated with mice expressing cre recombinase in well-defined tissues. These animals provide means to examine the effects of loss of this gene product on tumor formation. In some embodiments, target mice include those expressing cre under the control of the keratin K5 promoter (Tarutani et al., Proc. Natl. Acad. Sci. USA 94:7400–7405 [1997]) to examine pigmentation and tumors in the skin. In other embodiments, target mice including those expressing cre in neuroendocrine cells under the control of the tyrosinase promoter. The resulting offspring are observed for the development of phenotypic traits associated with CNC (e.g., myxomas, endocrine tumors, skin pigmentation abnormalities, etc.).

Sporadic Benign and Malignant Thyroid Tumors

Thyroid lesions are common sporadic tumors. Indeed, thyroid cancer is the most frequent endocrine carcinoma (See e.g., Mazzaferri, N. Eng. J. Med., 328:553–559 [1993]). Several inherited multiple neoplasia syndromes are associated with a predisposition to thyroid tumors (Sarlis, Rev. Endocrinol. Metab. Dis., 1:183–196 [2000]; Eng, J. Clin. Endocrinol. Metab., 85:1755–1757 [2000]; Farid et al., Endocrinol. Metab. Clin. N. Amer., 24:865–883 [1994]; and Fagin, J. Clin. Endocrinol. Metab., 82:342–344 [1997]), including CNC. Indeed, in a recent study, thyroid gland abnormalities, mostly benign non-hormone secreting follicular adenomas, were found in over two-thirds of patients with CNC (Stratakis et al., J. Clin. Endocrinol. Metab., 82:2037–2043 [1997]). Papillary and follicular thyroid carcinomas have also been described with increased frequency in patients with CNC (Ain, Endocrinol. Metab. Clin. N. Amer., 24:711–760 [1995]; Bier et al., Thorac. Cardiovasc. Surg., 37:317–319 [1989]; and Radin and Kempf, Radiol., 196:383–386 [1995]), indicating that thyroid carcinomas in these patients develop in situ from precursor benign lesions (Stratakis et al., [1997], supra), in a way similar to the hamartoma/adenoma-carcinoma sequence (Kinzler and Vogelstein, Cell 87:159–170 [1996]; and Bosman, J. Pathol., 188:1–2 [1999]).

As discussed herein, RIα is the most abundant regulatory subunit of the cAMP-dependent PKA. Genes implicated in cyclic nucleotide-dependent signaling have been considered possible candidates for thyroid tumors, albeit mostly benign. Somatic activating mutations in the thyrotropin receptor (TSHR) and α subunit of the stimulatory G protein (GNAS1) genes lead to increased cAMP production and are responsible for as many as half of sporadic toxic thyroid nodules (Parma et al., Nature 365:649–651 [1993]; Fuhrer et al., J. Clin. Endocrinol. Metab., 82:3885–3891 [1997]; Esapa et al., J. Clin. Endocrinol. Metab., 82:493–496 [1997]; Russo et al., Oncogene 11:1907–1011 [1995]). However, there is evidence for this pathway's involvement in thyroid cancer (Esapa et al., supra). Individuals with McCune-Albright syndrome (MAS), a disease with similarities to CNC (Pack et al., J. Clin. Endocrinol. Metab., 85:3860–3865 [2000]), who bear somatic GNAS1 mutations in their thyroid glands, may be predisposed to develop thyroid cancer (Bonat et al., Proc. 82nd Ann. Meet. Endocrine Soc., Toronto, Canada, Abstract #P2–2099 [2000]). In addition, both in vitro (Fournes et al., Oncogene 16:985–900 [1998]; and Du Villard et al., Oncogene 19:4896–4905 [2000]) and in vivo (Michiels et al., Proc. Natl. Acad. Sci. USA 91:10488–10492 [1994]; Coppee et al., Oncogene 13:1471–1482 [1996]; and Ledent et al., Endocrinol., 138:369–378 [1997]) models of cAMP overproduction show an increased potential for oncogenesis in thyroid cells.

As discussed herein, follicular adenomas (FA's) and papillary, follicular, and undifferentiated thyroid carcinomas (PTC, FTC, and UTC, respectively) were examined for loss-of-heterozygosity (LOH) of the 17q22–24 region, and also screened the PRKAR1A gene directly for sequence changes. All tumors were also studied by immunohistochemistry (IHC) using a monoclonal antibody specific for RIα. Consistent LOH of the 17q locus was observed in 7 of 17 informative samples (41%): 5 of 11 UTC's and 2 of 6 PTC's. None of the FA's had any abnormalities. A 499C>T mutation was observed in one of the UTCs, leading to a premature termination codon in exon 4B (Q167X). In one PTC, an intronic 2-bp deletion, IVS7–78delTT was detected, although it did not cause any PRKAR1A cDNA alterations. Decreased RIα immunostaining was found in samples that showed LOH; there was no staining for RIα in the UTC carrying a PRKAR1A inactivating mutation. Thus, the RI-α subunit of PKA is contemplated to function as a tumor suppressor in thyroid cells, as shown by frequent LOH of its locus at 17q and decreased RI-α staining in sporadically-occurring thyroid cancer. Indeed, the results provided herein indicate that the RI-α subunit of PKA may have tumor suppression function in thyroid cells, as shown by frequent LOH of the PRKAR1A 17q22–24 locus and decreased RI-α expression in both PTCs and UTCs. Albeit an apparently rare event, PRKAR1A inactivating mutations should be added to the list of genetic defects involved in both c-AMP signaling and sporadic thyroid tumorigenesis, although additional mechanisms maybe involved in RIα's inhibition of tumor suppression function in thyroid cells.

The rare presence of PRKAR1A inactivating mutations indicated that other mechanisms might be responsible for decreased staining and, presumably, loss of RI-α tumor suppression function in these tumors. Methylation of promoter sequences, translocations and other chromosomal re-arrangements have been proposed for silencing of tumor suppressor genes in neoplastic cells, including those of thyroid carcinomas (Elisei et al., Cancer 83:2185–2193 [1998]). Although methylation of the PRKAR1A locus has not been demonstrated in any tissue or cell lines, the 17q locus is frequently involved in chromosomal re-arrangements in cancer, including the t(10;17) translocation (Grieco et al., Cell 60:557–563 [1990]; and Sozzi et al., Genes Chromosomes Canc., 9:244–250 [1994]) that includes PRKAR1A sequences and results in the RET/PTC2 chimeric oncogene in PTC (Lanzi et al., Oncogene 7:2189–2194 [1992]; and Bongarzone et al., Mol. Cell Biol., 13:358–366 [1993]). A chromosomal rearrangement, the t(2:3)(q13;p25) resulting in the PAX8-PPAR-γ1 fusion oncogene, has also been postulated to be frequent in FTC (Kroll et al., Science 289:1357–1360 [2000]). However, this abnormality does not include chromosome 17 or RIα. It should also be noted that both the PTC and FTC re-arrangements result in oncogene activation, rather than tumor suppressor gene inactivation.

LOH at 17q22–24 has been observed at chromosome 17 in thyroid carcinoma patients (Ward et al, J. Clin. Endocrinol. Metab., 83:525–530 [1998]; and Kitamura et al., Genes Chromosomes Canc., 27:244–251 [2000]). These findings do not exclude the possibility that yet another gene at 17q22–24, in the vicinity of PRKAR1A, may be directly involved in the emergence of NMTC. This was the case with at least one other gene in the proximity of PTEN at 10q, an area previously shown to undergo LOH in thyroid tumors (Gimm et al., J. Clin. Endocrinol. Metab., 86:1801–1805 [2001]). The identification of the MINPP1 gene at 10q explained some of the discrepancy between the high frequency of LOH of the PTEN locus (Zedenius et al., Hum. Genet., 97:299–303 [1996]) and the relative rarity with which mutations of this gene are found in sporadic thyroid tumors (Halachmi et al., Genes Chromosomes Canc., 23:239–243 [1998]). Epigenetic silencing of PTEN, such as that discussed above as a possibility for PRKAR1A, may account for the remaining part of tumors showing LOH for 10q and carrying wild-type PTEN sequences (Zhou et al., Am. J. Pathol., 157:1123–1128 [2000]). It should be noted, however, that LOH around PTEN involved genomic regions significantly larger than those around the presently reported PRKAR1A locus (Gimm et al., supra). Furthermore, examination of the available 17q contigs flanking PRKAR1A did not show any other expressed sequences likely to be functioning as tumor suppressor genes (Deloukas et al., Science 282:744–746 [1998]).

However infrequent its molecular changes may be, PRKAR1A should be added to the growing list of genes that are involved in sporadic thyroid tumor formation. Although no single genetic defect appears to be responsible for even the relatively rare cases of familial NMTC, several genes have been linked to its initiation and/or progression. They include not only genes directly involved in thyroid function, such as TSHR (Yen, Rev. Endocrinol. Metab. Dis., 1:123–129 [2000]), but also oncogenes, such as the ret/PTC family, trk, c-myc, genes of the Ras family (H-ras, N-ras, and K-ras), c-kit, c-met and the c-met ligand, growth factors or growth factor receptors, such as vascular endothelial growth factor (VEGF) and its type-1 receptor (FLT-1), and cell-cycle- and apoptosis-controlling genes, including PTEN (See e.g., Ain, supra; Sarlis, Rev. Endocrinol. Metab. Dis., 1:183–196 [1993]; Eng, J. Clin. Endocrinol. Metab., 85:1755–1757 [2000]; Farid et al., Endocrinol. Metab. Clin. N. Amer., 24:865–883 [1994]; Fagin, J. Clin. Endocrinol. Metab. 82:342–344 [1997]; and van der Laan et al., Thyroid 5:67–73 [1995], for reviews), APC (Cetta et al., J. Clin. Endocrinol. Metab. 85:286–292 [2000]) and TP53 (Ho et al, Canc. Lett., 103:57–63). TGF-β has also been reported to be a cardinal growth-inhibitory factor in thyroid cells, mainly antagonistic to the proliferative actions of insulin-like growth factor-I (Belfiore et al., Biochimie 81:403–407 [1999]; and Kimura et al., Thyroid 9:119–125 [1999]).

It is contemplated that several of the above genes are linked to the PKA pathway directly or indirectly, although most of the related research has been done in tissues other than the thyroid (Delgado and Ganea, J. Immunol., 166:1028–1040 [2001]; and Ramstad et al., Cell Signal., 12:557–563 [2000]). In thyroid cells, few studies do show an association between PKA and oncogenic pathways (Villone et al., Eur. J. Endocrinol., 142:286–293 [2000]). It is also possible that a disturbance of the PKA pathway caused by RIα deficiency leads to activation of alternate c-AMP-inducible pathways that have also been linked to thyroid cell proliferation (reviewed in Richards, Mol. Endocrinol., 15:209–218 [2001]).

In sum, the data obtained during the development of the present invention indicate that PRKAR1A, a novel tumor suppressor gene and regulator of PKA activity, or its locus at 17q, are likely to be involved in the molecular events leading to thyroid cancer. As in other tissues, tumorigenesis in the thyroid is likely to involve several steps (See e.g., Kinzler and Vogelstein, Cell 87:159–170 [1996]; Bosman, J. Pathol., 188:1–2 [1999]; and Knudson, Ann. Rev. Genet., 34:1–19 [2000]). Nonetheless, the data obtained during the present invention clearly indicates that 17q LOH and/or loss of RI-α-mediated inhibition of cAMP-dependent PKA activity is likely to be one of the steps involved in the development of thyroid tumors.

Diagnostic Criteria for CNC and Recommendations for Screening and Follow-Up

In addition to imaging, biochemical screening and molecular testing procedures described herein, Table 1 provides diagnostic criteria for CNC. In brief, a patient is considered to have CNC if two major criteria are present. In the alternative, the diagnosis may be made if one major criterion is present and a first-degree relative has CNC or an inactivating PRKAR1A mutation.

For post-pubertal pediatric and adult patients with established CNC, the following annual studies are recommended: echocardiogram, measurement of urinary free cortisol levels (which can be supplemented by diurnal cortisol or the overnight 1 mg dexamethasone testing) and serum IGF-1 levels. Male patients should also have testicular ultrasonagraphy at the initial evaluation, so that minute calcifications (presumably LCCSCT) may be followed by annual ultrasound thereafter. Thyroid ultrasonography should also be performed at the initial evaluation and repeated as needed. Transabdominal pelvic ultrasonography is recommended for the initial evaluation of female patients, but need not be repeated unless there is a detectable abnormality, because of the low risk of ovarian malignancy.

More elaborate clinical and imaging studies may be necessary for the detection of PPNAD and GH-producing pituitary adenoma in patients without overt clinical manifestations of adrenal or pituitary disease, respectively. For the former, a dexamethasone-stimulation test is recommended, performed, and interpreted with the diagnostic criteria suggested by Stratakis et al. (Stratakis et al., Ann. Intern. Med., 131:585–591 [1999]). Diurnal cortisol levels ("short" diurnal variation test: insertion of an indwelling venous catheter to a hospitalized patient followed by sampling for cortisol levels at 11:30 PM and 12:00 midnight for the night-time sample, and at 7:30 AM and 8:00 AM for the morning sample), in addition to adrenal computed tomography, may also be obtained. For the detection of early acromegaly, oral glucose tolerance test (oGTT) and TRH-testing may be conducted in addition to IGF-1 levels and pituitary magnetic resonance imaging. IGF-1, oGG, and/or TRH testing may be abnormal in patients with CNC several years before a pituitary tumor is visible on MRI, if one is ever detected (See, Pack et al., J. Clin. Endocrinol. Metabol., 85:3860–3865 [2000]).

Pediatric patients with CNC should have echocardiography during the first six months of life and annually thereafter. Biannual echocardiographic evaluation may be necessary for pediatric patients with history of an excised myxoma. Most endocrine tumors in CNC do not become clinically significant until the second decade of life, although they are sometimes detectable at a much earlier age. Thus, imaging and biochemical screening are not necessary in young, pre-pubertal children, except for diagnostic purposes. However, pediatric patients with LCCSCT or a microcalcification detected by testicular ultrasonography need close monitoring of growth rate and pubertal status. Some of these patients require bone age determinations and further evaluation.

In sum, clinical and biochemical screening for CNC remain the gold standard for diagnosis of CNC. Molecular testing for PRKAR1A mutations, as described herein, is advised for detection of affected patients in families with known mutations of the gene, in order to avoid unnecessary medical surveillance of non-carriers. Thus, molecular diagnosis finds use in aiding the assessment of patients suspected of being affected by CNC.

Definitions

As used herein, the terms "lentigenoses" and "lentiginoses" refer to diseases associated with abnormal pigmentation of the skin and mucosa.

As used herein, the terms "lentigo" ("lentigines") refer to tan or brown macules on the skin typically brought on by exposure to the sun. Another variety of lentigines is unrelated to sunlight exposure and is appears in children between 2 and 5 years of age (i.e., prior to the onset of freckles). The melanin pigment in a lentigo is at a deeper level of the epidermis than in a freckle.

As used herein, the term "freckle" refers to a brown or tan macule on the skin that usually results from exposure to sunlight. There is an inherited tendency to develop freckles and it is most frequently observed in very light-skinned and red-haired individuals.

As used herein, the term "Hutchinson's freckle" refers to a tan patch on the skin that slowly grows and becomes mottled, dark, thick, and nodular. The lesion is typically observed on one side of the face of elderly persons. Local excision is recommended, as these lesions often become malignant.

As used herein, the term "lentigo maligna melanoma," is a neoplasm which develops from Hutchinson's freckles on the face or other exposed skin surfaces. Typically, it is asymptomatic, flat, and tan or brown, with irregular darker spots and frequent hyperpigmentation. It is one of the of the three major clinical types of melanoma and occurs in 10–15% of melanoma patients.

In particular, the terms "protein kinase" (or "protein kinase holoenzyme") and "holoenzyme subunit gene," refer to the complete protein kinase holoenzyme, and holoenzyme subunit nucleotide sequence(s), respectively. However, it is also intended that the term encompass fragments of the protein kinase holoenzyme and holoenzyme subunit sequences, such as those that encode particular domains of interest, including subunit proteins, as well as other domains within the full-length protein kinase holoenzyme or holoenzyme subunit nucleotide sequence. Furthermore, the terms "protein kinase holoenzyme," "holoenzyme subunit nucleotide sequence," "protein kinase holoenzyme," and "holoenzyme subunit polynucleotide sequence" encompasses DNA, cDNA, and RNA (e.g., mRNA) sequences. It is also intended that the term encompass fragments of the protein kinase sequence. The above also applies to variants of protein kinase.

The term "protein kinase A" refers to the protein kinase that serves as the major intracellular receptor for cyclic AMP (cAMP), and is commonly referred to as "protein kinase A" or "PKA." PKA is a tetrameric holoenzyme complex composed of separate regulatory and catalytic subunits. It is also intended that the terms encompass the array of PKA isozymes identified in various organisms. In mammalian cells, the catalytic subunit isoforms include Cα, Cβ, and Cγ. The regulatory subunit classes are RI (RI) and R2 (RII), with two isoforms of each class (i.e., R1A, R1B, R2A, and R2B).

As used herein, the term "$K_m$" refers to the Michaelis-Menton constant for an enzyme and is defined as the concentration of the specific substrate at which a given enzyme yields one-half its maximum velocity in an enzyme catalyzed reaction.

A used herein, the term "gene" refers to a nucleic acid (e.g., DNA) sequence that comprises coding sequences necessary for the production of a polypeptide or precursor (e.g., protein kinase holoenzyme or holoenzyme subunit, as appropriate). The polypeptide can be encoded by a full length coding sequence or by any portion of the coding sequence so long as the desired activity or functional properties (e.g., enzymatic activity, ligand binding, signal transduction, tumor suppression, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

A "variant" of protein kinase A as used herein, refers to an amino acid sequence of the protein kinase A holoenzyme or a subunit of the holoenzyme that has alterations in one or more amino acids. The variant may have "conservative" changes, wherein a substituted amino acid has similar structural or chemical properties, (e.g. replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. Pat. No. 5,652,096, hereby incorporated by reference.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism that can be isolated from a source in nature and which has not been intentionally modified by man in the laboratory is naturally-occurring.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "biologically active," as used herein, refers to a protein or other biologically active molecules (e.g., catalytic RNA) having structural, regulatory, or biochemical functions of a naturally occurring molecule. Likewise, "immunologically active" refers to the capability of the natural, recombinant, or synthetic protein kinase A (holoenzyme or subunit(s)), or any oligopeptide or polynucleotide thereof, to induce a specific immune response in appropriate animals or cells and to bind with specific antibodies.

The term "agonist," as used herein, refers to a molecule which, when bound to protein kinase A or at least one subunit of the holoenzyme, causes a change which increases the activity of the kinase or the subunit. Agonists may include proteins, nucleic acids, carbohydrates, or any other molecules which bind or interact with protein kinase A or any of its subunits.

The terms "antagonist" or "inhibitor," as used herein, refer to a molecule which, when bound to protein kinase A or at least one subunit of the holoenzyme, blocks or reduces the activity of protein kinase A or any of its subunits. Antagonists and inhibitors may include proteins, nucleic acids, carbohydrates, or any other molecules which bind or interact with any portion of the protein kinase A holoenzyme (e.g., one or more of the subunits).

The term "modulate," as used herein, refers to a change or an alteration in the biological activity of protein kinase A or any of its subunits. Modulation may be an increase or a decrease in protein activity, a change in binding characteristics, or any other change in the biological, functional, or immunological properties of protein kinase A or any of its subunits.

The term "derivative," as used herein, refers to the chemical modification of a nucleic acid encoding any of the protein kinase A subunits, or the encoded protein of any of the protein kinase A subunits. Illustrative of such modifications would be replacement of hydrogen by an alkyl, acyl, or amino group. A nucleic acid derivative would encode a polypeptide which retains essential biological characteristics of the natural molecule.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S.D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et aL, EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "complementary" or "complementarity" are used in reference to polynucleotides (i.e., a sequence of nucleotides) related by the base-pairing rules.

For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Those in the art well know that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a CDNA or genomic clone, the term "substantially homologous" refers to any probe which can hybridize to either or both strands of the double-stranded nucleic acid sequence under conditions of low stringency as described above.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length LAT cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length LAT sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "polymerase chain reaction" ("PCR") refers to the methods described within U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H.A. Erlich (ed.), PCR Technology, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the term "antisense" is used in reference to RNA sequences which are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "polyA+RNA" refers to RNA molecules having a stretch of adenine nucleotides at the 3' end. This polyadenine stretch is also referred to as a "poly-A tail". Eukaryotic mRNA molecules contain poly-A tails and are referred to as polyA+RNA.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a protein kinase subunit (e.g., the regulatory subunit type 1A of protein kinase A) includes, by way of example, such nucleic acid in cells ordinarily expressing the protein kinase subunit where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 1 lp15.5 portion of human chromosome 11 is the portion located on chromosome 11 (11) on the short arm (p) in the first region (1) in the 5th band (5) in sub-band 5 (.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and in situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "purified" or "to purify" refers to the removal of contaminants from a sample. For example, anti-protein kinase antibodies are purified by removal of contaminating non-immunoglobulin proteins; they are also purified by the removal of immunoglobulin that does not bind protein kinase (e.g., protein kinase A). The removal of non-immunoglobulin proteins and/or the removal of immunoglobulins that do not bind protein kinase results in an increase in the percent of protein kinase-reactive immunoglobulins in the sample. In another example, recombinant protein kinase polypeptides are expressed in bacterial host cells and the polypeptides are purified by the removal of host cell proteins; the percent of recombinant protein kinase polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "fragment of a polypeptide" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., various fragments of the protein kinase subunits). Fragments typically are at least 4 amino acids long, preferably at least 20 amino acids long, usually at least 50 amino acids long or longer, and span the portion of the polypeptide required for proper activity of the protein.

As used herein, the term "fusion protein" refers to a chimeric protein containing the protein of interest (e.g., protein kinase holoenzyme or subunit(s) and fragments thereof) joined to an exogenous protein fragment (the fusion partner which consists of a non-protein kinase protein). The fusion partner may enhance solubility of the protein kinase as expressed in a host cell, may provide an affinity tag to allow purification of the recombinant fusion protein from the host cell or culture supernatant, or both. If desired, the fusion protein may be removed from the protein of interest (i.e., protein kinase holoenzyme or subunit(s) or fragments thereof) by a variety of enzymatic or chemical means known to the art.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

As used herein, the term "affinity tag" refers to such structures as a "poly-histidine tract" or "poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate column.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The "non-human animals" of the invention comprise any non-human animals capable of overexpressing protein kinase mRNA and/or proteins. Such non-human animals include vertebrates such as rodents, non-human primates, ovines, bovines, ruminants, lagomorphs, porcines, caprines, equines, canines, felines, aves, etc. Preferred non-human animals are selected from the order Rodentia, most preferably mice.

The term "order Rodentia" refers to rodents (i.e., placental mammals [Class Euthria] which include the family Muridae (rats and mice).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals". A transgenic animal is an animal whose genome has been altered by the introduction of a transgene.

The term "transgene" as used herein refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-occurring gene.

A "non-human mammal expressing reduced levels of a protein kinase" is a mammal which expresses a level of a particular protein kinase which is lower than that found in a wild-type mammal. A mammal that "lacks the ability to produce functional protein kinase" is a mammal that produces undetectable levels of a particular protein kinase (i.e., a level which is not statistically above background levels in the assay employed). A functional protein kinase is a protein kinase which has the same properties as does the wild-type protein kinase.

A "non-human mammal expressing reduced levels of protein kinase A" is a mammal which expresses a level of protein kinase A which is lower than that found in a wild-type mammal. A mammal that "lacks the ability to produce functional protein kinase A" is a mammal that produces undetectable levels of protein kinase A (i.e., a level which is not statistically above background levels in the assay employed). A functional protein kinase A is a protein kinase A, which has the same properties as does the wild-type protein kinase A.

A "non-human mammal expressing reduced levels of protein kinase A subunit" is a mammal which expresses a level of a protein kinase A subunit which is lower than that found in a wild-type mammal. A mammal that "lacks the ability to produce functional protein kinase A subunit" is a mammal that produces undetectable levels of a particular protein kinase A subunit (i.e., a level which is not statistically above background levels in the assay employed). A functional protein kinase A subunit is a protein kinase A subunit, which has the same properties as does the wild-type protein kinase A subunit.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The protein kinase holoenzyme or holoenzyme subunits may be expressed in either prokaryotic or eukaryotic host cells. Nucleic acid encoding the protein kinase holoenzyme or holoenzyme subunit may be introduced into bacterial host cells by a number of means including transformation of bacterial cells made competent for transformation by treatment with calcium chloride or by electroporation. If the protein kinase holoenzyme or holoenzyme subunit are to be expressed in eukaryotic host cells, nucleic acid encoding the protein kinase holoenzyme or holoenzyme subunit may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al., EMBO J. 6:383–388 [1987]). Alternatively, infection can be performed at a later stage. Virus or virus-producing cells can be injected into the blastocoele (D. Jahner et al., Nature 298:623–628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the protein kinase (e.g., protein kinase A subunit(s), such as the type 1A regulatory subunit) mRNA-specific signal observed on Northern blots). The amount of mRNA present in the band corresponding in size to the correctly spliced protein kinase transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

An animal whose genome "comprises a heterologous polynucleotide sequence inserted into the endogenous protein kinase subunit genes" is an animal whose genome contains a polynucleotide sequence not naturally found in the endogenous protein kinase gene. The heterologous polynucleotide sequence may comprise a selectable marker gene not naturally found in the protein kinase subunit genes which is introduced by means of molecular biological methods. The heterologous selectable marker may be either a positive selectable marker or a negative or counter-selectable marker.

As used herein, the term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk- cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of protein kinase (holoenzyme or subunit(s) instability or inactivity in animals (e.g., greater sensitivity to ultraviolet radiation).

A compound is said to be "in a form suitable for administration to the mammal" when the compound may be administered to a mammal by any desired route (e.g., oral, intravenous, subcutaneous, intramuscular, etc.) and the compound or its active metabolites appears in the blood of the mammal. Administration of a compound to a pregnant female may result in delivery of the compound to the fetuses of the pregnant animal.

A "composition comprising a given polynucleotide sequence" as used herein refers broadly to any composition containing the given polynucleotide sequence. The composition may comprise an aqueous solution. Compositions comprising polynucleotide sequences encoding human protein kinase subunit(s) or fragments thereof may be employed as hybridization probes. In this case, the protein kinase subunit-encoding polynucleotide sequences are typically employed in an aqueous solution containing salts (e.g., NaCl), detergents (e.g., SDS) and other components (e.g., Denhardt's solution, dry milk, salmon sperm DNA, etc.).

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "test protein kinase A" refers to a sample suspected of containing protein kinase A. The concentration of protein kinase A in the test sample is determined by various means, and may be compared with a "quantitated amount of protein kinase A" (i.e., a positive control sample containing a known amount of protein kinase A), in order to determine whether the concentration of test protein kinase A in the sample is within the range usually found within samples from wild-type organisms. Thus, comparison of the positive control with the test sample allows the determination to be made whether a particular individual produces a "normal" amount of protein kinase A is deficient in production of protein kinase A, or produces a more than normal concentration of protein kinase A. It is intended that such test methods also contain "negative" controls (i.e., samples that are known to contain no protein kinase A). Furthermore, it is intended that the testing be conducted using the PRKAR1A gene, protein kinase A mRNA, and/or protein kinase A protein (or polypeptides), or fragments of any of these.

The term "test protein kinase A subunit" refers to a sample suspected of containing a particular protein kinase A subunit. The concentration of protein kinase A subunit in the test sample is determined by any suitable means, and may be compared with a "quantitated amount of protein kinase A subunit" (i.e., a positive control sample containing a known amount of the particular protein kinase A subunit), in order to determine whether the concentration of test protein kinase A subunit in the sample is within the range usually found within samples from wild-type organisms. Thus, comparison of the positive control with the test sample allows the determination to be made whether a particular individual produces a "normal" amount of protein kinase A subunit, is deficient in production of protein kinase A subunit, or produces a more than normal concentration of protein kinase A subunit. It is intended that such test methods also contain "negative" controls (i.e., samples that are known to contain no protein kinase A subunit). Furthermore, it is intended that the testing be conducted using any of the protein kinase A subunit genes, protein kinase A mRNA, and/or protein kinase A holoenzyme or subunit protein (or polypeptides), or fragments of any of these.

The present invention further contemplates compositions and methods involving transgenic animals (e.g., rodents) with mutant and wild-type PKA activity.

Experimental

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); BSA (bovine serum albumin); IgG (immunoglobulin G); $H_2O$ (water); HCl (hydrochloric acid); aa (amino acid); bp (base pair); kb (kilobase pair); kD (kilodaltons); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); $\mu$M (micromolar); U (units); V (volts); MW (molecular weight); cM (centimorgan); sec (seconds); min(s) (minute/minutes); hr(s) (hour/hours); $MgCl_2$ (magnesium chloride); NaCl (sodium chloride); $OD_{280}$ (optical density at 280 $\mu$m); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); w/v (weight to volume); v/v (volume to volume); BAC (bacterial artificial chromosome); Amersham (Amersham Life Science, Inc. Arlington Heights, Ill.); Amersham-Pharmacia (Amersham-Pharmacia Biotech, Piscataway, N.J.); ICN (ICN Pharmaceuticals, Inc., Costa Mesa, Calif.); Amicon (Amicon, Inc., Beverly, Mass.); ATCC (American Type Culture Collection, Rockville, Md.); Becton Dickinson (Becton Dickinson Labware, Lincoln Park, N.J.); BioRad (BioRad, Richmond, Calif.); Clontech (Clontech Laboratories, Palo Alto, Calif.); Life Technologies and GIBCO/BRL (Life Technologies, Inc., Gaithersburg, Md.); Varian (Varian, Inc., Woburn, Mass.); Invitrogen (Invitrogen Corp., Carlsbad, Calif.); Kodak (Eastman Kodak Co., New Haven, Conn.); New England Biolabs (New England Biolabs, Inc., Beverly, Mass.); Promega (Promega Corp., Madison, Wis.); Perkin Elmer (Perkin Elmer, Norwalk, Conn.); Roche (Roche Biochemicals, Indianapolis, Ind.); Pierce (Pierce, Rockford, Ill.); BD Transduction (BD Transduction Laboratories, Lexington, Ky.); Genecodes (Genecodes, Ann Arbor, Mich.); AP Biotech (AP Biotech, Piscataway, N.J.); Novagen (Novagen, Inc., Madison, Wis.); Pharmacia (Pharmacia, Inc., Piscataway, N.J.); Qiagen (Qiagen, Valencia, Calif.); Sigma (Sigma Chemical Co., St. Louis, Mo.); Sorvall (Sorvall Instruments, a subsidiary of DuPont Co., Biotechnology Systems, Wilmington, Del.);

Stratagene (Stratagene Cloning Systems, La Jolla, Calif.); Calbiochem (Calbiochem, La Jolla, Calif.); BD Transduction Laboratories (BD Transduction Laboratories, San Diego, Calif.); Genecodes (Genecodes, Ann Arbor, Mich.); and Informax (Informax, Bethesda, Md.

EXAMPLE 1

Patients and Samples

For the experiments described herein, the institutional review boards of NICHD, NIH, and the Mayo Clinic approved the contact of the families and the participation of their members in the NICHD protocol 95-CH-059 after obtaining informed consent.

Patients with CNC were classified as "affected," according to the criteria established by Stratakis et al. (Stratakis et al., Am. J. Med. Genet., 80:183–185 [1998]; and Stratakis et al., J. Clin. Invest., 97:699–705 [1996]). Briefly, individuals considered to be "affected," were all individuals who exhibited two of the following manifestations: lentinginosis and other pigmented skin lesions in a characteristic distribution, myxoma (cardiac, breast, or other), PPNAD, acromegaly, multiple thyroid nodules, LCCSCT or psammomatous melanotic schwannoma. In the analysis of the familial cases, patients that were included as "affected," included those with one of the manifestations listed above and at least one affected first degree kindred. Sporadic cases of the disease were considered to be all patients that had no family history of CNC; when available, first degree relatives of these patients were examined for the presence of CNC stigmata.

Blood and tissue samples were collected from patients belonging to previously described families (See, Stratakis et al., J. Clin. Invest., 97:699–705 [1996]; Danoff et al., Arch. Intern. Med., 143:443–448 [1987]; and Stratakis et al., Am. J. Hum. Genet., 65:A447 [1999]), and sporadic cases. The clinical profile of the patients from family CAR01 (YC01) was reported by Danoff et al. (Danoff et al., supra), while the profiles of the patients of family CAR20 are included in Table 2. Each of the samples was given a two-digit number that reflected its order of collection (e.g., CAR20.03, represents the third specimen collected from the family designated as "CAR.20").

EXAMPLE 2

Microsatellite and Loss-of-Heterozygosity Analysis

Family CAR20, as well as various other families were investigated for segregation of CNC with the polymorphic 17q22–24 markers designated as D17S807, GATA1E12, D17S942, D17S1882, PRKAR1A(CA)n, D17S949, and D17S795, as described (Stratakis et al., J. Clin. Invest., 97:699–705 [1996]; and Stratakis et al., J. Clin. Endocrinol. Metab., 81:3607–3614 [1996]). No recombinations were detected between CAR20 and the 17q22–24 region. Additional markers were typed around loci that could not be read with accuracy, using only the informative members of each family. FIG. 1 shows the pedigree and the affected chromosome 17 in CAR20 (indicated by the boxed alleles). The proband of family CAR20 (CAR20.03) presented with a cardiac myxoma, acromegaly, facial pigmentation, including pigmented spots on his lips and pigmentation at the inner canthus of the eye, a sign that is characteristic of CNC.

Figure 2:
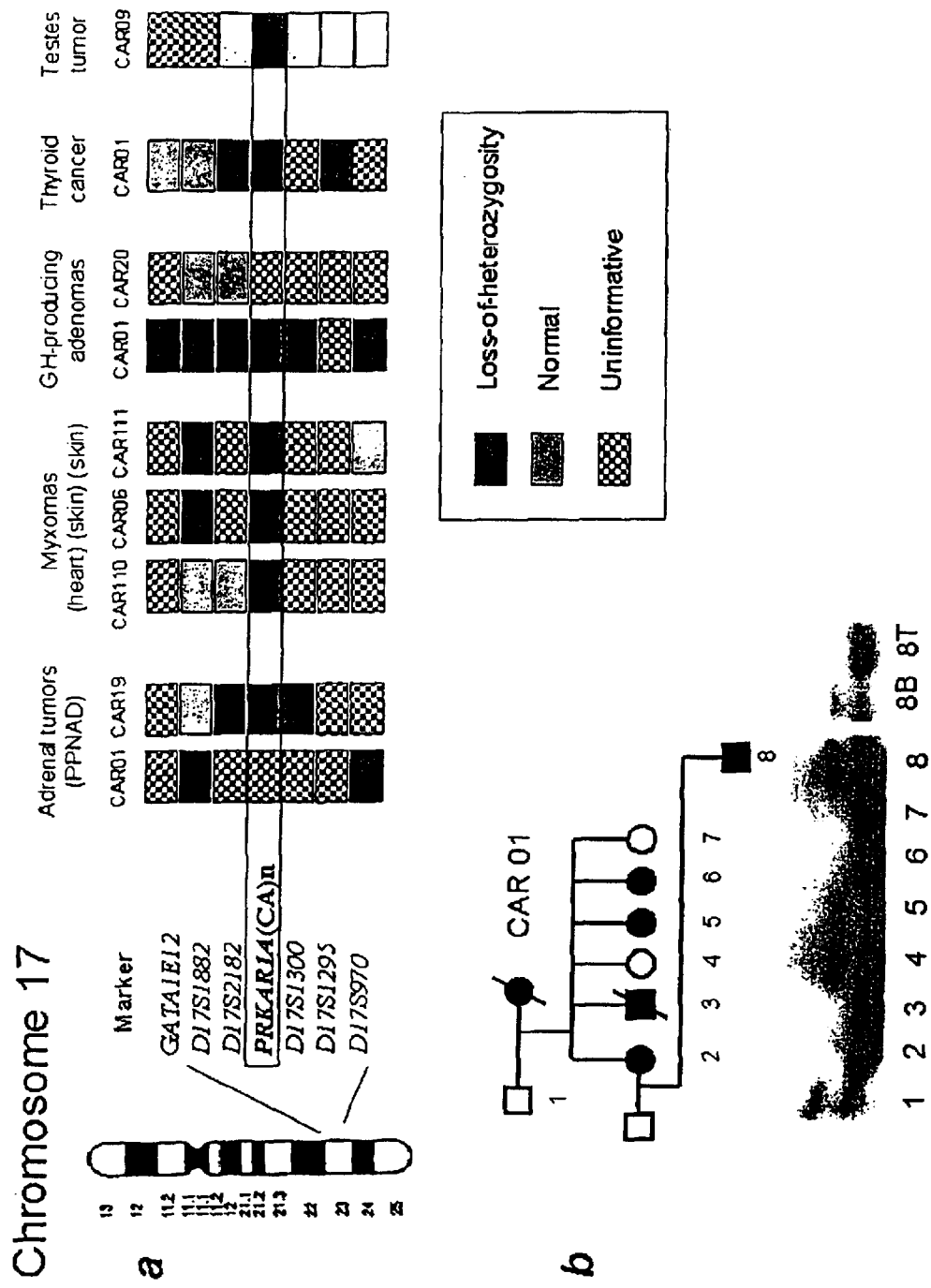
FIG. 2 provides diagrams of the loss-of-heterozygosity data obtained for chromosome 17, near PRKAR1A. In Panel A, data for adrenal tumors (PPNAD), myxomas of the heart and skin, GH-producing adenomas, thyroid cancer, and testicular tumor, are shown. In Panel B, the pedigree of family CAR01 is shown.

For LOH analysis, DNA from CNC tumors was analyzed along with a paired DNA sample from the patient's peripheral blood. Markers located 8 cM around PRKAR1A, including PRKAR1A(CA)n, a dinucleotide repeat from the 5'-region of the gene were used. As indicated in FIG. 2, the tumors included adrenal tumors (PPNAD) from individual CAR01.06 (See, FIG. 2, Panel B) and the proband of family CAR19; myxomas from kindreds CAR110, CAR06, and CAR111; growth hormone-producing pituitary adenomas from CAR01.08 (See, FIG. 2, Panel B, and FIG. 4, Panel A) and CAR20.03; a thyroid follicular carcinoma from CAR01.05; and a testicular tumor (large-cell calcifying Sertoli cell tumor—LCCSCT) from kindred CAR09. The microsatellite alterations seen in the tumors were classified as previously described (Stratakis et al., J. Clin. Endocrinol. Metab., 81:3607–3614 [1996]; and Stratakis et al., J. Clin. Endocrinol. Metab., 83:2972–2976 [1998]). All informative loci demonstrated LOH at the PRKAR1A locus, indicated by the interval between the bars of FIG. 2, Panel A. Samples were considered to be "uninformative," if they demonstrated either homozygosity or microsatellite length instability.

FIG. 2, Panel B shows the pedigree of family CAR01. The marker GATA1E12 has two alleles, with the upper allele clearly being derived from the unaffected father. LOH analysis of the pituitary tumor of CAR01.08 demonstrated loss of the upper allele in the tumor DNA (8T). In this Figure, "8B" refers to DNA from peripheral blood lymphocytes, while "8T" refers to pituitary tumor DNA.

EXAMPLE 3

PRKAR1A Genomic Structure and Primer Design

The presumed cDNA structure of human PRKAR1A was previously reported (Solberg et al., Endocrinol., 138:169–181 [1997]). BLAST analysis of this sequence revealed that exons 3–10 were contained in the RPCI BAC 62_F_10 (GenBank AC005799), although the intron-exon structure predicted from the genomic sequence was different from that described. Primers to amplify these exons were generated from the genomic sequence using the Whitehead Institute's WWW-based program Primer3 (http://www-genome.wi.mit.edu/cgi-bin/primer/primer3.cgi). The 5' of the gene is contained in GenBank Y07641, and the same program was used to select primers to amplify exons 1A and 1B, as well as an apparent CA repeat in the promoter of the gene (PRKAR1A 5' CA). In addition, radiation hybrid mapping was also performed, as known in the art, in order to establish the order of individual STSs (See e.g., Taymans et al., Genomics 56:344–349 [1999]; and Gyapay et al., Hum. Mol. Genet., 5:339–346 [1996]).

The reverse primer for each of the markers was end-labeled with $\gamma$-$^{32}$P-dATP, using T4-polynucleotide kinase (New England Biolabs). Approximately 50 ng of DNA was used in each reaction. The reaction was carried out in a 10 $\mu$L volume containing 1 $\mu$L of DNA solution, 10 pmol of unlabelled primer and dNTPs (1 $\mu$L total volume dilution of all dNTPs, at 10 mmol/L concentration each), 0.1 pmol of labeled primer, in 1.5 mM MgCl PCR buffer (1 mL of 10× PCR buffer), and 1U of Taq polymerase (Perkin-Elmer). Thirty cycles were performed (94° C. for 1 min, 57° C. for 1 min, 72° C. for 30 sec), followed by a final 7 min extension at 72° C. Aliquots of amplified DNA were mixed with an equal volume of loading buffer, denatured at 94° C. for 5 min, and electrophoresed on a 6% polyacrylamide gel (Promega). The dried gel was then exposed to Kodak X-OMAT or BIO-MAX autoradiography film for 16–24 hours.

As discussed in more detail below (See, Example 4), two-point and multipoint LOD scores were calculated using the LINKAGE (version 5.1) computer software, a dominant model of inheritance, 100% penetrance in both sexes and a gene frequency of 0.001, as known in the art (See e.g., Lathrop et al., Proc. Natl. Acad. Sci., 81:3443–3446 [1984]). All marker allele frequencies were calculated using ILINK, also from the LINKAGE suite of programs, as known in the art (See e.g., Stratakis et al., J. Clin. Invest., 97:699–705 [1996]).

The previously reported genomic structure of the PRKAR1A gene (See, Solberg et al., Endocrinol., 138:169–181 [1997]) was revised, based on the comparison of this gene's cDNA (See also, Sandberg et al, Biochem. Biophys. Res. Commun., 149:939–945 [1987]) and available (on line) sequences of genomic clones from the area (http://www.ncbi.nlm.nih.gov/genome/seq/). These changes are indicated in Table 11, below. In this Table, the bold text indicates changes from the intron-exon structure of Solberg et al. (supra). Also, in this Table, exon 4 as described by Solberg et al has been divided into two smaller exons (i.e., 4A and 4B).

TABLE 11

Revised Gene Structure of PRKAR1A

| Exon | Splice Acceptor | Size | Splice Donor |
|---|---|---|---|
| Exon 1A |  | 144 | CAG gta |
| Exon 1B |  | 102 | CAG gtg |
| Exon 2 | cag AGA | 183 | AAG gta |
| Exon 3 | cag GAG | 171 | AAG gta |
| Exon 4A | tag GTT | 92 | AAG gta |
| Exon 4B | cag TGA | 62 | AAG gta |
| Exon 5 | tag GTG | 47 | GAT gta |
| Exon 6 | tag TCT | 159 | ATG gta |
| Exon 7 | tag GGA | 61 | TAG gtg |
| Exon 8 | cag AGT | 122 | GAG gta |

TABLE 11-continued

Revised Gene Structure of PRKAR1A

| Exon | Splice Acceptor | Size | Splice Donor |
|---|---|---|---|
| Exon 9 | tag GGC | 82 | TTG gta |
| Exon 10 | cag GTG |  |  |

A bacterial artificial chromosome (BAC) clone (RPCI 62_F_10) containing exons 3–10 of the gene was identified by screening a commercially available library. Sequencing of this clone and its comparison to PRKAR1A cDNA that was obtained from normal human lymphocytes showed several changes. First, what had previously been considered a single exon (exon 4) actually appeared to be 2 small exons that were located close together; these exons we termed exons 4A and 4B (See, Table 11). Second, there were apparent shifts in some of the previously suggested intron-exon junctions (Solberg et al., Endocrinol., 138:169–181 [1997]); the new boundaries are in compliance with conventional GT-AG rules (Breathnach and Chambon, Ann. Rev. Biochem., 50:349–383 [1981]).

To generate the sequence surrounding the remaining exons and the 5' region of the PRKAR1A gene, an additional BAC was isolated that contained this region of the gene. Direct sequencing of the BAC identified an intronic sequence of relatively small size between exons 2. This BAC also contained exon 3, although it has been previously suggested that a large distance lies between the two exons (See e.g., Solberg et al., Endocrinol., 138:169–181 [1997]). Based on available sequences and those generated during this study, oligonucleotide primers were designed to specifically amplify each exon of the PRKAR1A gene. These primers are shown in Table 12, below. The sequences were then amplified using PCR as described above.

TABLE 12

Primers Used for Amplification of PRKAR1A Exons

| Exon | Size (bp) | Left Primer | SEQ ID NO: | Right Primer | SEQ ID NO: |
|---|---|---|---|---|---|
| 5'(CA)n | 167 | CCCCCACTGTACTGAACACC | SEQ ID NO:1 | CATGGCCACACAGCTAACAT | SEQ ID NO:2 |
| Exon 1A | 284 | AGTCGCCCACCTGTCATCT | SEQ ID NO:3 | CACTTCTCCTTTCCGCAGTC | SEQ ID NO:4 |
| Exon 1B | 254 | CATTGACGTCAGTAGCCGAA | SEQ ID NO:5 | ATCTTGGATCGGTCCAGCTC | SEQ ID NO:6 |
| Exon 2 | 364 | CCTAGTCCCCACTTCCCTGT | SEQ ID NO:7 | ATCACCTCATCATCTCCCCA | SEQ ID NO:8 |
| Exon 3 | 327 | CATGCCGAAGGATCTCATTT | SEQ ID NO:9 | ATGGATGAAGTTCCACCCTG | SEQ ID NO:10 |
| Exon 4A | 397 | CAGGTTGCAAACGTGAAATG | SEQ ID NO:11 | CTGCGATAAAGGAGACCGAA | SEQ ID NO:12 |
| Exon 4B | 362 | AGCCAAAGCCATTGAAAAGA | SEQ ID NO:13 | GCCTCCTCTCCCGTAACAAT | SEQ ID NO:14 |
| Exon 5 | 270 | TTGCTTGATTTTCTTTCCCC | SEQ ID NO:15 | ATTCTTATTGCTCGGAAGCG | SEQ ID NO:16 |
| Exon 6 | 370 | TCATTTAACTCGTCAGAAATCACC | SEQ ID NO:17 | TTCTAAATCACACTCTCAAACACCA | SEQ ID NO:18 |
| Exon 7 | 363 | GGCATAATATTGGCGGAAAA | SEQ ID NO:19 | AAGGCTTTTCCCAAGTCCAT | SEQ ID NO:20 |
| Exon 8 | 331 | AGAATGTTGAATGGGCATGG | SEQ ID NO:21 | TTAGCCCACTCTTTCCCTCTT | SEQ ID NO:22 |
| Exon 9 | 272 | CACCCTGGGTTTGAGAGTGT | SEQ ID NO:23 | TTCCCTCTCAGAGCCAAAAA | SEQ ID NO:24 |
| Exon 10 | 314 | CCCATCTTTGCTTTCTCCAG | SEQ ID NO:25 | AACAGACAGGAAGCTGCGAT | SEQ ID NO:26 |

EXAMPLE 4

Genetic Linkage Analysis

Figure 3:
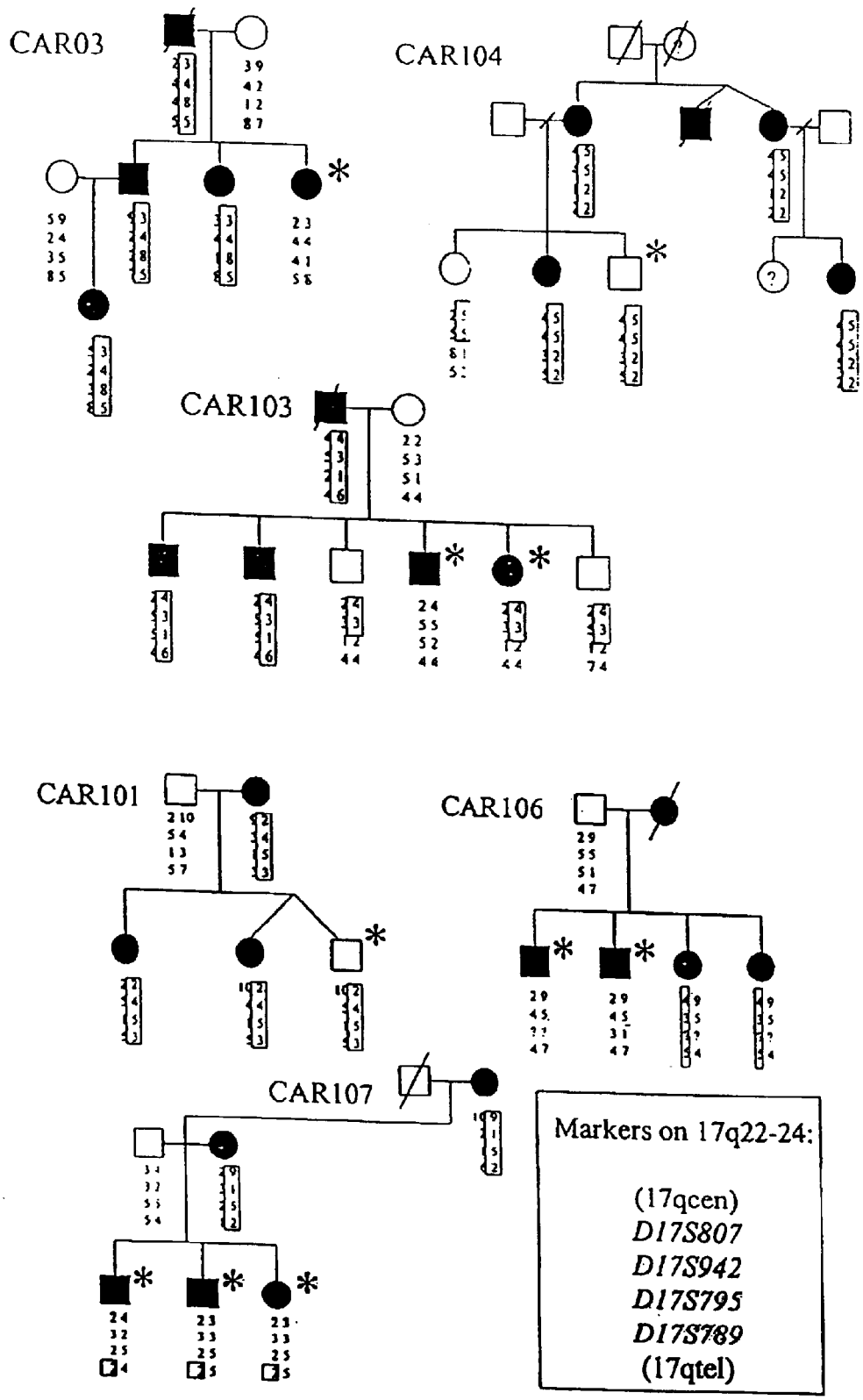
FIG. 3 provides the haplotypes for four markers encompassing the PRKAR1A locus on chromosome 17 (area 17q22–24) of six families with CNC.

Of the 38 kindreds in whom the disease was familial, 14 were informative for linkage analysis. The remaining 24 families were either too small to provide meaningful linkage data or had too many phenotypic uncertainties. To perform linkage studies, each family was analyzed for segregation using markers from 2p16 and 17q22–24 that had previously been shown to lie around the disease locus, respectively as described above (See also, Stratakis et al., J. Clin. Invest., 97:699–705 [1996]; Casey et al., Circul., 98:2560–2566 [1998]). For most of the markers, the locations were confirmed on physical maps of the two areas (Taymans et al., Genomics 56:344–349 [1999]; and Kirschner et al, Genomics 62:21–33 [1999]). In most cases, genetic phase had to be inferred; haplotypes were constructed based on the minimum number of recombinations that would be required to produce each chromosome. FIG. 3 provides the haplotypes for four markers encompassing the PRKAR1A locus on chromosome 17 (area 17q22–24) of six families with CNC. Haplotypes were constructed based on the minimum number of recombinations that would be required to produce each chromosome. Those most likely to segregate with the disease chromosome are indicated in this Figure by boxes. Accordingly, the asterisks indicate recombinations.

This analysis generated four types of families: those that mapped to 17q with recombinations with 2p (chromosome 17 families, N=4), those that mapped to 2p with recombinations with 17q (chromosome 2 families, N=6) (See, FIG. 3), those that had no recombinations with either locus (N=3), and those that had recombinations with both loci (N=1). One family that had previously been thought to map to chromosome 2 was reassigned to the chromosome 17 group after the detection of a PRKAR1A mutation in the family and reassessment of the clinical phenotypes (this is family CAR108 discussed by Stratakis et al. (Stratakis et al., J. Clin. Invest., 97:669–705 [1996]). The error in this kindred arose from inclusion of an apparently unaffected individual with only pigmentation abnormalities from among the various manifestations of CNC; this patient, who also had two unaffected children, was phenotyped as "unaffected" according to the diagnostic criteria discussed above. This patient, however, was found to carry the familial mutation, although neither of his children did.

Owing to the fact that no chromosome 2-mapping family with a LOD score over 3 has been detected to date, there has been discussion whether more than one locus for CNC actually exists. To re-examine this question, LOD score analysis of the 6 families, in whom the disease did not fully segregate with chromosome 17 markers and PRKAR1A mutations were not found (see below) (See, FIG. 3) was performed (Tables 3–8). These families generated positive two-point LOD scores for 2p16 markers. Furthermore, in all families, 17q22–24 could be excluded. Cumulative two-point LOD scores for the 6 families yielded a maximum two-point LOD score of 3.97 at $\theta=0$ for the marker CA-2 at 2p16 (See, Table 10). Multipoint LOD score (MLS) analysis confirmed linkage with 2p16 (maximum MLS of 4.5 for CA-2).

TABLE 4

Two-Point LOD Scores Between CNC and 2p16 and 17q22–24 Markers for CAR03

| | $\theta$ | | | | |
|---|---|---|---|---|---|
| Marker | 0 | 0.1 | 0.2 | 0.3 | 0.4 |
| D2S1352 | 0.9 | 0.72 | 0.52 | 0.32 | 0.13 |
| D2S2156 | 0.9 | 0.72 | 0.52 | 0.32 | 0.13 |
| CA2 | 0.9 | 0.72 | 0.52 | 0.32 | 0.13 |
| D2S2292 | 0 | 0 | 0 | 0 | 0 |
| D2S2153 | −3.1 | −0.19 | 0.01 | 0.07 | 0.06 |
| D17S807 | −3.1 | −0.19 | 0.01 | 0.07 | 0.06 |
| D17S942 | 0 | 0 | 0 | 0 | 0 |
| D17S795 | −3.1 | −0.19 | 0.01 | 0.07 | 0.06 |
| D17S789 | 0.3 | 0.26 | 0.2 | 0.15 | 0.08 |

TABLE 5

Two-Point LOD Scores Between CNC and 2p16 and 17q22–24 Markers for CAR101

| | $\theta$ | | | | |
|---|---|---|---|---|---|
| Marker | 0 | 0.1 | 0.2 | 0.3 | 0.4 |
| D2S1352 | 0.36 | 0.35 | 0.28 | 0.17 | 0.06 |
| D2S2156 | 0.6 | 0.47 | 0.32 | 0.17 | 0.05 |
| CA2 | 0.6 | 0.47 | 0.32 | 0.17 | 0.05 |
| D2S2292 | 0.3 | 0.21 | 0.13 | 0.06 | 0.02 |

TABLE 5-continued

Two-Point LOD Scores Between CNC and 2p16 and 17q22–24 Markers for CAR101

| | $\theta$ | | | | |
|---|---|---|---|---|---|
| Marker | 0 | 0.1 | 0.2 | 0.3 | 0.4 |
| D2S2153 | −inf. | 0.02 | 0.12 | 0.09 | 0.03 |
| D17S807 | −inf. | −0.19 | 0.01 | 0.07 | 0.06 |
| D17S942 | −inf. | −0.44 | −0.19 | −0.08 | −0.02 |
| D17S795 | −inf. | −0.89 | −0.39 | −0.15 | −0.04 |
| D17S789 | −inf. | −0.58 | −0.23 | −0.10 | −0.03 |

TABLE 6

Two-Point LOD Scores Between CNC and 2p16 and 17q22–24 Markers for CAR103

| | $\theta$ | | | | |
|---|---|---|---|---|---|
| Marker | 0 | 0.1 | 0.2 | 0.3 | 0.4 |
| D2S1352 | 1.2 | 0.93 | 0.64 | 0.34 | 0.1 |
| D2S2156 | 1.2 | 0.93 | 0.64 | 0.34 | 0.1 |
| CA2 | 1.2 | 0.93 | 0.64 | 0.34 | 0.1 |
| D2S2292 | 1.2 | 0.94 | 0.66 | 0.37 | 0.12 |
| D2S2153 | 1.51 | 1.23 | 0.92 | 0.58 | 0.21 |
| D17S807 | −0.11 | −0.08 | −0.04 | −0.02 | 0 |
| D17S942 | −inf. | −0.44 | −0.19 | −0.08 | −0.02 |
| D17S795 | −inf. | −0.14 | −0.01 | 0.01 | 0.01 |
| D17S789 | −3.1 | −0.44 | −0.19 | −0.08 | −0.02 |

TABLE 7

Two-Point LOD Scores Between CNC and 2p16 and 17q22–24 Markers for CAR104

| | $\theta$ | | | | |
|---|---|---|---|---|---|
| Marker | 0 | 0.1 | 0.2 | 0.3 | 0.4 |
| D2S1352 | −inf. | −0.09 | 0.02 | 0.03 | 0.01 |
| D2S2156 | 0.84 | 0.63 | 0.42 | 0.22 | 0.06 |
| CA2 | 0.84 | 0.63 | 0.42 | 0.22 | 0.06 |
| D2S2292 | 0.51 | 0.36 | 0.22 | 0.11 | 0.03 |
| D2S2153 | −3.77 | −0.58 | −0.24 | −0.08 | −0.02 |
| D17S807 | −inf. | −0.26 | −0.08 | −0.02 | 0 |
| D17S942 | −0.23 | −0.08 | −0.03 | −0.01 | 0 |
| D17S795 | −inf. | −0.06 | 0.04 | 0.04 | 0.01 |
| D17S789 | 0.25 | 0.18 | 0.11 | 0.05 | 0.01 |

TABLE 8

Two-Point LOD Scores Between CNC and 2p16 and 17q22–24 Markers for CAR106

| | $\theta$ | | | | |
|---|---|---|---|---|---|
| Marker | 0 | 0.1 | 0.2 | 0.3 | 0.4 |
| D2S1352 | 0.4 | 0.29 | 0.19 | 0.09 | 0.03 |
| D2S2156 | 0.58 | 0.43 | 0.28 | 0.14 | 0.04 |
| CA2 | 0.43 | 0.32 | 0.21 | 0.1 | 0.03 |
| D2S2292 | 0.35 | 0.25 | 0.16 | 0.08 | 0.02 |
| D2S2153 | −3.1 | −0.44 | −0.19 | −0.08 | −0.02 |
| D17S807 | −3.1 | −0.44 | −0.19 | −0.08 | −0.02 |
| D17S942 | −3.1 | −0.44 | −0.19 | −0.08 | −0.02 |
| D17S795 | −3.1 | −0.44 | −0.19 | −0.08 | −0.02 |
| D17S789 | −3.1 | −0.44 | −0.19 | −0.08 | −0.02 |

TABLE 9

Two-Point LOD Scores Between CNC and 2p16 and 17q22–24 Markers for CAR107

| Marker | θ | | | | |
|---|---|---|---|---|---|
| | 0 | 0.1 | 0.2 | 0.3 | 0.4 |
| D2S1352 | 0 | 0 | 0 | 0 | 0 |
| D2S2156 | -inf. | -0.19 | 0.01 | 0.07 | 0.06 |
| CA2 | 0.6 | 0.47 | 0.32 | 0.17 | 0.05 |
| D2S2292 | 0.6 | 0.47 | 0.32 | 0.17 | 0.05 |
| D2S2153 | 0.9 | 0.77 | 0.61 | 0.44 | 0.24 |
| D17S807 | -inf. | -2.1 | -1.19 | -0.67 | -0.29 |
| D17S942 | -inf. | -2.1 | -1.19 | -0.67 | -0.29 |
| D17S795 | -inf. | -2.1 | -1.19 | -0.67 | -0.29 |
| D17S789 | 0.90 | 0.77 | 0.61 | 0.44 | 0.24 |

TABLE 10

Aggregate Two-Point LOD Scores Between CNC and Markers for Six Families With at Least One Recombination with 17q22-24

| Marker | θ | | | |
|---|---|---|---|---|
| (2ptel-2pcen) | 0 | 0.1 | 0.2 | 0.3 |
| D2S1352 | -inf. | 2.2 | 1.65 | 0.95 |
| D2S2156 | -inf. | 2.99 | 2.19 | 1.26 |
| CA2 | 3.97 | 3.07 | 2.11 | 1.15 |
| D2S2292 | 2.96 | 2.23 | 1.49 | 0.79 |
| D2S2153 | -inf. | 1.02 | 1.38 | 1.09 |

Thus, the data indicate that there is genetic heterogeneity in CNC. The finding of a large CNC family (maximum simulated two-point LOD score of 1.8 with hypothesis of linkage to a putative locus) with at least one recombination with 2p 16 markers, in whom no PRKAR1A mutation could be found and the 17q22–24 locus could be firmly excluded (family CAR102 in Stratakis et al., J. Clin. Invest., 97:699–705 [1996]), confirms heterogeneity but does not support the existence of a 2p16 locus. On the other hand, the findings of CNC tumor genetic changes involving genomic material from 2p16 is supportive of a second CNC gene located in that locus. Thus, it is contemplated that there is a second CNC gene located at approximately 2p16.

As part of the genetic analysis of CNC kindreds, the possibility of a founder effect, especially in those families that shared a common PRKAR1A mutation (see below) or those that came from geographically proximal areas was also examined. As haplotype analysis could not confirm a common origin of the linking chromosome, it is contemplated that at least for the PRKAR1A gene, each family represents a de novo mutational event, and is consistent with the relatively large number of sporadic cases of CNC. Nonetheless, the present invention provides methods and compositions for the detection of such cases.

EXAMPLE 5

Denaturing HPLC Analysis

In this Example, experiments to investigate the heterozygosity of all 53 kindreds screened for any mutations in any of the exons of the PRKAR1A gene were analyzed. DNA samples from patients and unaffected family members PCR-amplified in 30 μl volumes, as described in Example 4, above. Ten μl samples were injected into a DHPLC instrument (HELIX, Varian, Inc.) at column temperatures recommended by the DHPLC Melt program (http://insertion.stanford.edu/melt.html), as known in the art (See, O'Donovan et al., Genomics 52:44–49 [1998]; and Jones et al, Clin. Chem., 45:1133–1140 [1999]). The samples were then analyzed as described in Example 6.

EXAMPLE 6

Analysis of Mutations

In heteroduplex samples detected as described in Example 5, the remaining 20 μl was purified and sequenced using BigDye Terminators (Perkin-Elmer) on an ABI 377 fluorescent sequencer, as known in the art. The sequence traces were analyzed using either Sequencher (Genecodes) or Vector NTI (Informax). In cases where the sequence change appeared to be a frameshift or were unclear, PCR samples were subjected to TOPO-TA cloning (Invitrogen) and sequencing of the plasmids contained in individual colonies was conducted.

Mutations were detected in 16 kindreds, in addition to the seven that were previously identified during the development of the present invention. In 10 of the newly identified kindreds, the PRKAR1A mutation segregated with CNC in more than one family member, while in 5 kindreds, the mutation was only found in the proband (i.e., sporadic cases).

As indicated in FIG. 4, a frameshift mutation was detected in CAR01 in PRKAR1A exon 4B. Members of family CAR01 were analyzed for the presence of heteroduplexes in exon 4B, using denaturing HPLC (DHPLC) analysis. An alteration in the peak shape of CAR01.08 was observed, which is indicative of heteroduplex formation (heterozygosity). Heteroduplex DNA, with the identified change was subsequently cloned for clarification of the sequencing defect. The colonies were selected and sequenced, revealing the presence of a two base pair deletion in the mutant form of the sequence (578delTG). In addition, a sequence alteration was observed in the proband's genomic DNA. In addition, it appeared that in the entire cohort of CNC families, two additional kindreds shared this mutation in exon 4B, without sharing common 17q22–24 allelotypes. Thus, 578delTG is the most common PRKAR1A mutation that arises independently in CNC kindreds that carry it. This "hot spot" in the PRKAR1A gene may be the result of a "TGTG" sequence pattern present at the deletion site.

The only other PRKAR1A mutations that appeared to have arisen de novo in more than one kindreds with CNC were: 1) a nonsense point mutation in exon 2 (C211T) that was found in 2 kindreds; and 2) a G-to-C transversion in the 5' splice site of intron 3 of the PRKAR1A gene (exon 3 IVS+lG>C) that was also found in 2 kindreds (See, Table 13).

Of the remaining 13 mutations, each represents a unique mutation (Table 13). These mutations have been detected throughout the coding region of the PRKAR1A cDNA and involve every exon except exons 4A and 10. It is interesting to note that PRKAR1A mutations tend to cluster in certain exons, with the majority of mutations in exons 2 (N=5) and 6 (N=4). On the other hand, 4B is the most commonly mutated exon of the PRKAR1A gene, albeit with a single genetic defect (578delTG) accounting for all mutations (N=6) identified to date in that exon. Thus, it is contemplated that exons 2 and 6 harbor many of the mutations, as these are the largest and third-largest exons of PRKAR1A, respectively. However, it was unexpected that the second largest exon, exon 3, has not been found to be mutated in any families.

With the exception of the 88A>G mutation, which changes the initiator ATG to a GTG codon, each of the mutations detected in this study is predicted to lead to a premature termination codon. Each of the 6 point mutations (including the 2 bp change in CAR13) encodes a nonsense mutation. The frameshift mutations also lead to the generation of missense residues, followed by an early termination codon. While the effects of the four splice site mutations on the protein coding potential of their respective messages have not been fully elucidated yet, it is contemplated that a similar phenomenon will be observed.

Penetrance of CNC in kindreds carrying PRKAR1A mutations appears to be close to 100% (over 97%), because only one of 48 mutation carriers (2.08%) (one individual in family CAR108) did not fully meet the diagnostic criteria. However, penetrance of the disease per age group, remains to be accurately estimated, after extended family members are screened for PRKAR1A mutations. In addition, because more than half of the examined kindreds did not harbor PRKAR1A mutations, it cannot be assumed that this estimate of penetrance applies to kindreds with CNC caused by other genetic defects.

Figure 5:
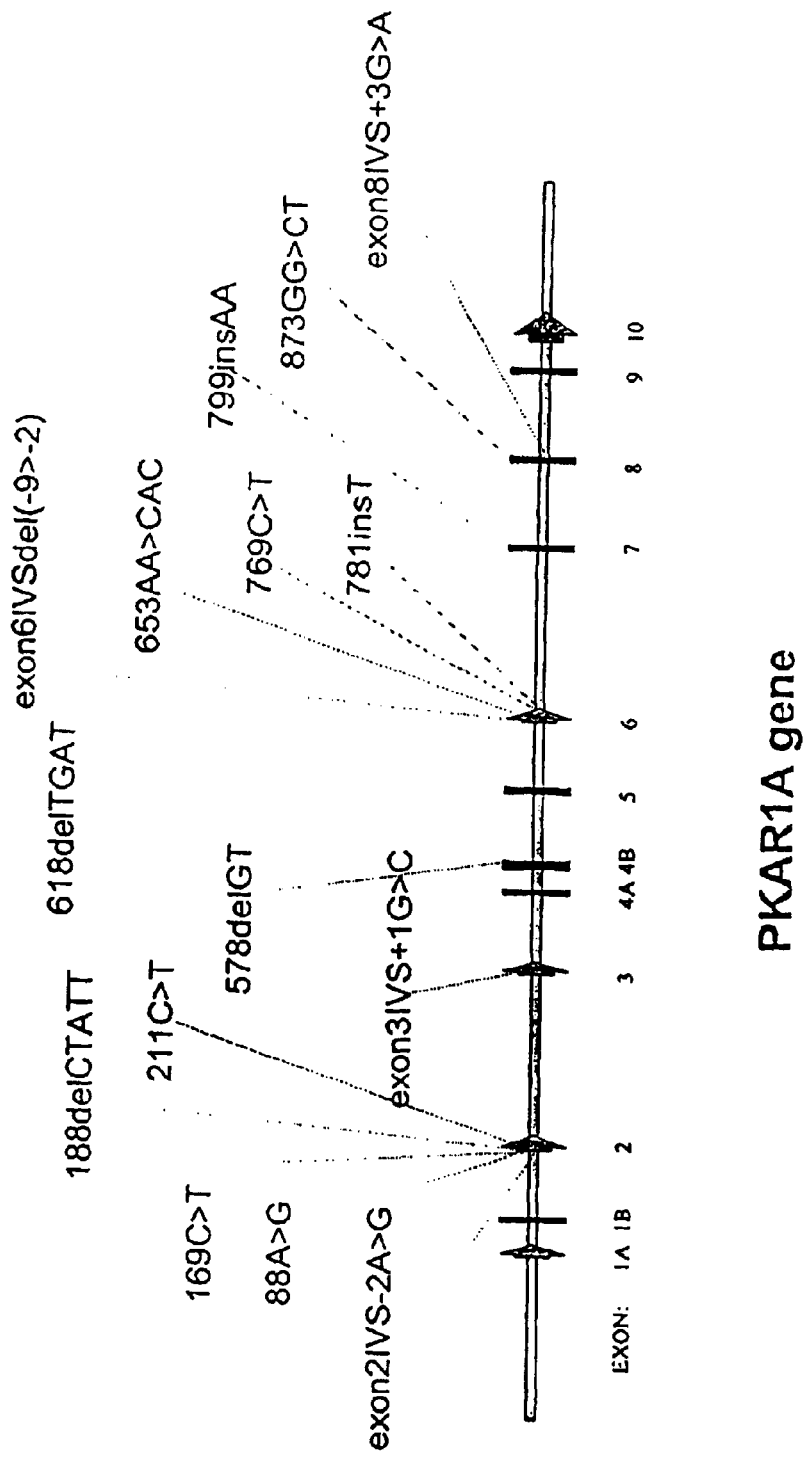
FIG. 5 provides the structure of the PRKAR1A gene and indicates the locations of the mutations identified during the development of the present invention.
Figure 6:
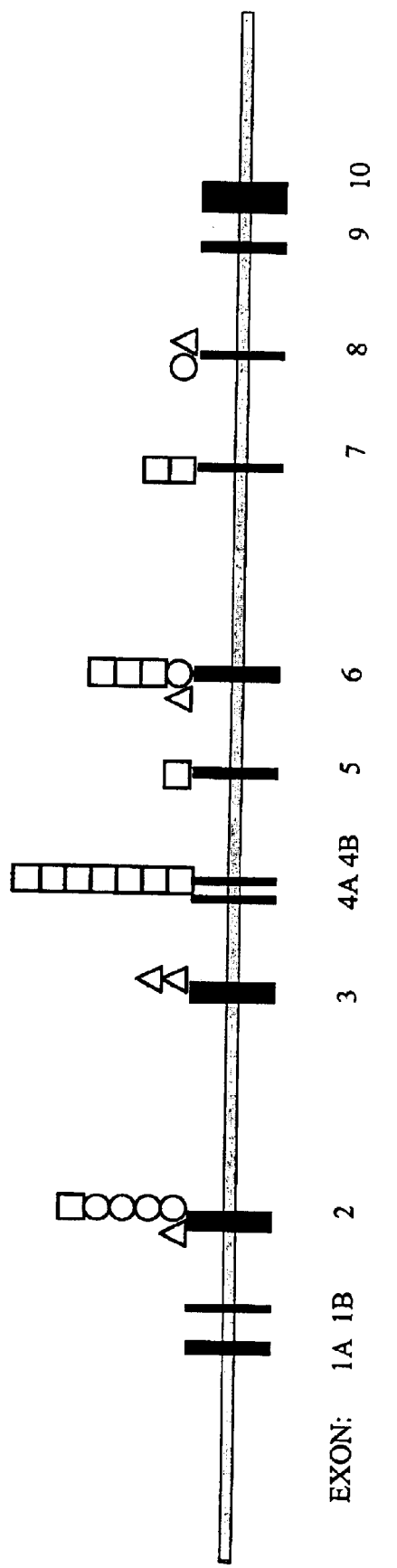
FIG. 6 provides a schematic of the gene structure and locations of mutations in PRKAR1A in patients with CNC. The structure of the PRKAR1A gene is shown, with the locations of the exons as indicated. Each symbol represents one family unit (kindred or sporadic case) with a mutation in that location. Circles indicate nonsense mutations, squares indicate frameshifts, and triangles indicate splice site mutations. Each of the mutations in exon 4B represents the same two base pair deletion. One of the exon 2 nonsense mutations and the exon 3 splice site mutation are indicated in two kindreds each, whereas all other mutations are unique.

Table 13 below, provides a comprehensive list of all PRKAR1A mutations identified in these kindreds and their relative frequencies. The locations of these genetic defects are shown in FIG. 5.

TABLE 13

Mutations of the PRKAR1A Gene in Patients with Carney Complex

| Mutations | Exon | No. of Alleles | Effect | Frequency |
|---|---|---|---|---|
| Point Mutations | | | | |
| 88A > G | 2 | 1 | Abolishes initiator ATG | 4.3 |
| 169C > T | 2 | 1 | Nonsense | 4.3 |
| 211C > T | 2 | 2 | Nonsense | 8.6 |
| 769C > T | 6 | 1 | Nonsense | 4.3 |
| 873GG > CT | 8 | 1 | Missense/Nonsense | 4.3 |
| 1007C > G | 9 | 1 | Nonsense | 4.3 |
| Frameshift Mutations | | | | |
| 188delCTATT | 2 | 1 | Frameshift/stop | 4.3 |
| 578delTG | 4B | 6 | Frameshift/stop | 26.1 |
| 618delTGAT | 5 | 1 | Frameshift/stop | 4.3 |
| 653AA > CAC | 6 | 1 | Frameshift/stop | 4.3 |
| 781insT | 6 | 1 | Frameshift/stop | 4.3 |
| 799insAA | 7 | 1 | Frameshift/stop | 4.3 |
| Splice Site Mutations | | | | |
| exon 2 IVS − 2A > G | | 1 | Disrupts splice acceptor site | 4.3 |
| exon 3 IVS + 1G > C | | 2 | Disrupts splice donor site | 8.6 |
| exon 6 | | 1 | Disrupts splice | 4.3 |

TABLE 13-continued

Mutations of the PRKAR1A Gene in Patients with Carney Complex

| Mutations | Exon | No. of Alleles | Effect | Frequency |
|---|---|---|---|---|
| IVS del(−9 > −2) exon 8 IVS + 3G > A | | 1 | acceptor site Disrupts splice donor site | 4.3 |
| Total: | | 23 | Premature truncation of protein | 100 |

During the development of the present invention, the presence of three PRKAR1A polymorphisms, which did not appear to segregate with CNC in the families in whom the disease mapped to 17q22–24 were also detected. These are shown below in Table 14. In this Table, the numbering is relative to the start of exon 1A, which is absent in the reference sequence for PRKAR1A (i.e., Solberg et al., Endocrinol., 138:169–181 [1997]).

TABLE 14

Location of Polymorphic Sites Within the PRKAR1A Gene

| Exon | Sequence Change | Effect |
|---|---|---|
| 1A | 109 A/C | 5' UTR |
| 2 | 174 G/A | Ala (no change) |
| 8 | IVS − 27 G/A | Intronic |

It is contemplated that these single-nucleotide polymorphisms (SNPs), which were either located in intronic sequences (A109C and exon 8 IVS -G27A) or did not change the coded amino acid (G174A) will find use in linkage studies of CNC families, as they appear to be commonly present in the general population. For example, analysis of the intron 7 G/A polymorphism in family members from the CAR03 and CAR103 kindreds (that are included in Tables 3 and 5, as potentially mapping to 2p16) confirmed the lack of segregation of the PRKAR1A gene with the CNC phenotype in these families. The other families that are included in Tables 1, 2, 4, and 6, were uninformative for the PRKAR1A SNPs. In addition, the presence of a PRKAR1A pseudogene on chromosome 1 did not interfere with mutational analysis of the functional PRKAR1A gene on chromosome 17, because its sequence could not be detected by the methods used above. The following section includes the exons of the R1A gene, including the exons (uppercase) and introns (lower case). The asterisk signifies the normal translation termination (stop) codon for the protein.

```
Exon 2
Wild-type Exon 2 has the following sequence: cagAGAACCA TGGAGTCTGG
CATGACCGCC GCCAGTGAGG AGGCACGCAG CCTTCGAAGA TGTGAGCTCT
ACGTCCAGAA GCATAACATT CAAGCGCTGC TCAAAGATTC TATTGTGCAG
TTGTGCACTG CTCGAGGTGA GAGACCCATG GCATTCCTCA GGGAATACTT
TGAGAGGTTG GAGAAGgta (SEQ ID NO:27).

The amino acid corresponding to this wild-type sequence is: MESGSTAASE
EARSLRECEL YVQKHNIQAL LKDSIVQLCT ARPERPMAFL REYFERLEK (SEQ ID NO:28).

One mutant (Exon 2 IVS-2A>G) has the following sequence: cggAGAACCA
TGGAGTCTGG CAGTACCGCC GCCAGTGAGG AGGCACGCAG CCTTCGAAGA
```

```
                              -continued
TGTGAGCTCT ACGTCCAGAA GCATAACATT CAAGCGCTGC TCAAAGATTC
TATTGTGCAG TTGTGCACTG CTCGACCTGA GAGACCCATG GCATTCCTCA
GGGAATACTT TGAGAGGTTG GAGAAGgta (SEQ ID NO:29).

Another mutant (88A>G) has the following sequence: cagAGAACCG
TGGAGTCTGG CAGTACCGCC GCCAGTGAGG AGGCACGCAG CCTTCGAAGA
TGTGAGCTCT ACGTCCAGAA GCATAACATT CAAGCGCTGC TCAAAGATTC
TATTGTGCAG TTGTGCACTG CTCGACCTGA GAGACCCATG GCATTCCTCA
GGGAATACTT TGAGAGGTTG GAGAAGgta (SEQ ID NO:30).

Another mutant (169C>T) has the following sequence: cagAGAACCA
TGGAGTCTGG CAGTACCGCC GCCAGTGAGG AGGCACGCAG CCTTCGAAGA
TGTGAGCTCT ACGTCCAGAA GCATAACATT TAAGCGCTGC TCAAAGATTC
TATTGTGCAG TTGTGCACTG CTCGACCTGA GAGACCCATG GCATTCCTCA
GGGAATACTT TGAGAGGTTG GAGAAGgta (SEQ ID NO:31).

Another mutant (188delCTATT) has the following sequence: cagAGAACCA
TGGAGTCTGG CAGTACCGCC GCCAGTGAGG AGGCACGCAG CCTTCGAAGA
TGTGAGCTCT ACGTCCAGAA GCATAACATT CAAGCGCTGC TCAAAGATT
GTGCAG TTGTGCACTG CTCGACCTGA GAGACCCATG GCATTCCTCA
GGGAATACTT TGAGAGGTTG GAGAAGgta (SEQ ID NO:32).

Another mutant (211C>T) has the following sequence: cagAGAACCA
TGGAGTCTGG CAGTACCGCC GCCAGTGAGG AGGCACGCAG CCTTCGAAGA
TGTGAGCTCT ACGTCCAGAA GCATAACATT CAAGCGCTGC TCAAAGATTC
TATTGTGCAG TTGTGCACTG CTTGACCTGA GAGACCCATG GCATTCCTCA
GGGAATACTT TGAGAGGTTG GAGAAGgta (SEQ ID NO:33).

Exon 3
Wild-type Exon 3 has the following sequence: cagGAGGAGG
CAAAACAGAT TCAGAATCTG CAGAAAGCAG GCACTCGTAC AGACTCAAGG
GAGGATGAGA TTTCTCCTCC TCCACCCAAC CCAGTGGTTA AAGGTAGGAG
GCGACGAGGT GCTATCAGCG CTGAGGTCTA CACGGAGGAA GATGCGGCAT
CCTATGTTAG AAAGgtagtt (SEQ ID NO:34).

The amino acid sequence encoded by this wild-type sequence is:
EEAKQIQNLQ KAGTRTDSRE DEISPPPPNP VVKGRRRRGA ISAEVYTEED
AASYVRK (SEQ ID NO:35).

One mutant (Exon3 IVS+1G>C) has the following sequence: cagGAGGAGG
CAAAACAGAT TCAGAATCTG CAGAAAGCAG GCACTCGTAC AGACTCAAGG
GAGGATGAGA TTTCTCCTCC TCCACCCAAC CCAGTGGTTA AAGGTAGGAG
GCGACGAGGT GCTATCAGCG CTGAGGTCTA CACGGAGGAA GATGCGGCAT
CCTATGTTAG AAAGctagtt (SEQ ID NO:36).

Exon 4A
Wild-type Exon 4A has the following sequence: agGTTATACC
AAAAGATTAC AAGACAATGG CCGCTTTAGC CAAAGCCATT GAAAAGAATG
TGCTGTTTTC ACATCTTGAT GATAATGAGA GAAGgtagga (SEQ ID NO:37).

The amino acid sequence encoded by this wild-type sequence is:
VIPKDYKTMA ALAKAIEKNV LFSHLDDNLR S (SEQ ID NO:38).

Exon 4B
Wild-type Exon 4B has the following sequence: cagTGATATT
TTTGATGCCA TGTTTTCGGT CTCCTTTATC GCAGGAGAGA
CTGTGATTCAGCAAGgtaag (SEQ ID NO:39).

The amino acid sequence encoded by this wild-type sequence is:
DIFDAMFSVS FIAGETVIQQ G (SEQ ID NO:40).

One mutant (578delTG) has the following sequence: cagTGATATT
TTTGATGCCA TGTTTTCGGT CTCCTTTATC GCAGGAGAGA CTGTATTCA
GCAAGgtaag (SEQ ID NO:41).

Exon 5
Wild-type Exon 5 has the following sequence: ctcttttagG TGATGAAGGG
GATAACTTCT ATGTGATTGA TCAAGGAGAG ACGGATgtaa (SEQ ID NO:42).

The amino acid sequence encoded by this wild-type sequence is:
DEGDNFYVID QGETD (SEQ ID NO:43).

One mutant Exon 5 (618del TGAT) has the following sequence: ctcttttagG
TGATGAAGGG GATAACTTCT ATGTGAT CAAGGAGAG ACGGATgtaa (SEQ ID NO:44).

Exon 6
Wild type Exon 6 has the following sequence: ttgatgtcac ttgcacttta
gGTCTATGTT AACAATGAAT GGGCAACCAG TGTTGGGGAA GGAGGGAGCT
TTGGAGAACT TGCTTTGATT TATGAACAC CGAGAGCAGC CACTGTCAAA
GCAAAGACAA ATGTGAAATT GTGGGGCATC GACCGAGACA
```

GCTATAGAAG AATCCTCATG gta (SEQ ID NO:45).

The amino acid sequence encoded by this wild-type sequence is:
VYVNNEWATS VGEGGSFGEL ALIYGTPRAA TVKAKTNVKL WGIDRDSYRR
ILM (SEQ ID NO:46).

One mutant Exon 6 (Exon 6 IVSdel (-9>-2) has the following sequence:
ttgatgtcac tt gGTCTATGTT AACAATGAAT GGGCAACCAG TGTTGGGGAA
GGAGGGAGCT TTGGAGAACT TGCTTTGATT TATGGAACAC CGAGAGCAGC
CACTGTCAAA GCAAAGACAA ATGTGAAATT GTGGGGCATC GACCGAGACA
GCTATAGAAG AATCCTCATG gta (SEQ ID NO:47).

Another mutant Exon 6 (653AA>CAC) has the following sequence: ttgatgtcac
ttgcacttta gGTCTATGTT AACCACTGAAT GGGCAACCAG TGTTGGGGAA
GGAGGGAGCT TTGGAGAACT TGCTTTGATT TATGGAACAC CGAGAGCAGC
CACTGTCAAA GCAAAGACAA ATGTGAAATT GTGGGGCATC GACCGAGACA
GCTATAGAAG AATCCTCATG gta (SEQ ID NO:48).

Another mutant Exon 6 (769C>T) has the following sequence: ttgatgtcac
ttgcacttta gGTCTATGTT AACAATGAAT GGGCAACCAG TGTTGGGGAA
GGAGGGAGCT TTGGAGAACT TGCTTTGATT TATGGAACAC CGAGAGCAGC
CACTGTCAAA GCAAAGACAA ATGTGAAATT GTGGGGCATC GACTGAGACA
GCTATAGAAG AATCCTCATG gta (SEQ ID NO:49).

Another mutant Exon 6 (781insT) has the following sequence: ttgatgtcac
ttgcacttta gGTCTATGTT AACAATGAAT GGGCAACCAG TGTTGGGGAA
GGAGGGAGCT TTGGAGAACT TGCTTTGATT TATGGAACAC CGAGAGCAGC
CACTGTCAAA GCAAAGACAA ATGTGAAATT GTGGGGCATC GACCGAGACA
GCTATTAGAAG AATCCTCATG gta (SEQ ID NO:50).

Exon 7
Wild-type Exon 7 has the following sequence: tatttttagG GAAGCACACT
GAGAAAGCGG AAGATGTATG AGGAATTCCT TAGTAAAGTC TCTATTTTAG
gtgagttgta (SEQ ID NO:51).

The amino acid sequence encoded by this sequence is: GSTLRKRKMY
EEFLSKVSIL E (SEQ ID NO:52).

One mutant Exon 7 (799insAA) has the following sequence: tatttttagG
GAAAAGCACACT GAGAAAGCGG AAGATGTATG AGGAATTCCT
TAGTAAAGTC TCTATTTTAG gtgagttgta (SEQ ID NO:53).

Exon 8
Wild-type exon 8 has the following sequence: gtctttcagA GTCTCTGGAC
AAGTGGGAAC GTCTTACGGT AGCTGATGCA TTGGAACCAG TGCAGTTTGA
AGATGGGCAG AAGATTGTGG TGCAGGGAGA ACCAGGGGAT GAGTTCTTCA
TTATTTTAGA Ggtaaagaac (SEQ ID NO:54).

The amino acid encoded by this sequence is: SLDKWERLTV ADALEPVQFE
DGQKIVVQGE PGDEFFIILE (SEQ ID NO:55).

One mutant exon 8 (873 GG>CT) has the following sequence: gtctttcagA
GTCTCTGGAC AAGTGCTAAC GTCTTACGGT AGCTGATGCA TTGGAACCAG
TGCAGTTTGA AGATGGGCAG AAGATTGTGG TGCAGGGAGA
ACCAGGGGAT GAGTTCTTCA TTATTTTAGA Ggtgaagaac (SEQ ID NO:56).

Another mutant exon 8 (exon 8 IVS+3A>G) has the following sequence:
gtctttcagA GTCTCTGGAC AAGTGGGAAC GTCTTACGGT AGCTGATGCA
TTGGAACCAG TGCAGTTTGA AGATGGGCAG AAGATTGTGG TGCAGGGAGA
ACCAGGGGAT GAGTTCTTCA TTATTTTAGA Ggtaaagaac (SEQ ID NO:57).

Exon 9
Wild-type exon 9 has the following sequence: ttattatagG GGTCAGCTGC
TGTGCTACAA CGTCGGTCAG AAAATGAAGA GTTTGTTGAA GTGGGAAGAT
TGGGGCCTTC TGATTATTTT Ggtatgtatg (SEQ ID NO:58).

The amino acid encoded by this sequence is: GSAAVLQRRS ENEEFVEVGR
LGPSDYF (SEQ ID NO:59).

A mutant exon 9 (1007C>G) has the following sequence: ttaffatagG
GGTCAGCTGC TGTGCTACAA CGTCGGTGAG AAAATGAAGA GTTTGTTGAA
GTGGGAAGAT TGGGGCCTTC TGATTATTTT Ggtatgtatg (SEQ ID NO:60).

Exon 10
Wild-type exon 10 has the following sequence: ctccaGGTGA AATTGCACTA
CTGATGAATC GTCCTCGTGC TGCCACAGTT GTTGCTCGTG GCCCCTTGAA
GTGCGTTAAG CTGGACCGAC CTAGATTTGA ACGTGTTCTT GGCCCATGCT
CAGACATCCT CAAACGAAAC ATCCAGCAGT ACAACAGTTT TGTGTCACTG
TCTGTCTGAA ATCTGCCTCC TGTGCCTCCC TTTTCTCCTC TCCCCAATCC
ATGCTTCACT CATGCAAACT GCTTTATTTT CCCTACTTGC AGCGCAAGT

```
                        -continued
GGCCACTGGC ATCGCAGCTT CCTGTCTGTT TATATATTGA AAGTTGCTTT
TATTGCACCA TTTTCAATTT GGAGCATTAA CTAAATGCTC ATACACAGTT
AAATAAA (SEQ ID NO:61).
```

The amino acid encoded by this sequence is: GEIALLMNRP RAATVVARGP LKCVKLDRPR FERVLGPCSD ILKRNIQQYN SFVSLSV (SEQ ID NO:62).

Summary of Results

Thus, in these experiments described above, 10 families were fully mapped to the chromosome 17 locus. With the exception of one family, for whom insufficient amounts of DNA were available to complete the analysis, each of these families was found to have a mutation of PRKAR1A gene. In contrast, none of the families exhibiting recombination with 17q was found to have a mutation, indicating that genetic linkage analysis was able to correctly identify the families in whom a mutation search was worthwhile. This observation supports the utility of the methods and compositions of the present invention in identifying families to screen for PRKR1A.

In total, 36 familial cases of CNC were evaluated, and 16 were found to carry PRKAR1A mutations (44.4%). Similarly, 6/17 (35.3%) of sporadic CNC patients were found to have mutations in that gene. Assuming that 5–10% of mutations may be undetectable by commonly used means of screening, this would suggest that PRKAR1A mutations would be expected to account for up to ½ of patients with CNC, although the real number may be closer to 35–40%. Thus, the present invention provides advantages over the presently used methods.

EXAMPLE 7

PKA Activity

PKA activity was measured as described previously (Cho et al., Proc. Natl. Acad. Sci. USA 97:837–840 [2000]; and Kuo et al., Biochem. Biophys. Acta 212:79–91 [1970]) in cell extracts from six CNC tumors (3 PPNAD, 1 ovarian tumor, and 2 schwannomas) and four non-CNC tumors (3 adrenocortical adenomas and 1 meningioma). All of the CNC tumors were from individuals known to contain mutations in PRKAR1A. Activity was compared separately in the tumors from steroid-producing tissues (3 PPNAD and 1 ovarian tumor from CNC patients versus 3 adrenal adenomas from non-CNC patients) and the CNS tumors (2 schwannomas from CNC tumors versus 1 meningioma from a non-CNC patient).

Briefly, the protein extracts were prepared from the above tumors by standard methods known in the art. After homogenization, the PKA activity was measured in assays containing 10 $\mu$g of protein cell extract, 50 mM Tris-HCl (pH 7.5), 1 mM DTT, 10 mM $MgCl_2$, 5 $\mu$M Kemptide (A Ser peptide: Leu-Arg-Arg-Ala-Ser-Leu-Gly; GIBCO/BRL); 1.2 $\mu$M [$\gamma^{32}$P]ATP (25 Ci/mmol; ICN), with or without 5 $\mu$M cAMP (total volume of 50 $\mu$l) for 5 minutes at 30° C. After incubation, the reaction mixtures were spotted onto phosphocellulose disks (GIBCO/BRL) and washed three times in 0.5% phosphoric acid. The filters were air-dried and then counted using a liquid scintillation counter.

One unit of PKA activity was defined as that amount of enzyme that transferred 1 pmol of $^{32}$P from [$\gamma$-$^{32}$P]ATP to recovered protein in 1 minute at 30°/37° C. in the standard assay system. The PKA activity ratio was calculated using the formula known in the art (See, Cho et al., Proc. Natl. Acad. Sci. USA 97:835–840 [2000]). All determinations of PKA activity were done twice for each tumor and an average value was calculated for each experiment. Data from all tumors were compared with the STATISTICA software (StatSoft, Inc.) using the t-test for individual comparisons; a p value of less than 0.05 was considered significant.

EXAMPLE 8

Protein Preparation and Western Blotting

Primary cultured cells from the pituitary tumor of individual 20.03 were maintained in RPMI-1640 supplemented with 15% fetal bovine serum. After pelleting and washing with phosphate-buffered saline (PBS), the protein extracts were resuspended in 3 volumes of M-PER reagent (Pierce) supplemented with complete protease inhibitor cocktail (Roche Biochemicals). Protein concentrations were determined by the BCA assay kit (Pierce) and 20 $\mu$g of protein were resolved in a 4–12% NuPage gel in MES buffer (Invitrogen) before transfer to PVDF membranes. Western blots were performed using the Western Breeze kit (Invitrogen). Monoclonal antibodies specific for PRKAR1A were used as specified by the manufacturer (BD Transduction).

Western blotting of cellular proteins from a primary cell line from the CAR20.03 pituitary tumor and an PRKAR1$\alpha$-specific antibody demonstrated the presence of full length PRKAR1A in the cells (FIG. 4, Panel C, lane 1). However, no truncated forms of the protein were observed. Control experiments with bacterially expressed GST-fusion proteins confirmed the ability of this antibody to detect the truncated protein (FIG. 4, Panel C, lanes 2–4). Lane 2 contained PRKAR1A nt 74–1228 (full length, expected size 72 kD), while lane 3 contained PRKAR1A nt 74–871 (exon 8 truncation, expected size 59 kD), and lane 4 contained PRKAR1A nt 74–577 (exon 4B truncation, expected size 48 kD). In FIG. 4, size markers are indicated on the left; arrowheads denote the expected size of the fusion proteins. It is likely that the smaller sized bands represent degradation products.

EXAMPLE 9

Generation and Western Blotting of GST-PRKAR1A Fusion Proteins

Normal adrenal gland mRNA was obtained from cadavers and reverse transcribed into cDNA using the Marathon cDNA kit (Clonetech). PCR primers containing attB sequences were designed using VectorNTI software (Informax) to amplify fragments of the PRKAR1A cDNA in-frame with the attP sequences of the Gateway Cloning System (Life Technologies).

Fragments of the cDNA corresponding to nucleotides 74–577, 74–871, and 74–1228 were PCR amplified using 0.2 $\mu$l Taq polymerase and 0.5 $\mu$l Pfu polymerase in 20 $\mu$l PCR reactions (1 cycle of 95° C. for 5 minutes, 30 cycles of 94° for 30 seconds, 57° C. for 30 seconds, 72° C. for 2 minutes, 1 cycle of 72° C. for 7 minutes, and cooled to 4° C.), and cloned into pDONR201 as directed by the manufacturer (Life Technologies). The primer sequences used are shown below:

```
PRKAR1A-GWF74:
GGGGACAAGTTTGTACAAAAAAGCAGGCTGTCCCCAGAGAACCATGGAG (SEQ ID NO:63)

PRKAR1A-GWR577:
GGGGACCACTTTGTACAAGAAAGCTGGGTCAGTCTCTCCTGCGATAAAG (SEQ ID NO:64)

PRKAR1A-GWR871:
GGGGACCACTTTGTACAAGAAAGCTGGGTACTTGTCCAGAGACTCTAAA (SEQ ID NO:65)

PRKAR1A-GWR1228:
GGGGACCACTTTGTACAAGAAAGCTGGGTCAGACAGTGACACAAAACTG (SEQ ID NO:66)
```

The sequences were verified and Gateway Technology (Life Technologies) was used to transfer the inserts into pDEST15 (Life Technologies), which contains an N-terminal GST coding region under the control of the T7 promoter. The constructs were then transformed into BL21 (SI) cells (Life Technologies). To prepare bacterial proteins, bacteria containing the appropriate vectors were grown overnight in LB broth with or without 0.17 M sodium chloride. As no difference in growth characteristics was noted, all subsequent experiments were conducted using LB broth with salt added. Then, 1.5 ml of bacteria were pelleted and resuspended in 300 µl B-PER reagent as directed by the manufacturer (Pierce). Then, 18 µl of the suspension were run on a NuPage gel and Western blotted as described above. The anti-GST antibody (Pierce) was used at a 1:1000 dilution.

EXAMPLE 10

Effect of the Mutation on PRKAR1A mRNA Levels

Lymphocytes from individual patients had been established by EBV transformation of fresh lymphocytes, as known in the art (See e.g., Stratakis et al., J. Clin. Invest., 97:699–705 [1996]), and maintained in culture in RPMI 1640 with 10% fetal bovine serum. For cycloheximide (CHX) treatment, individual flasks were split into two. One flask was treated with 100 ug/ml CHX (Calbiochem), and the other was treated with vehicle only. Cells were grown for 4 hours and then RNA was prepared using the RNAEasy kit (Qiagen). First strand cDNA was prepared using an oligo dT primer (cDNA synthesis kit, Roche Biochemicals), which was then used directly for PCR analysis, as described above.

Treatment of transformed lymphocytes from the CAR01 family that carried the 578delTG mutation with CHX, followed by cloning of its cDNA and sequencing (as described above) revealed that this treatment led to the production of mRNA containing the expected 2-bp deletion, as evidenced by the disruption of the sequence trace. Similarly, treatment of transformed lymphocytes and a tissue cell line from family CAR25 that carried the exon 8 IVS +3G>A mutation with CHX led to the induction of a readily visible splice variant cDNA, which was the result of a cryptic splice donor site produced by mutation of the cognate site. Subsequent sequence analysis also showed that this led to the presence of a premature stop codon in the mRNA.

In contrast to this, the A88G mutation, which abolishes the translational start codon (See, Table 13) but does not introduce a premature stop codon, would not be predicted to be subject to NMD. Analysis of mRNA from a patient carrying this mutation (family CAR19) demonstrated that the mRNA population was a 50:50 mixture of wild-type and mutant mRNA. In Western blotting studies from this patient, no shortened forms of PRKAR1A were detected. Analysis of the primary sequence of the mRNA revealed that after the cognate ATG, there are two out of frame ATG sequences, neither of which is part of a Kozak initiation consensus (Kozak, J. Biol. Chem., 266:19867–19870 [1991]). There was an in-frame ATG which is located within a reasonably good match sequence (at least equivalent to the cognate), which would be predicted to produce a protein lacking the 46 N-terminal amino acids of the protein. However, this protein was not detected in patients' cells.

Figure 9:
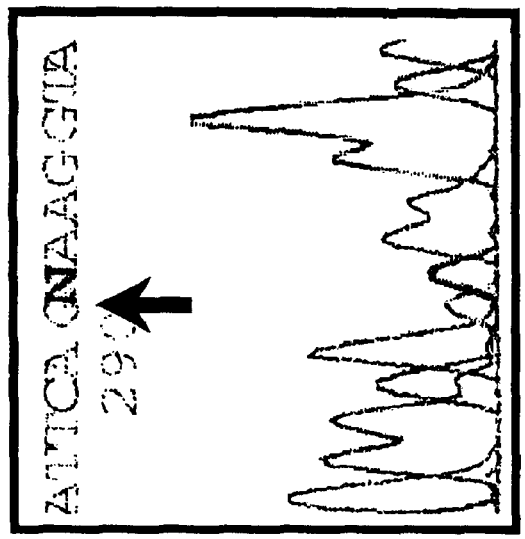
FIG. 9 provides data for the two PRKAR1A mutations that were identified in sporadic thyroid carcinomas. In this Figure, their location on the gene map is shown in the upper right panel. Panel A shows the 499C>T mutation in exon 4B which was identified in a UTC; it leads to substitution of a Gln residue with a termination codon (Q167X) in the RIα protein sequence. Panel B shows results for a PTC, in which an intronic 2-bp deletion, IVS7–78delTT, was found.
Figure 9:
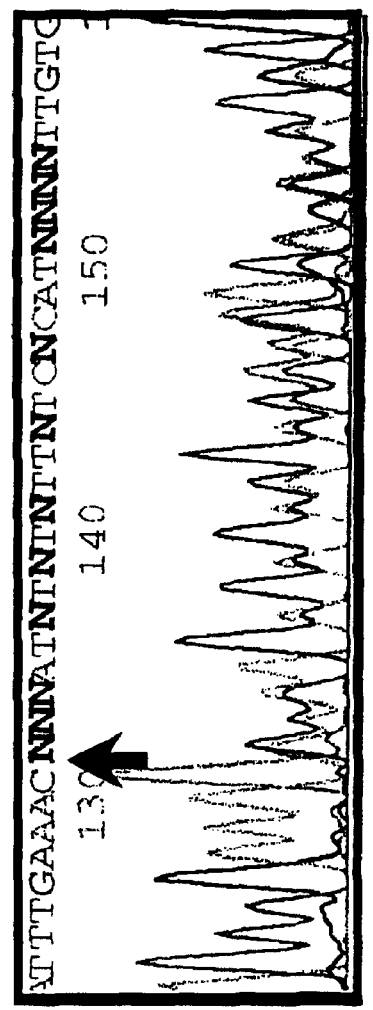

FIG. 9 provides a schematic showing the gene structure and locations of mutations PRKAR1A in 22 kindreds with CNC. The structure of the PRKAR1A gene is shown, with the locations of the exons as indicated. In this Figure, each symbol represents one family unit (kindred or sporadic case) with a mutation in that location. Circles indicate nonsense mutations, squares indicate frameshifts, and triangles indicate splice site mutations. Each of the mutations in exon 4B represents the same two base pair deletion. One of the exon 2 nonsense mutations and the exon 3 splice site mutation are indicated in two kindreds each, whereas all other mutations are unique.

EXAMPLE 11

Thyroid Tumor Analysis

In this Example, experiments conducted to assess loss-of-heterozygosity of the 17q22–24 chromosomal region, mutations of the gene encoding PRKAR1A and RIα expression in sporadic benign and malignant thyroid tumors are described.

In these experiments, none of the patients tested had clinical features of CNC. DNA was extracted from peripheral blood leukocytes (PBL) as well as snap-frozen and paraffin-embedded tumor samples, using standard methods known in the art.

The diagnoses of individual thyroid tumor types were provided by staff pathologists who examined the tissues. These diagnoses were based on current criteria (Solberg et al., Endocrinol., 138:169–181 [1997]). UTCs could also be classified as "anaplastic" carcinomas. In total, 9 follicular adenomas (FAs), 19 PTCs, 2 FTCs, and 14 UTCs were analyzed. Thirty-three (33) pairs of DNA samples were available for LOH analysis (5 from FAs, 14 from PTCs, and 14 from UTCs), but only 27 (3 FAs, 10 PTCs, and 14 UTCs) of these samples gave results that could be used for analysis, due to the poor quality DNA extracted from six (6) paraffin-embedded samples, which resulted in DNA amplification failure.

Microsatellite and Loss-of Heterozygosity Analysis

Figure 7:
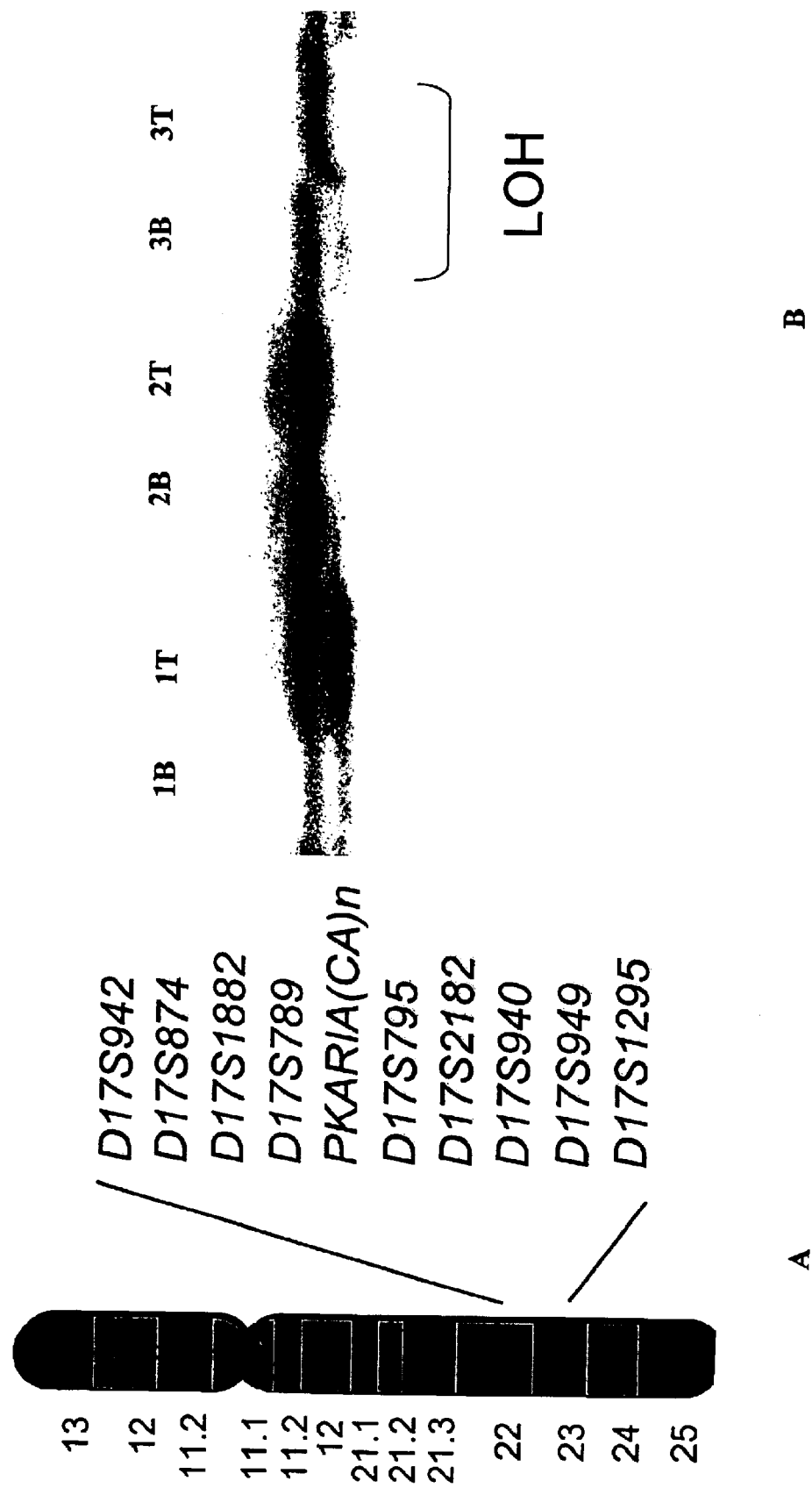
FIG. 7, Panel A shows the location of the PRKAR1A gene on chromosome 17 surrounded by dinucleotide-repeat polymorphic markers in a centromere-to-telomere order. The PRKAR1A (CA)n dinucleotide repeat marker is located in the 5' region of the PRKAR1A gene. Panel B provides an example of LOH: three blood-tumor pairs; 1B/1T: normal (both specimens retained heterozygosity), 2B/2T: uninformative (both specimens show a homozygous amplification), 3B/3T: loss of the lower allele is observed in the tumor specimen.
Figure 8:
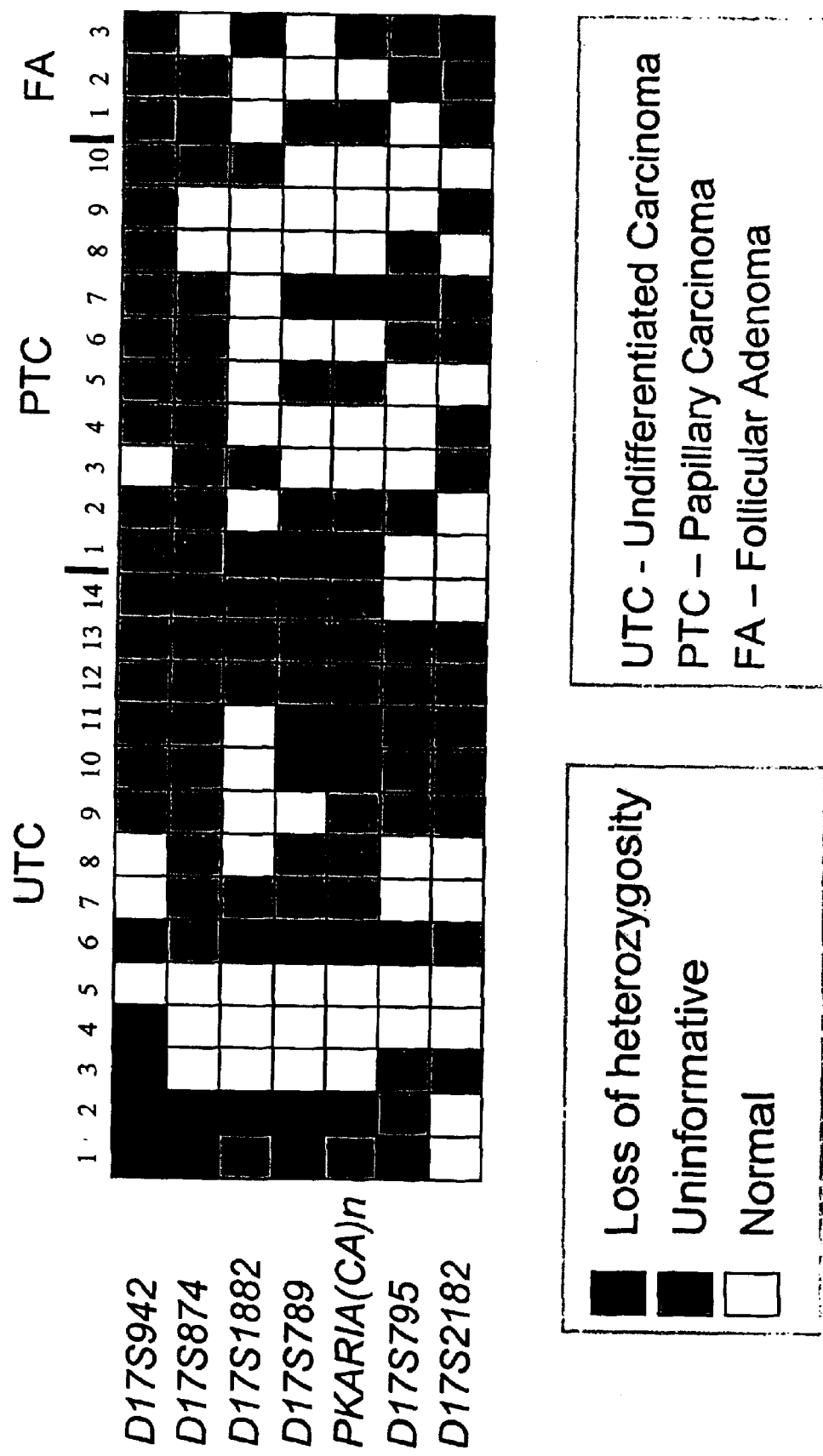
FIG. 8 provides an LOH analysis of the 17q22–24 PRKAR1A locus in thyroid tumors. Specimens 1, 2, 6, 10, and 11 from UTC's (undifferentiated thyroid cancer), and 1 and 7 from papillary thyroid carcinomas (PTCs) show consistent and contiguous changes that include the PRKAR1A intragenic marker. There are inconsistent changes for some markers in FA's; these changes are not unusual even in benign tumoral tissue, but their significance is questionable in the absence of consistency (for example, marker D17S1882 demonstrated LOH in FA 3, but both flanking markers (D17S874 and D17S789) were normal. The telomeric markers D17S940, D17S949 and D17S1295 (See, FIG. 7) produced mostly uninformative results and their data were not included in this Figure.

The polymorphic markers from 17q22–24 surrounding the PRKAR1A gene are listed in FIG. 7, Panel A in a centromere-to-telomere order. The sequences and genomic order of these primers are available in the genome database on line (http://gdbwww.gdb.org/ and http://www-genome.wi.mit.edu) (See also, Kirschner et al., Hum. Mol. Genetics 9:3037–3046 [2000]). A CA repeat within the PRKAR1A gene [PRKAR1A (CA)n] was also used (See, Kirschner et al, Nat. Genet., 26:89–92 [2000]; and Kirschner et al., Hum. Mol. Genet., 9:3037–3046 [2000]). For each of the markers, the reverse primer was end-labeled with $\gamma$-$^{32}$P, as known in the art (See, Stratakis et al., J. Clin. Endocrinol. Metab., 81:3607–3614 [1996]). FIG. 7, Panel B provides an example of LOH for three blood-tumor pairs; 1B/1T: normal (both specimens retained heterozygosity), 2B/2T: uninformative (both specimens show a homozygous amplification), and 3B/3T: loss of the lower allele is observed in the tumor specimen.

The microsatellite alterations seen in the tumors were classified according to established criteria (See, Stratakis et al., [1996], supra). Briefly, loss-of-heterozygosity (LOH) was present when only one allele was evident in tumor DNA versus two alleles in the corresponding bands of PBL DNA. Microsatellite length instability was present, when multiple bands were seen in the amplified tumor DNA versus one or two in PBL DNA. Specimens that were not successfully amplified were excluded from the analysis; only informative loci in both tumor and PBL samples were studied for LOH.

The LOH data are summarized in FIG. 7. Other microsatellite abnormalities, such as instability or size discrepancies were not present. A total of 27 blood-tumor paired samples were evaluated, as indicated in FIG. 7. There were no blood samples or other normal tissue for the 2 FTC's, so they were not included in this type of analysis and were only screened for PRKAR1A mutations (See below). As indicated in FIG. 7, FA's did not demonstrate significant or consistent LOH, or any other changes. In contrast, LOH for the PRKAR1A(CA)n locus was observed in 7 of 16 informative samples: 2 of 8 PTCs (specimens 1 and 7 of the PTCs) and 5 of 7 UTCs (specimens 1, 2, 6, 10 and 11); the remaining informative sample was a FA, which gave a normal result (specimen 2 of the FA's). One additional sample (specimen 1 of the UTCs was not informative for PRKAR1A(CA)n but demonstrated LOH for the flanking markers D17S789 and D17S795, suggesting that this sample, too, underwent LOH for this chromosomal locus. Specimen 3 of the FA's had LOH for the distant marker D17S2182 but was uninformative for the proximal marker D17S795 and for PRKAR1A(CA)n and normal for D17S789. Thus, this FA was overall uninformative, because the exact breakpoint of the LOH could not be determined by these and other markers (data not shown) that were tested in the region.

PRKAR1A Denaturing High-Performance Liquid Chromatography (DHPLC) Analysis and Sequencing The cDNA structure of human PRKAR1A was previously described by Solberg et al. (Solberg et al., Endocrinol., 138:169–181 [1997]). The revised intron-exon structure of that gene and conditions for generation of the respective amplicons was recently published (See, Kirschner et al., Nat. Genet., 26:89–92 [2000]; and Kirschner et al., Hum. Mol. Genet., 9:3037–3046 [2000]). DNA samples were PCR-amplified in 30 $\mu$l volumes using AmpliTaq Gold (Perkin-Elmer); 10 $\mu$l samples were injected into a DHPLC instrument (HELIX, Varian) at column temperatures recommended by the DHPLC Melt program (http://insertion.stanford.edu/melt.html), as known in the art (O'Donovan et al., Genomics 52:44–49 [1998]; and Jones et al, Clin. Chem., 45:1133–1140 [1999]).

Heteroduplex (D-HPLC) analysis of the PRKAR1A gene was performed in all samples (data not shown). Sequencing analysis of each exon of the PRKAR1A was performed in all samples that showed LOH or formation of heteroduplexes.

A 499C>T mutation was detected in DNA isolated from one of the UTCs. This nucleotide change in exon 4B of the PRKAR1A gene leads to substitution of a Gln residue with a termination codon (Qi67X) in the RI$\alpha$ protein sequence (See, FIG. 9, Panel A). In a PTC, an intronic 2-bp deletion, IVS7–78delTT, was observed (See, FIG. 9, Panel B). However, PRKAR1A cDNA sequencing from this sample did not show any alterations (data not shown).

Analysis of Mutations

In samples with LOH or suggestive of heterozygosity, the remaining 20 $\mu$l was purified using a PCR clean-up kit (GFX, Amersham-Pharmacia Biotech), and sequenced using the BigDye Terminator kit (Perkin-Elmer). After electrophoresis on an ABI 377 fluorescent sequencer (Perkin-Elmer), the sequence traces were analyzed using either Sequencher (Genecodes) or Vector NTI (Informax) using suitable conditions as known in the art (See, Kirschner et al., Nat. Genet., 26:89–92 [2000]; and Kirschner et al., Hum. Mol. Genet., 9:3037–3046 [2000]).

When available, frozen thyroid tumor tissue was used for mRNA extraction, PRKAR1A cDNA amplification and sequencing.

Immunohistochemistry

Sections from paraffin-embedded thyroid tumors were hybridized with a monoclonal antibody specific for RI$\alpha$ under conditions specified by the manufacturer (BD Transduction Laboratories). At least 2 blinded readers graded the specimens for RI$\alpha$ staining.

IHC showed moderately intense staining for RI$\alpha$ in all FA's. Decreased expression of RI$\alpha$ was seen in carcinomas that had demonstrated LOH in the molecular genetic studies (data not shown) versus tumors that showed no abnormalities. In a sample of benign FA stained with PRKAR1A (RI$\alpha$)-specific antibody, all of the follicular cells stained, albeit with variable intensity. In contrast, a PTC variant (without classical papillary structures) that did not show LOH for the 17q markers (sample 4 of PTC's; See, FIG. 7) showed diffuse staining of cancer cells with the Rio antibody is shown. A sample from a UTC demonstrating LOH for the PRKAR1A locus at 17q (sample 10 of UTC's; See, FIG. 7) and bearing the 499C>T PRKAR1A (inactivating) mutation showed no staining for the RI$\alpha$ antibody in tumor cells. However, the endothelial cells lining blood vessels showed staining as expected.

EXAMPLE 12

Antisense mRNA Targeting

In this Example, experiments conducted using antisense mRNA targeting to generate mice with reduced amounts of PRKAR1A to model the apparent haploinsufficiency observed in human disease are described. By placing the antisense transcript under the control of an artificial promoter containing tetracycline (Tet) regulatory elements (TREs) as known in the art (See e.g., Gossen and Bujard, Proc. Natl. Acad. Sci. USA 89:5547–5551 [1992]), tight control of the timing and amount of antisense mRNA produced by the animals is achieved by simply administering tetracycline in the animals' drinking water (e.g., 1 mcg/ml), with the water bottles being changed every 2–3 days. However, in preferred embodiments, mice are treated with the tetracycline congener doxycycline (Doxy) because it has better stability and kinetics. The doses that are used for regulation of the artificial promoter are non-toxic to the mice and there is a good dose-response curve of the promoter to the dose of Doxy administered. This system allows control of the timing and amounts of reduction in the PRKAR1A protein.

In initial experiments, transgenic mice carrying a fragment of the prkar1a cDNA cloned in the antisense orientation under the control of a TRE will be crossed with mice carrying the Tet transactivator protein (tTA). This protein binds to and constitutively activates TRE-containing promoters, except in the presence of Doxy or Tet. In these experiments, mice hemizygous for either the r1a-AS or rTA transgenes are crossed, in order generate double heterozygote mice from each of the r1a-AS founder sublines.

The offspring of this cross are genotyped and phenotyped to observe for the presence of embryonic effects of the antisense expression. If none are observed, mice are maintained in the absence of Doxy for approximately two (2) years, to watch for the development of tumors similar to those observed in CNC. In order to monitor this progress, mice are sacrificed at six (6) month intervals to observe for the presence of tumors. In these experiments, mice that exhibit no phenotype and are double heterozygotes are maintained as the experimental group, while mice that are hemizygous only for the r1a-AS transgene are maintained as a control group. Indeed, "double TG" (TGTG pattern, as described above) mice have been produced using these methods. It is contemplated that these animals, as well as the other animal models described herein will find use in further assessments of CNC and other diseases.

In the case where double heterozygote mice are either not born or exhibit developmental malformations, two different approaches are used. First, female mice are treated with Doxy before mating and for specified periods of time during gestation. This facilitates the determination of in which gestation periods full prkar1a expression is/are necessary for development. In the second line of investigation, mice are treated with Doxy throughout gestation and the antimicrobial removed after weaning. This allows the investigation of the tumorigenesis aspect of the phenotype rather than developmental aspect. Using the dose-response curve of the promoter for Doxy (See, Kistner et al., Proc. Natl. Acad. Sci. USA 93:10933–10938 [1996]), it is contemplated that the level of prkar1a needed to prevent tumor development will be determined and monitored over time.

EXAMPLE 13

Conditional Knockout Animals

In this Example, experiments to construct conditional knockout mice are described. In this model, a pair of loxP sites are introduced around the first and second exon of the prkar1a gene. Incubation of cells containing this construct with the cre recombinase leads to excision of the first and second exons of the gene and a null allele. Mice containing this floxed prkar1a allele are used to address various aspects of CNC disease and pathogenesis.

In one embodiment, a heterozygous null animal is provided as an "exact" genetic model for human CNC patients. These mice are normal at birth but develop tumors as they age. In some embodiments, heterozygous nulls are bred and sacrificed at bimonthly intervals up to two (2) years of age. As CNC patients tend to present with tumors in their second and third decades of life, this time frame provides a suitable window in which to observe the development of tumors.

In other embodiments, the same system is used to create homozygous null animals to examine the effects of the lack of PRKAR1A on development. Preliminary information has indicated that homozygous nulls are embryonic lethal, which is a strong reason for beginning experiments using a knockout approach. PRKAR1A is expressed ubiquitously in tissues, so it is not completely unexpected that the complete knockout has this phenotype. The endocrine organs of these animals are observed for malformations. To verify that the homozygous null gives a lethal phenotype, mice homozygous for the conditional allele are crossed with the FVB/N-TgN(EIIa-Cre)C5379Lmgd line which expresses cre recombinase in the 1-cell embryonic stage, in order to create null animals.

In still further embodiments, mice homozygous for the floxed prkar1a allele are mated with mice expressing cre recombinase in well-defined tissues. These animals provide means to examine the effects of loss of this gene product on tumor formation. In some embodiments, target mice include those expressing cre under the control of the keratin K5 promoter (Tarutani et al., Proc. Natl. Acad. Sci. USA 94:7400–7405 [1997]), to examine pigmentation and tumors in the skin. In other embodiments, target mice including those expressing cre in neuroendocrine cells under the control of the tyrosinase promoter. The resulting offspring are observed for the development of phenotypic traits associated with CNC (e.g., myxomas, endocrine tumors, skin pigmentation abnormalities, etc.).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art of synthetic chemistry and/or related fields are intended to be within the scope of the following claims.

We claim:

1. A nucleotide sequence of mutant protein kinase regulatory subunit 1A gene, wherein said mutation is SEQ ID NO:41.

* * * * *